United States Patent
Brayshaw et al.

(10) Patent No.: US 10,683,360 B2
(45) Date of Patent: Jun. 16, 2020

(54) TARGETED PROTEIN DEGRADATION

(71) Applicant: GLAXOSMITHKLINE INTELLECTUAL PROPERTY DEVELOPMENT LIMITED, Brentford (GB)

(72) Inventors: Lewis Lee Brayshaw, Stevenage (GB); Michael Menteith Hann, Stevenage (GB); Christopher Herring, Stevenage (GB); Carlos Martinez Fleites, Stevenage (GB); Markus Alexander Queisser, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 16/024,999

(22) Filed: Jul. 2, 2018

(65) Prior Publication Data
US 2019/0002578 A1  Jan. 3, 2019

(30) Foreign Application Priority Data
Jul. 3, 2017  (GB) .................................. 1710620.4

(51) Int. Cl.
| | | |
|---|---|---|
| C12N 15/62 | (2006.01) | |
| C07K 14/47 | (2006.01) | |
| C07K 16/28 | (2006.01) | |
| C07K 14/725 | (2006.01) | |
| C07K 14/705 | (2006.01) | |
| C07K 16/00 | (2006.01) | |
| A61K 39/00 | (2006.01) | |
| A61K 38/17 | (2006.01) | |
| A61K 39/395 | (2006.01) | |

(52) U.S. Cl.
CPC ...... *C07K 16/2878* (2013.01); *A61K 38/1709* (2013.01); *A61K 39/001117* (2018.08); *A61K 39/39533* (2013.01); *C07K 14/7051* (2013.01); *C07K 14/70503* (2013.01); *C07K 16/00* (2013.01); *A61K 2039/5156* (2013.01); *A61K 2039/5158* (2013.01); *C07K 14/70517* (2013.01); *C07K 2317/34* (2013.01); *C07K 2317/622* (2013.01); *C07K 2319/01* (2013.01); *C07K 2319/02* (2013.01); *C07K 2319/03* (2013.01); *C07K 2319/95* (2013.01)

(58) Field of Classification Search
CPC ................ C07K 14/47; C07K 14/4701; C07K 2319/00; C07K 2319/95; A61K 31/5035; C12N 15/62
See application file for complete search history.

(56) References Cited

U.S. PATENT DOCUMENTS

2017/0119903 A1   5/2017  Park et al.

FOREIGN PATENT DOCUMENTS

| WO | WO03/016571 A1 | 2/2003 | |
|---|---|---|---|
| WO | WO2017/024318 A1 | 2/2017 | |
| WO | WO-2017117118 A1 * | 7/2017 | ......... G01N 33/5008 |
| WO | WO2018/075820 A2 | 4/2018 | |

OTHER PUBLICATIONS

UniProtKB downloaded 2019, at www.uniprot.org/uniprot/Q13422.*
Matyskiela, et al., A Cereblon Modulator (CC-220) with Improved Degradation of Ikaros and Aiolos, *Journal of Medicinal Chemistry*, 61:535-542 (2018).
Matyskiela, et al., A novel cereblon modulator recruits GSPT1 to the CRL4 (CRBN) ubiquitin ligase, *Nature*, 535:252-257 (2016).
Melvin, et al., A Comparative Analysis of the Ubiquitination Kinetics of Multiple Degrons to Identify an Ideal Targeting Sequence for a Proteasome Reporter, *PLOS One*, 8(10):e78082 (2013).
Petzold, et al., Structural basis of lenalidomide-induced CK1 alpha degradation by the CRL4(CRBN) ubiquitin ligase, *Nature*, 532:127-130 (2016).

* cited by examiner

*Primary Examiner* — Karen Cochrane Carlson
(74) *Attorney, Agent, or Firm* — James J. Kang

(57) ABSTRACT

The invention relates to a method of controlling the level of a polypeptide sequence comprising administering a polypeptide sequence fused to a ubiquitin targeting protein which comprises a minimal degron structural motif. In particular, the polypeptide sequence comprises a chimeric antigen receptor therefore the present invention is useful in methods of cell and gene therapy where the activity of the chimeric antigen receptor needs to be controlled.

11 Claims, 7 Drawing Sheets

Specification includes a Sequence Listing.

A)

| Lenalidomide Concentration [nM] | GFP+ Median Fluorescence Intensity (MFI) | | |
|---|---|---|---|
| | CONSTRUCT 1 | CONSTRUCT 2 | CONSTRUCT 3 |
| 0 | 18,216 | 56,091 | 42,043 |
| 10 | 15,778 | 47,132 | 32,130 |
| 100 | 13,987 | 26,745 | 22,361 |
| 500 | 13,284 | 26,126 | 22,263 |
| 1,000 | 14,673 | 22,173 | 19,370 |
| 10,000 | 14,024 | 18,771 | 19,521 |

B)

A)

B)

Anti-BCMA CAR fluorescence intensity

TNF-α (+ARH-77-10B5)

IL-2 (+ARH-77-10B5)

IFN-γ (+ARH-77-10B5)

TARGETED PROTEIN DEGRADATION

CROSS REFERENCE TO RELATED APPLICATION

This application claims the benefit of U.K. Provisional Application No. GB 1710620.4, filed 3 Jul. 2017.

FIELD OF THE INVENTION

The invention relates to methods of controlling the level and/or activity of a heterologous protein which has been introduced into a host cell.

BACKGROUND TO THE INVENTION

Targeted degradation of proteins has previously been achieved through strategies harnessing the ubiquitin proteasome system (UPS). In particular, Proteolysis Targeting Chimeric molecules (PROTACs) have been described in the art which are heterobifunctional compounds composed of a target protein-binding ligand and an E3 ubiquitin ligase ligand that induce proteasome-mediated degradation of the target protein via their recruitment of E3 ubiquitin ligase and subsequent ubiquitination. Such compounds are capable of inducing the inactivation of a target protein upon addition to cells or administration to an animal or human, and therefore have been proposed for the treatment of disease by removing pathogenic or oncogenic target proteins.

Chimeric antigen receptors (CARs) are artificial T-cell receptors that are at the forefront of modern personalised therapies (Lee et al. (2012) *Clin. Cancer Res.*, 18(10): 2780-90). They are being developed to treat cancers in patients that are resistant to conventionally available therapies and use a patient's own immune cells to combat the disease. The immune cells are genetically engineered ex vivo to express a CAR (CAR-T cells) specific to a tumour antigen, and the cells are subsequently transferred back to the patient. CARs reside on surfaces of T cells and consist of intracellular and extracellular domains which are separated by a transmembrane domain. The extracellular domain harbours a target binding region (e.g. a single chain variable fragment) that is directed towards an antigen solely expressed on diseased cells. The intracellular domain (usually CD3ζ-CD28 or CD3ζ-41BB) faces the cytosol and transmits an activation signal to the T cell after the antigen is bound to the target binding region on the surface of the cell. Active signalling of CAR-T cells leads further to the killing of the diseased cells.

The development of CARs has comprised three generations so far. The first generation CARs comprised target binding domains attached to a signalling domain derived from the cytoplasmic region of the CD3zeta or the Fc receptor gamma chains. First generation CARs were shown to successfully retarget T cell killing to the selected target, however, they failed to provide prolonged expansion and antitumor activity in vivo. The second and third generation CARs have focussed on enhancing modified T cell survival and increasing proliferation by including additional signalling domains from co-stimulatory molecules, such as CD28, OX-40 (CD134) and 4-1BB (CD137).

However, a safety concern of this promising therapy has arisen through potential cross-reactivity to vital organs such as the lung. Indeed, during clinical trials, both on-target as well as off-target off-tumour toxicities have been observed in patients treated with CAR-T cells and fatalities have been reported with CAR studies (Morgan et al. (2010) *Mol. Ther.*, 18(4): 843-51). These toxicities are difficult to predict in animal or non-primate models, and in contrast to small molecules and biologics, CAR-T cells are living-drugs that have unique pharmacokinetic (PK) profiles and pharmacodynamic effects. Therefore, safety switches are being developed to turn off or tune down CAR-T cell killing and allow for more controlled and safer therapies.

Suicide switches are one example of a safety switch where CAR-T cells are further engineered to express "suicide genes" or "elimination genes" which allows selective destruction of CAR-T cells upon administration of an external agent. For example, incorporating herpes simplex virus thymidine kinase (HSV-TK) means that administration of the prodrug ganciclovir results in cell death by incorporation of GCV-triphosphate into replicating DNA. However, the elements involved in this switch are immunogenic and there is emerging evidence that immune responses against HSV-TK limit the persistence of transduced cells Berger et al., (2006) Blood March 15:107(6):2294-302).

WO2017024318 describes compositions and methods for regulating chimeric antigen receptor immune effector cell therapies by attaching a dTAG which binds a heterobifunctional compound which, in turn, leads to ubiquitination.

In order for cellular therapies to be become more widely adopted, there is still a need in the art to develop methods for controlling these therapies to ensure that any adverse events can be prevented.

SUMMARY OF THE INVENTION

According to a first aspect of the invention, there is provided a method of controlling the level of a polypeptide sequence comprising:

a) administering a fusion protein comprising said polypeptide sequence and a ubiquitin targeting protein consisting of less than 135 amino acids in length which comprises the hairpin motif of a cereblon binding site, and b) controlling the level of the polypeptide sequence by administering a compound which mediates binding of the ubiquitin targeting protein and cereblon.

In another aspect of the invention there is provided a method of controlling the level of a polypeptide sequence comprising:

a) administering a fusion protein comprising:
A-B
wherein A is a polypeptide sequence; and
wherein B is a ubiquitin targeting protein consisting of less than 135 amino acids in length comprising a structural motif which when aligned has a set of structural coordinates within about 6.0 Å of the rmsd of the backbone atoms between each of the amino acid residues as listed in Table 1, and wherein the structural motif comprises a glycine residue at the position which corresponds to GLY56 of Table 1; and b) controlling the level of the polypeptide sequence by administering a compound which mediates binding of a) the ubiquitin targeting protein and b) a ubiquitin ligase in a manner that brings the polypeptide sequence into proximity of the ubiquitin ligase, wherein the polypeptide sequence, in the presence of the compound, is capable of being ubiquitinated.

According to a further aspect of the invention, there is provided a chimeric antigen receptor (CAR) comprising:
an extracellular ligand binding domain;
a transmembrane domain;
an intracellular signalling domain; and, a ubiquitin targeting protein as described herein, which is capable of being bound by ubiquitin ligase in the presence of a compound.

According to a further aspect of the invention, there is provided a fusion protein comprising a polypeptide sequence consisting of less than 135 amino acids in length, which comprises the hairpin motif of a cereblon binding site.

In another aspect of the invention there is provided a fusion protein comprising

A-B wherein A is a polypeptide sequence; and wherein B is a ubiquitin targeting protein which consists of a sequence selected from the group consisting of: SEQ ID NOs: 6-14.

DETAILED DESCRIPTION OF THE INVENTION

Figure 1:
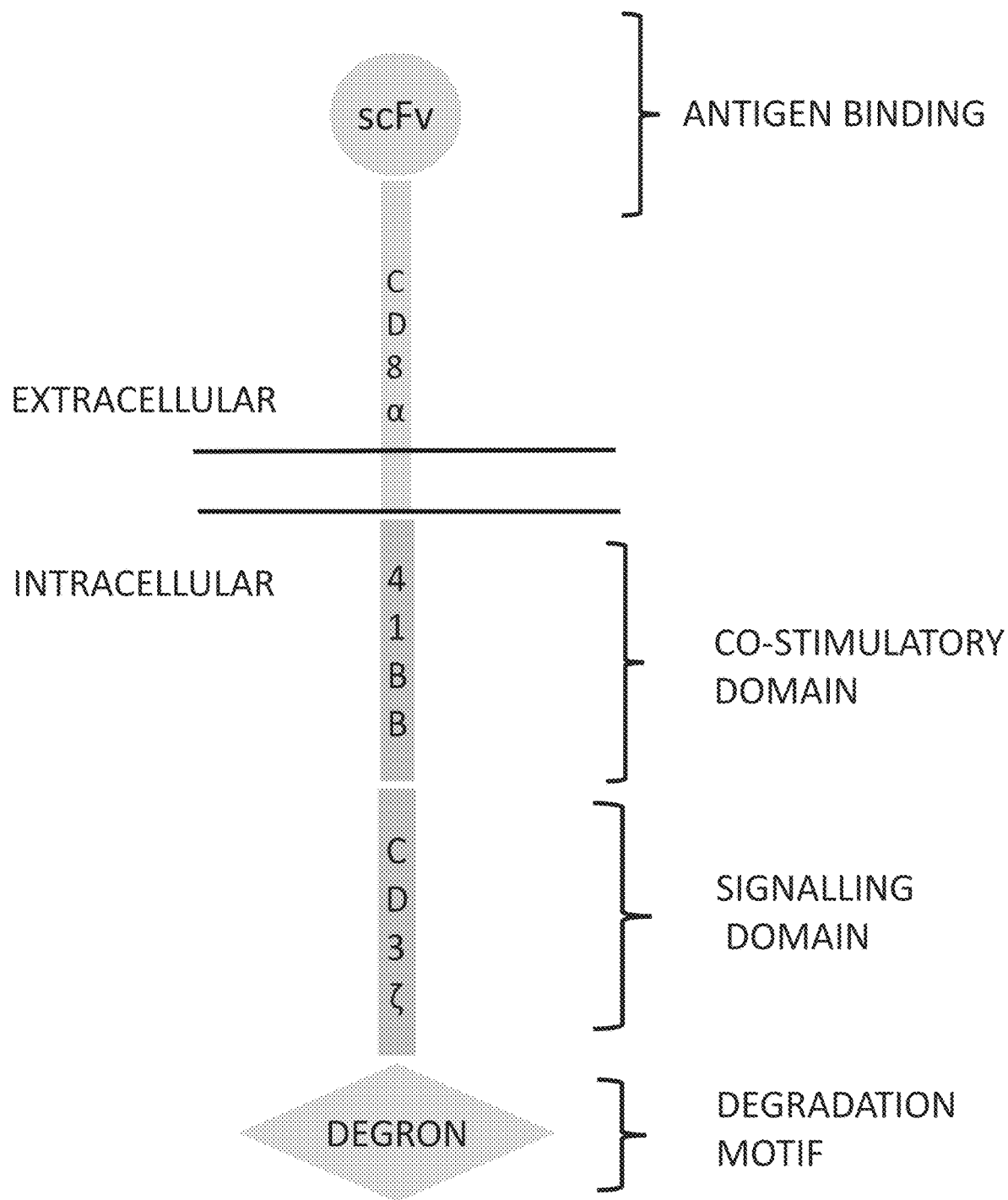
FIG. 1. Schematic organisation of chimeric antigen receptor construct that incorporates a degron element.

Described herein is an essential structural motif required for effective ubiquitination of a target protein. This can be used to control the level and/or activity of a heterologous protein administered to a target cell, especially when the heterologous protein is a therapeutic protein which needs to be tightly controlled in order to avoid the risk of any adverse effects. Minimising the size of the motif required for effective ubiquitination has advantages, especially if the heterologous protein is introduced via a viral vector where space is a premium.

Definitions

Unless defined otherwise, all technical and scientific terms used herein have the same meaning as is commonly understood by one of skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, $2^{nd}$ ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference in their entirety) and chemical methods. All patents and publications referred to herein are incorporated by reference in their entirety.

The term "comprising" encompasses "including" or "consisting" e.g. a composition "comprising" X may consist exclusively of X or may include something additional e.g. X+Y.

The term "consisting essentially of" limits the scope of the feature to the specified materials or steps and those that do not materially affect the basic characteristic(s) of the claimed feature.

The term "consisting of" excludes the presence of any additional component(s).

The term "about" as used herein when referring to a measurable value such as an amount, a temporal duration, and the like, is meant to encompass variations of ±20% or ±10%, including ±5%, ±1%, and ±0.1% from the specified value.

The term "safety switch" refers to a biochemical mechanism that can be activated on demand in order to control a biological process which can cause harm. Safety switches can be used with CAR-T therapies so that they can be controlled externally (i.e. via administration from outside of the cell) in order to enhance the safety of the gene therapy.

The term "chimeric antigen receptors" ("CARs") as used herein, refers to an engineered receptor which consists of an extracellular target binding domain (which is usually derived from a monoclonal antibody or fragment thereof), optionally a spacer region, a transmembrane region, and one or more intracellular effector domains. CARs have also been referred to as chimeric T cell receptors or chimeric immunoreceptors (CIRs). CARs are genetically introduced into hematopoietic cells, such as T cells, to redirect specificity for a desired cell-surface antigen. More recently CARs have also been introduced to non-immune cells (Kojima et al., 2018 Nature Chem. Bio. January; 14(1):42-49).

References to "CAR signalling" refer to signalling through the signalling domain of the CAR which results in immunomodulatory cell activation (e.g. triggering target cell killing and T cell activation).

The term "T cell receptor" ("TCR") as used herein, refers to the receptor present on the surface of T cells which recognises fragments of antigen as peptides bound to major histocompatibility complex (MHC) molecules. Native TCRs exist in αβ and γδ forms, which are structurally similar but exist in different locations and are thought to have different functions. The extracellular portion of the TCR has two constant domains and two variable domains. The variable domains contain polymorphic loops which form the binding site of the TCR and are analogous to complementarity determining regions (CDRs) in antibodies. In the context of gene therapies, the TCR is usually genetically modified to change or improve its antigen recognition, therefore in one embodiment, the TCR is genetically modified. For example, WO01/055366 and WO2006/000830, which are herein incorporated by reference, describe retrovirus-based methods for transfecting T cells with heterologous TCRs.

The term "target binding domain" as used herein is defined as an oligo- or polypeptide that is capable of binding a specific target, such as an antigen or ligand. In particular, the target may be a cell surface molecule. For example, the target binding domain may be chosen to recognise a target that acts as a cell surface marker on pathogenic cells, including pathogenic human cells, associated with a particular disease state. The target binding domain may be, for example, any type of protein which binds to an antigen.

The term "spacer region" as used herein, refers to an oligo- or polypeptide that functions to link the transmembrane domain to the target binding domain. This region may also be referred to as a "hinge region" or "stalk region". The size of the spacer can be varied depending on the position of the target epitope in order to maintain an optimum distance for activation of the immune synapse (e.g. 14 nm) upon CAR:target binding.

The term "domain" refers to a folded protein structure which retains its tertiary structure independent of the rest of the protein. Generally, domains are responsible for discrete functional properties of proteins and in many cases, may be added, removed or transferred to other proteins without loss of function of the remainder of the protein and/or of the domain.

The term "transmembrane domain" as used herein refers to a domain which traverses the cell membrane.

The term "intracellular effector domain" as used herein refers to the domain in the CAR which is responsible for intracellular signalling following the binding of the target binding domain to the target. The intracellular effector domain is responsible for the activation of at least one of the normal effector functions of the immune cell in which the CAR is expressed. For example, the effector function of a T cell can be a cytolytic activity or helper activity including the secretion of cytokines.

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanised, multispecific antibodies, including bispecific antibodies, and heteroconjugate antibodies; a single variable domain (e.g., VH, VHH, VL, domain antibody (dAb)), antigen binding antibody fragments, Fab, F(ab')$_2$, Fv, disulphide linked Fv, single chain Fv, disulphide-linked scFv, diabodies, TANDABS, etc., and modified versions of any of the foregoing.

The term "single variable domain" refers to a folded polypeptide domain comprising sequences characteristic of antibody variable domains. It therefore includes complete antibody variable domains such as VH, VHH and VL and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain is capable of binding an antigen or epitope independently of a different variable region or domain. A "domain antibody" or "dAb" may be considered the same as a "single variable domain". A single variable domain may be a human single variable domain, but also includes single variable domains from other species such as rodent (for example, as disclosed in WO 00/29004), nurse shark and Camelid VHH dAbs. Camelid VHH are immunoglobulin single variable domain polypeptides that are derived from camelid species including bactrian and dromedary camels, llamas, vicugnas, alpacas, and guanacos, which produce heavy chain antibodies naturally devoid of light chains. Such VHH domains may be humanised according to standard techniques available in the art, and such domains are considered to be "single variable domains". As used herein VH includes camelid VHH domains.

For the avoidance of doubt, it will be understood that the terms "polynucleotide", "nucleotide" and "nucleic acid" are used interchangeably herein.

For the avoidance of doubt, it will be understood that the terms "polypeptide", "oligopeptide" "peptide" and "amino acid" are used interchangeably herein.

For the avoidance of doubt, it will be understood that the terms "structural motif" and "hairpin motif" are used interchangeably herein.

References to "fusion protein" refer to a protein translated from a fusion gene, which is created by joining parts of two different genes/nucleic acid sequences. The polypeptide sequence A and ubiquitin targeting protein B are associated with one another, preferably by genetic fusion (i.e. the fusion protein is generated by translation of a nucleic acid in which a polynucleotide encoding all or a portion of A is joined in-frame with a polynucleotide encoding all or a portion of B) or chemical conjugation to one another.

References to "functional fragments" refer to fragments of the full, wild-type sequences which still retain the binding function of the wild type protein from which they are derived (e.g. functional fragments of the ubiquitin targeting protein still enable binding to the compound which mediates the interaction with the ubiquitin ligase). Fragments may suitably comprise at least 10 amino acids in length, for example 25, 50, 75, 80, 90, 100, 110, 120 or 130 amino acids in length. Fragments may also comprise a C-terminal truncation, or an N-terminal truncation.

References to "functional variants" include variants with similar amino acid or nucleotide sequences to the original (e.g. wild-type) sequences, but with one or more amino acid or nucleotide changes that result in a variant which still retains the function of the original protein from which they are derived. For example, a functional variant of the ubiquitin targeting protein described herein include variants that still facilitate sufficient binding to the compound which enables ubiquitination of the polypeptide sequence via the ubiquitin ligase.

"Affinity" is the strength of binding of one molecule, e.g. the target binding protein, to another, e.g. its target antigen, at a single binding site. The binding affinity of a target binding protein to its target may be determined by equilibrium methods (e.g. enzyme-linked immunoabsorbent assay (ELISA) or radioimmunoassay (RIA)), or kinetics (e.g. BIACORE analysis).

Sequence identity as used herein is the degree of relatedness between two or more amino acid sequences, or two or more nucleic acid sequences, as determined by comparing the sequences. The comparison of sequences and determination of sequence identity may be accomplished using a mathematical algorithm; those skilled in the art will be aware of computer programs available to align two sequences and determine the percent identity between them. The skilled person will appreciate that different algorithms may yield slightly different results.

Thus, the "percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query nucleic acid sequence may be described by a nucleic acid sequence identified in one or more claims herein.

Similarly, the "percent identity" between a query amino acid sequence and a subject amino acid sequence is the "Identities" value, expressed as a percentage, that is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query amino acid sequence may be described by an amino acid sequence identified in one or more claims herein.

The query sequence may be 100% identical to the subject sequence, or it may include up to a certain integer number of amino acid or nucleotide alterations as compared to the subject sequence such that the % identity is less than 100%. For example, the query sequence is at least 50, 60, 70, 75, 80, 85, 90, 95, 96, 97, 98, or 99% identical to the subject sequence. Such alterations include at least one amino acid deletion, substitution (including conservative and non-conservative substitution), or insertion, and wherein said alterations may occur at the amino- or carboxy-terminal positions of the query sequence or anywhere between those terminal positions, interspersed either individually among the amino acids or nucleotides in the query sequence or in one or more contiguous groups within the query sequence.

The term "ubiquitin targeting protein" refers to the protein/domain/fragment which is capable of inducing ubiquitination of the polypeptide sequence by binding ubiquitin ligase in the presence of a compound.

The term "ubiquitin ligase", also known as E3 ligase, refers to a family of proteins that facilitate the transfer of ubiquitin-alone or in complex- to a specific substrate protein, therefore targeting the substrate protein for degradation. For example, cereblon is part of an E3 ubiquitin ligase complex Cul4A/B that in combination with an E2 ubiquitin-conjugating enzyme causes the attachment of ubiquitin to a lysine on a target protein, and subsequently targets the specific protein for degradation by the proteasome. The ubiquitin ligase may be involved in polyubiquitination such that more than one ubiquitin is attached to the target protein. For example, a second ubiquitin is attached to the first ubiquitin; a third is attached to the second, and so forth. Polyubiquitination can mark proteins for degradation by the proteasome.

The term "ubiquitination site" refers to the amino acid residue, in particular, a lysine residue to which ubiquitin is attached. In order to make a chain, ubiquitin itself contains a ubiquitination site. Different lysines on ubiquitin can be targeted by an E3 to make chains, but the most common lysine is Lys48. This lysine-48 may be used to make polyubiquitin, which is then recognized by the proteasome.

The term "autologous" as used herein, refers to cells from the same subject. The term "allogeneic" as used herein, refers to cells of the same species that differ genetically to the cell in comparison.

The terms "individual", "subject" and "patient" are used herein interchangeably. In one embodiment, the subject is a mammal, such as a primate, for example a marmoset or monkey, or a human. In a further embodiment, the subject is a human.

The term "pharmaceutical composition" refers to a composition formulated in pharmaceutically-acceptable or physiologically-acceptable solutions for administration to a cell or subject. The compositions of the invention may be administered in combination with other agents as well, provided that the additional agents do not adversely affect the ability of the composition to deliver the intended therapy.

The term "cancer" (sometimes also referred to as "neoplasia") refers to a disease caused by an uncontrolled division of abnormal cells in a part of the body. The uncontrolled division can often result in a mass, commonly referred to as a "tumour" or "neoplasm". The term "tumour associated antigen" or "tumour antigen" as used herein, refers to an antigen expressed on a tumour cell. This antigen may be uniquely or differentially expressed on a tumour cell when compared to a normal, i.e. non-cancerous, cell.

The invention described herein may also be used in methods of treatment of a subject in need thereof. Treatment can be therapeutic, prophylactic or preventative. Treatment encompasses alleviation, reduction, or prevention of at least one aspect or symptom of a disease and encompasses prevention or cure of the diseases described herein.

Methods of Controlling Protein Levels

Structural conservation of the cereblon binding site has been observed for CK1 and GSTP1. For Ikaros 1 and 3, the structural conservation has been inferred by homology to structurally characterized proteins such as Eos (Ikaros 4, PDB entry 2MA7) or the zinc finger protein from PDB entry 2I13. The present inventors have proposed fusing this conserved structural motif to a heterologous protein in order to provide a method of controlling the level and/or activity of said protein. In contrast to current PROTAC methods used in the art, the present method involves fusing a ubiquitin targeting protein (which may also be referred to as a ubiquitin targeting domain) directly to the protein to be controlled so that an external compound can simply be added in order to induce binding to ubiquitin ligase which results in ubiquitination.

Furthermore, by using the minimal degron required, there are potential production advantages. For example, vectors are often size limited, therefore it is helpful to have a small ubiquitin targeting protein to maximise the amount of space available to encode other polypeptide sequences.

A minimal degron is also less likely to interfere with the activity of the heterologous protein.

Therefore, according to a first aspect of the invention, there is provided a method of controlling the level of a polypeptide sequence comprising:

a) administering a fusion protein comprising said polypeptide sequence and a ubiquitin targeting protein consisting of less than 135 amino acids in length which comprises the hairpin motif of a cereblon binding site, and b) controlling the level of the polypeptide sequence by administering a compound which mediates binding of the ubiquitin targeting protein and cereblon.

In another aspect of the invention there is provided a method of controlling the level and/or activity of a polypeptide sequence comprising:

a) administering a fusion protein comprising:

A-B wherein A is a polypeptide sequence; and wherein B is a ubiquitin targeting protein consisting of less than 135 amino acids in length comprising a structural motif which when aligned has a set of structural coordinates within about 6.0 Å of the root-mean-square deviation (rmsd) of the backbone atoms between each of the amino acid residues as listed in Table 1, and wherein the structural motif comprises a glycine residue at the position which corresponds to GLY56 of Table 1; and b) controlling the level of the polypeptide sequence by administering a compound which mediates binding of a) the ubiquitin targeting protein and b) a ubiquitin ligase in a manner that brings the polypeptide sequence into proximity of the ubiquitin ligase, wherein the polypeptide sequence, in the presence of the compound, is capable of being ubiquitinated.

Without being bound by theory, once the polypeptide sequence has been ubiquitinated it can be degraded by a proteasome or attachment of ubiquitin (in particular a polyubiquitin chain) causes the polypeptide sequence to be sterically inhibited. Thus, in one embodiment, the polypeptide sequence is capable of being ubiquitinated and then degraded by a proteasome. In an alternative embodiment, the polypeptide sequence is capable of being ubiquitinated and then sterically inhibited.

Ubiquitin is a small (about 8.5 kDa) protein that has been found in most tissues of eukaryotic organisms. The addition of ubiquitin to a substrate protein is called ubiquitination or ubiquitylation. Ubiquitination can affect proteins in many ways, including signalling for their degradation via the proteasome. Ubiquitin is covalently coupled to a substrate lysine by activity of an E1 (ubiquitin activating enzyme), E2 (ubiquitin conjugating enzyme) and E3 (ubiquitin ligase) enzyme cascade. A E3 ubiquitin RING ligase is a protein that recruits an E2 ubiquitin-conjugating enzyme that has been loaded with ubiquitin, therefore E3 ubiquitin RING ligases interact with both the target protein and the E2 enzyme. One example of an E3 ubiquitin ligase is cereblon (CRBN) which interacts with damaged DNA binding protein 1 (DDB1), Cullin 4 (CUL4) and RING-box protein 1 (RBX1) to form the complex CUL4-RBX1-DDB1-CRBN. This complex then ubiquitinates the protein substrate which is subsequently degraded by proteasomes.

The method of the invention allows the level (e.g. the intracellular, extracellular or membrane levels) and/or activity of a polypeptide sequence to be controlled by fusing it to domain that allows for targeted ubiquitination upon introduction of a mediating compound. Addition of the compound can cause the level of polypeptide sequence to be reduced because the compound will induce ubiquitination of the polypeptide by ubiquitin ligase and could lead to subsequent degradation. The change in level and/or activity can be measured using methods known in the art.

It will be understood that references to "ubiquitin ligase" as used herein includes ubiquitin ligases and/or a protein which is part of the ligase complex e.g. cereblon. Therefore, in one embodiment, the ubiquitin ligase is cereblon.

Certain protein substrates have been shown to interact with E3 ubiquitin ligases through immunomodulatory drugs (e.g. IMiDs), such as thalidomide. These protein substrates include Ikaros3, Ikaros1, GSTP1 and CK1 alpha. Recently, ZFP91 was shown to be an IMiD-dependent substrate of cereblon (see An et al. (2017) Nat. Commun. 8: 15398).

A "minimal" degron is described herein, in the form of a small protein domain (around 30 amino acids) that can be added to a protein of interest for degradation. In the presence of an IMiD compound, degradation will be induced. However, the degron is not defined by the linear peptide sequence, but rather the geometric arrangement of three backbone hydrogen bond acceptors at the apex of a turn (positions i, i+1, and i+2), with a glycine residue at a key position (i+3). This geometric arrangement forms a hairpin motif.

When the hairpin motifs from three cereblon substrates were superimposed using main chain atoms, the overall rmsd was found to be around 2.0 Å. In particular, the closest structural overlap was seen around a central glycine residue which was conserved between all three motifs. The Ramachandran angles were measured in PDB entry 2I13 as a structural representative of Ikaros3 ZFN (with percentage identity of 50%) and found to be as follows:

TABLE 1

Ramachandran angles of cereblon binding hairpin motifs Ikaros3 (2I13)

| Residue | Psi (ψ) | Phi (φ) |
|---|---|---|
| LYS 51 | 151.5 | −102.8 |
| CYS 52 | 127.8 | −83.5 |
| PRO 53 | −7.5 | −66 |
| GLU 54 | −52.5 | −111.7 |
| CYS 55 | −16.9 | −105.2 |
| GLY 56 | −4.9 | 91.2 |
| LYS 57 | 127.9 | −60.6 |
| SER 58 | 148.5 | −97.5 |
| PHE 59 | 155.5 | −131.2 |
| SER 60 | −32.1 | −73.3 |

In one embodiment, the structural coordinates are within about 5.0 Å, such as about 4.5 Å, of the rmsd of the backbone atoms between each of the amino acid residues as listed in Table 1.

References to "Ramachandran angles" and "rmsd" are well known to a person skilled in the art. Ramachandran angles are used to describe the conformation of the peptide main chain. Two torsion angles in the polypeptide chain, also called Ramachandran angles, describe the rotations of the polypeptide backbone around the bonds between N-Cα (called Phi, φ) and Cα-C (called Psi, ψ), see Ramachandran et al. (1963) J. Mol. Biol., 7:95-99. Therefore, φ and ψ describe the rotation of the polypeptide chain around the two bonds on both sides of the Cα atom. The angles can be plotted in a Ramachandran plot to provide a way to view the distribution of torsion angles in a protein structure.

In bioinformatics, the root-mean-square deviation (rmsd) of atomic positions is the measure of the average distance between the atoms (usually the backbone atoms) of superimposed proteins. Typically, rmsd is used as a quantitative measure of similarity between two or more protein structures. The lower rmsd, the higher the similarity between two structures.

Determination of whether a structural motif falls within the rmsd of 5 Å from the motif shown in Table 1 would be well known to a person skilled in the art. Such calculation is carried out by the optimisation of the superposition of the coordinates of carbon alpha atoms of a given structural motif and the coordinates of those atoms in the structural motif contained in Table 1. Such optimisation will produce the minimum average rmsd of the two structural motifs. In the superposition referred to in the scope of this claim, carbon atoms on residues on both sides of the central glycine are to be considered equivalent and their rmsd values are the ones to be included in the calculation. Suitable protein modelling computer programs may be used in these calculations and are known in the art, for example *Molecular Operating Environment (MOE)*, 2013.08; Chemical Computing Group ULC.

In one embodiment, the ubiquitin targeting protein is derived from a zinc finger protein.

In one embodiment, the structural motif comprises an amino acid sequence of SEQ ID NO: 1:

$X_1X_2X_3X_4X_5GX_7X_8X_9X_{10}$ wherein X represents any amino acid or is absent. In a further embodiment, the structural motif of SEQ ID NO: 1 additionally comprises one, two, three or more amino acids. In a yet further embodiment, the structural motif comprises an amino acid sequence of SEQ ID NO: 15:

$X_1X_2X_3X_4X_5GX_7X_8X_9X_{10}X_{11}X_{12}$ wherein X represents any amino acid or is absent.

In one embodiment, one or more of the following apply:
$X_1$ represents valine (V), isoleucine (I) or is absent;
$X_2$ represents aspartic acid (D), asparagine (N) or is absent;
$X_3$ represents lysine (K), isoleucine (I) or is absent;
$X_4$ represents glutamine (Q), lysine (K) or threonine (T);
$X_5$ represents cysteine (C), serine (S) or asparagine (N);
$X_7$ represents alanine (A) or glutamic acid (E);
$X_8$ represents serine (S), lysine (K) or glutamic acid (E);
$X_9$ represents phenylalanine (F), serine (S) or valine (V);
$X_{10}$ represents threonine (T), lysine (K) or alanine (A);
$X_{11}$ represents glutamine (Q), threonine (T) or valine (V); and/or
$X_{12}$ represents lysine (K) or arginine (R).

In one embodiment, the structural motif is derived from a mammalian protein, such as a human protein.

In one embodiment, the structural motif is derived from Ikaros3, Ikaros1, Casein Kinase 1 alpha (CK1 alpha), Eukaryotic peptide chain release factor GTP-binding subunit ERF3A (GSTP1) or Zinc Finger Protein 91 (ZFP91). In a further embodiment, the structural motif is obtained from the Zinc Finger Nuclease 2 motif of Ikaros3. In an alternative embodiment, the structural motif is obtained from CK1 alpha. Sequence information for these proteins is available in the art, for example see UniProt ID numbers: Q9UKT9 for Ikaros3, P15170 for GSPT1, Q96JP5 for ZFP91 and P48729 for CK1 alpha. Structural information for these proteins is also available in the art, for example see PDB entries: 2MA7 or 2I13 which can be used as a structural representative for Ikaros3, 5HXB for GSTP1 and 5FQD for CK1 alpha.

In one embodiment, the structural motif comprises a sequence with at least 80%, 85%, 90%, 95% or 97% homology/identity to a sequence selected from the group consisting of: SEQ ID NO: 2, SEQ ID NO: 3, SEQ ID NO: 4 and SEQ ID NO: 5. In a further embodiment, the structural motif comprises a sequence with at least 80%, 85%, 90%, 95%, 97% or 99% identity to a sequence selected from the group consisting of: SEQ ID NO: 2, SEQ ID NO: 3 and SEQ ID NO: 4. In a yet further embodiment, the structural motif comprises a sequence with at least 80%, 85%, 90%, 95%, 97% or 99% identity to an amino acid sequence of SEQ ID NO: 2.

In one embodiment, the structural motif comprises a sequence selected from SEQ ID NO: 2, SEQ ID NO: 3, SEQ ID NO: 4, SEQ ID NO: 5 or a variant thereof. For example, the variant sequence may have up to 5, 4, 3, 2 or 1 amino acid substitution(s), addition(s) or deletion(s). Typically, the variation is a substitution, particularly a conservative substitution. The variant sequence may substantially retain the biological characteristics of the unmodified protein.

In one embodiment, the structural motif comprises a sequence selected from the group consisting of: SEQ ID NO: 2, SEQ ID NO: 3, SEQ ID NO: 4 and SEQ ID NO: 5. In a further embodiment, the structural motif comprises a sequence selected from the group consisting of: SEQ ID NO: 2, SEQ ID NO: 3 and SEQ ID NO: 4. In a yet further embodiment, the structural motif comprises an amino acid sequence of SEQ ID NO: 2.

In one embodiment, the ubiquitin targeting protein is a polypeptide sequence consisting of less than 130 amino acids in length, such as less than 125, 120, 115, 110, 105, 100, 90, 80, 70, 60 or 50 amino acids in length. In a further embodiment, the ubiquitin targeting protein is a polypeptide sequence consisting of less than 100 amino acids in length.

In one embodiment, the ubiquitin targeting protein comprises a ubiquitination bait, i.e. a sequence which comprises a lysine residue which can act as a ubiquitination site. This embodiment can be used, for example, when the polypeptide sequence does not itself contain a site suitable for ubiquitination, therefore a ubiquitination bait containing a ubiquitination site can be included within the ubiquitin targeting protein. In one embodiment, the ubiquitination site comprises a lysine residue.

In one embodiment, the ubiquitination bait comprises a sequence with at least 80%, 85%, 90%, 95% or 97% homology/identity to SEQ ID NO: 16. In one embodiment, the ubiquitination site comprises SEQ ID NO: 16 or a variant thereof. For example, the variant sequence may have up to 10, 9, 8, 7, 6, 5, 4, 3, 2 or 1 amino acid substitution(s), addition(s) or deletion(s). Typically, the variation is a substitution, particularly a conservative substitution. The variant sequence may substantially retain the biological characteristics of the unmodified protein.

In one embodiment, the ubiquitin targeting protein consists of a sequence selected from the group consisting of: SEQ ID NOs: 6-14 or functional fragments or functional variants thereof.

In one embodiment, the ubiquitin targeting protein consists of a sequence selected from the group consisting of: SEQ ID NOs: 6-14, 27 or functional fragments or functional variants thereof.

In one embodiment, the ubiquitin targeting protein consists of a sequence with at least 80%, 85%, 90%, 95%, 97% or 99% identity to a sequence selected from the group consisting of: SEQ ID NOs: 6-14. In one embodiment, the ubiquitin targeting protein consists of a sequence selected from the group consisting of: SEQ ID NOs: 6-14.

In one embodiment, the structural motif is derived from Ikaros3 and comprises SEQ ID NOs: 6, 7, 8, 9 or 10. In an alternative embodiment, the structural motif is derived from GSTP1 and comprises SEQ ID NOs: 11 or 12. In another alternative embodiment, the structural motif is derived from CK1 alpha and comprises SEQ ID NOs: 13 or 14.

If the structural motifs according to the invention are isolated from larger IMiD-dependent cereblon substrates, they may contain amino acid residues which form hydrophobic patches which can induce aggregation. Such patches can be mutated in order to attenuate any aggregation. Amino acids that are considered hydrophobic include: alanine (Ala), cysteine (Cys), valine (Val), leucine (Leu), isoleucine (Ile), phenylalanine (Phe), methionine (Met), tyrosine (Tyr) and tryptophan (Trp). If these residues are present in the hydrophobic patch they could be mutated to another type of amino acid residue, such as a neutral or hydrophilic residue, for examples serine (Ser), threonine (Thr), histidine (His), arginine (Arg), lysine (Lys), aspartic acid (Asp), glutamic acid (Glu), asparagine (Asn), glycine (Gly) proline (Pro) or glutamine (Gln), in order to minimise aggregation.

For example, the structure of GSTP1 in complex with cereblon and CC-885 (a cereblon modulator compound) was reported by Matyskiela et al. ((2016) Nature 535(7611): 252-257) and deposited by PDB entry 5HXB with data to 3.6 Å resolution. The C-terminal domain of GSTP1 (residues 388-499) could be isolated and used a degron as it contains the cereblon binding motif and an ubiquitination site. Therefore, in one embodiment, the structural motif may comprise SEQ ID NO: 11 (i.e. residues 388 to 499 of GSTP1).

The area exposed by removing the N-terminal domain is 385 Å$^2$ and the residues involved are:

TABLE 2

Exposed residues of GSTP1 upon removal of N-terminal domain

| Residue | Position | Surface Area in full length (Å2) | Surface Area as C terminal domain (Å2) | Residues in Hydrophobic Patch |
|---|---|---|---|---|
| HIS | 388 | 53.3 | 91.1 | |
| SER | 389 | 30.1 | 47.9 | |
| HIS | 417 | 47.6 | 80.5 | x |
| THR | 418 | 21.1 | 75.4 | |
| CYS | 419 | 12 | 34.1 | |
| ILE | 420 | 75.3 | 76.3 | |
| THR | 462 | 44.7 | 62.5 | |
| ILE | 463 | 25.4 | 32.5 | |
| CYS | 464 | 9.8 | 62.7 | |
| LEU | 465 | 9.5 | 10.8 | |
| GLU | 466 | 10.4 | 31.3 | |
| PHE | 471 | 36.5 | 72.9 | x |
| GLN | 473 | 41.1 | 73.4 | x |
| MET | 474 | 16.2 | 67.3 | x | where the residues in bold are involved in a hydrophobic patch of 90 Å$^2$. Therefore, residues His417, Phe471, Gln473 and/or Met474 can be mutated to polar or neutral residues, such as serine, in order to reduce the hydrophobic patch. In one embodiment, the structural motif comprises a variant of SEQ ID NO: 11 wherein residues His417, Phe471, Gln473 and/or Met474 are mutated to another amino acid, such as a neutral amino acid.

In one embodiment, the structural motif may comprise SEQ ID NO: 12 (i.e. residues 388 to 499 of GSTP1 with mutations F471S and M474S). In this embodiment, Gly437 represents the key central glycine and Lys493 acts as the ubiquitination site.

In another example, the structure of CK1 alpha in complex with cereblon and lenalidomide was reported by Petzold et al. ((2016) Nature 532(7597): 127-130) and deposited by PDB entry 5FQD with data to 2.45 Å resolution. Again, removal of the N-terminal and/or C-terminal domains will expose hydrophobic patches. In particular, residues Leu63, Leu67 and Ile73 are involved in a hydrophobic patch, therefore these could be candidates for mutations in order to reduce the area of the hydrophobic patch. Therefore, in one embodiment, the structural motif comprises a variant of SEQ ID NO: 13 wherein residues Leu63, Leu67 and/or Ile73 are mutated to another amino acid, such as a neutral amino acid. In a further embodiment, the structural motif may comprise SEQ ID NO: 14 (i.e. residues 8 to 94 of CK1 alpha with mutations L63H, L67Q and I73Q). In this embodiment, Gly40 represents the key central glycine and Lys62 and Lys65 act as ubiquitination sites.

In one embodiment, A is a polypeptide sequence that encodes a mammalian protein. In a further embodiment, the mammal is a human or a mouse.

In one embodiment, A encodes a polypeptide sequence that is not naturally found in the cell (i.e. a non-native protein).

In one embodiment, A encodes a chimeric antigen receptor (CAR) or a T cell receptor (TCR).

In one embodiment, the polypeptide sequence controlled by administering a compound which mediates binding of the ubiquitin targeting protein and cereblon encodes a mammalian protein. In a further embodiment, the mammal is a human or a mouse.

In one embodiment, the polypeptide sequence controlled by administering a compound which mediates binding of the ubiquitin targeting protein and cereblon encodes a protein not naturally found in the cell (i.e. a non-native protein).

In one embodiment, the polypeptide sequence controlled by administering a compound which mediates binding of the ubiquitin targeting protein and cereblon is a transmembrane protein.

In one embodiment, the polypeptide sequence controlled by administering a compound which mediates binding of the ubiquitin targeting protein and cereblon encodes a chimeric antigen receptor (CAR) or a T cell receptor (TCR).

Fusion proteins may be prepared using standard techniques known in the art, including chemical conjugation. For example, DNA sequences encoding the polypeptide components (A and B) may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

The fusion protein may additionally comprise a membrane-targeting domain so that the fusion protein is localised to the cell membrane. In one embodiment, the polypeptide sequence additionally comprises a membrane-targeting domain.

The membrane-targeting domain may be a chemical modification or particular protein sequence which attaches the molecule to the cell membrane. Therefore, in one embodiment, the membrane-targeting region is selected from: a myristoylation-targeting sequence, a palmitoylation-targeting sequence, a prenylation sequence (i.e., farnesylation, geranyl-geranylation, CAAX Box), a protein-protein interaction motif or a transmembrane sequence (e.g. from a receptor).

In one embodiment, the fusion protein is a genetic fusion. In an alternative embodiment, the fusion protein is generated using chemical conjugation, for example using conventional chemical cross-linkers which are used to fuse components A and B.

In one embodiment the fusion protein comprises the polypeptide sequence and a ubiquitin targeting protein consisting of less than 135 amino acids in length which comprises the hairpin motif of a cereblon binding site.

In one embodiment the fusion protein comprises the polypeptide sequence and a ubiquitin targeting protein, wherein the ubiquitin targeting protein consists of a sequence selected from the group consisting of: SEQ ID NOs: 6-14 and 27.

Immunomodulatory Imide Drugs

In one embodiment, the compound is an immunomodulatory imide drug (IMiD). Such drugs are class of immunomodulatory drugs containing an imide group. Currently, the primary use of IMiDs in the treatment of cancers and autoimmune diseases.

In one embodiment, the IMiD is thalidomide, lenalidomide or pomalidomide, or a functional derivative or analog thereof. In a further embodiment, the IMiD is selected from the group consisting of: thalidomide, lenalidomide and pomalidomide or a functional derivative or analog thereof.

Chimeric Antigen Receptors

According to a further aspect of the invention, there is provided a chimeric antigen receptor (CAR) comprising:
 an extracellular ligand binding domain;
 a transmembrane domain;
 an intracellular signalling domain; and,
 a ubiquitin targeting protein as described herein, which is capable of being bound by ubiquitin ligase in the presence of a compound.

In one embodiment, the ubiquitination targeting domain consists of a sequence selected from the group consisting of: SEQ ID NOs: 6-14 or functional fragments or functional variants thereof.

In one embodiment, the ubiquitination targeting domain consists of a sequence selected from the group consisting of: SEQ ID NOs: 6-14, 27 or functional fragments or functional variants thereof.

As described herein, the compound (e.g. an IMiD) is capable of binding to a ubiquitin ligase and enables the ubiquitin ligase to bind to the ubiquitin targeting protein, thereby bringing the chimeric antigen receptor into proximity of the ubiquitin ligase so that the chimeric antigen receptor is capable of being ubiquitinated. Once ubiquitinated, the chimeric antigen receptor may be degraded by a proteasome or its signalling activity may be impaired by the presence of the ubiquitin chain.

The CARs of the present invention include an intracellular ubiquitin targeting protein that may be bound by ubiquitin ligase in the presence of a compound. By including a ubiquitin targeting protein in the CAR construct, the CAR as expressed by the host cell can be readily and rapidly degraded upon exposure to a compound which mediates binding between the ubiquitin targeting protein and ubiquitin ligase and utilizes the ubiquitin proteasomal pathway to degrade the CAR. In this way, administering a compound targeting a ubiquitin targeting protein within a CAR allows for the modulation of the activation of the CAR expressing cell, as degradation of the CAR or a portion thereof within the CAR expressing cell prohibits activation signalling from occurring. This strategy can be utilized to modulate the activation of the CAR expressing cell, for example, to lessen the activation of the CAR expressing cell in order to reduce adverse inflammatory responses. Furthermore, by utilizing this strategy, the host cell is spared and just the CAR is degraded.

Furthermore, the use of the minimal degron as described herein, mean that it is less likely to interfere with the signalling of the CAR construct.

Standard chimeric antigen receptors are known in the art and generally comprise a target binding domain, a transmembrane domain and an intracellular effector domain.

The target binding domain (also referred to as the extracellular ligand binding domain) binds to a target, in particular wherein the target is a tumour specific molecule, viral molecule, or any other molecule expressed on a target cell population that is suitable to mediate recognition and elimination by a lymphocyte. In one embodiment, the target binding domain comprises an antibody, an antigen binding fragment or a ligand. In one embodiment, the target binding domain comprises an antibody or fragment thereof. In one embodiment, the target binding domain is a ligand (e.g. a natural ligand of the target antigen). In an alternative embodiment, the target binding domain is an antigen binding fragment. In a further embodiment, the antigen binding fragment is a single chain variable fragment (scFv) or a dAb. In a yet further embodiment, said scFv comprises the light (VL) and the heavy (VH) variable fragment of a target antigen specific monoclonal antibody joined by a flexible linker.

In one embodiment, the target binding domain may bind to more than one target, for example two different targets. Such a target binding domain may be derived from a bispecific single chain antibody. For example, Blinatumomab (also known as AMG 103 or MT103) is a recombinant CD19 and CD3 bispecific scFv antibody consisting of four immunoglobulin variable domains assembled into a single polypeptide chain. Two of the variable domains form the binding site for CD19 which is a cell surface antigen expressed on most normal and malignant B cells. The other two variable domains form the binding site for CD3 which is part of the T cell-receptor complex on T cells. These variable domains may be arranged in the CAR in tandem, i.e. two single chain antibody variable fragments (scFv) tethered to a spacer, and transmembrane and signalling domains. The four variable domains can be arranged in any particular order within the CAR molecule (e.g. VL(first target)-VH(first target)-VH(second target)-VL(second target) or VL(second target)-VH(second target)-VH(first target)-VL(first target) etc.), joined with any suitable linkers which are known in the art.

The target binding domain may bind a variety of cell surface antigens, but in one embodiment, the target binding domain binds to a tumour associated antigen. In a further embodiment, the tumour associated antigen is selected from: BCMA, carcinoembryonic antigen (CEA), cancer antigen-125, CA19-9, CD5, CD13, CD19, CD20, CD22, CD27, CD30, CD33, CD34, CD45, CD52, CD70, CD117, CD138, CD160, epidermal growth factor receptor (EGFR), folate binding protein, ganglioside G2 (GD2), HER2, mesothelin, MUC-1, neural cell adhesion molecule (NCAM), prostate stem cell antigen (PSCA), prostate-specific membrane antigen (PSMA), prostatic acid phosphatise (PAP), protein melan-A, synaptophysis, six transmembrane epithelial antigen of the prostate I (STEAP1), TARP, Trp-p8, tyrosinase or vimentin. In a yet further embodiment, the tumour associated antigen is BCMA.

In one embodiment the extracellular ligand binding domain is an anti-B Cell maturation antigen (BCMA) single chain Fv amino acid sequence.

In one embodiment the extracellular ligand binding domain is an anti-BCMA single chain Fv amino acid sequence which comprises SEQ ID NO: 29.

In one embodiment, the target binding domain has a binding affinity of less than about 500 nanomolar (nM), such as less than about 400 nM, 350 nM, 300 nM, 250 nM, 200 nM, 150 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 0.5 nM or 0.25 nM. In one embodiment, the target binding domain has a binding affinity of about 10 nM to about 0.25 nM. In a further embodiment, the target binding domain has a binding affinity of about 1 nM to about 0.5 nM (i.e. about 1000 pM to about 500 pM).

In one embodiment, the CAR additionally comprises a spacer domain between the target binding domain and the transmembrane domain. A spacer allows the target binding domain to orient in different directions to facilitate binding and can be used to improve the target binding interaction. In one embodiment, the spacer comprises a sequence derived from IgG (e.g. IgG1 Fc region or IgG1 hinge region), CD8 or CD4.

In one embodiment, the transmembrane domain can be derived either from a natural or from a synthetic source. In one embodiment, the transmembrane domain can be derived from any membrane-bound or transmembrane protein. Alternatively, the transmembrane domain can be synthetic and can comprise predominantly hydrophobic residues such as leucine and valine.

For example, the transmembrane domain can be the transmembrane domain of CD proteins, such as CD4, CD8, CD3 or CD28, a subunit of the T cell receptor, such as α, β, γ or δ, a subunit of the IL-2 receptor (a chain), or a subunit chain of Fc receptors. In one embodiment, the transmembrane domain comprises the transmembrane domain of CD4, CD8 or CD28. In a further embodiment, the transmembrane domain comprises the transmembrane domain of CD4 or CD8 (e.g. the CD8 alpha chain, as described in NCBI Reference Sequence: NP_001139345.1, incorporated herein by reference).

In one embodiment, the transmembrane domain comprises SEQ ID NO: 17.

The CAR may additionally comprise a hinge sequence next to the transmembrane domain (e.g. between the target binding domain and the transmembrane domain). Therefore, in one embodiment, the hinge sequence comprises SEQ ID NO: 18. In a further embodiment, the hinge and transmembrane domain comprise the complete sequence of SEQ ID NO: 19.

In some embodiments, the transmembrane domain is composed of the CD8a transmembrane helix immediately followed by the full length intracellular domain of 4-1BB which contains a stretch of sequence compatible with the membrane interface. If the domain next to the transmembrane domain does not have a sequence compatible with the membrane interface then a linker may be used.

Preferred examples of the intracellular effector domain for use in a CAR described herein, can be the cytoplasmic sequences of the natural T cell receptor and co-receptors that act in concert to initiate signal transduction following antigen binding, as well as any derivate or variant of these sequences and any synthetic sequence that has the same functional capability. These domains can be separated into two classes: those that initiate antigen-dependent primary activation, and those that act in an antigen-independent manner to provide a secondary or costimulatory signal. Primary activation effector domains can comprise signalling motifs which are known as immunoreceptor tyrosine-based activation motifs (ITAMs). ITAMs are well defined signalling motifs, commonly found in the intracytoplasmic tail of a variety of receptors, and serve as binding sites for syk/zap70 class tyrosine kinases. Examples of ITAMs used in the invention can include, as non-limiting examples, those derived from CD3zeta, FcRgamma, FcRbeta, FcRepsilon, CD3gamma, CD3delta, CD3epsilon, CD5, CD22, CD79a, CD79b and CD66d. In one embodiment, the intracellular effector domain comprises a CD3zeta signalling domain (also known as CD247). In a further embodiment, the CD3zeta signalling domain comprises SEQ ID NO: 20. This sequence is also found in Uniprot P20963, residues 51-164. Natural TCRs contain a CD3zeta signalling molecule, therefore the use of this effector domain is closest to the TCR construct which occurs in nature.

In one embodiment, the intracellular effector domain of the CAR comprises a CD3zeta signalling domain which has an amino acid sequence with at least 70%, preferably at least 80%, more preferably at least 85%, 90%, 95%, 97% or 99% sequence identity with SEQ ID NO: 20. In a further embodiment, the intracellular effector domain of the CAR comprises a CD3zeta signalling domain which comprises an amino acid sequence of SEQ ID NO: 20.

The CAR may also provide a secondary or costimulatory signal. T cells additionally comprise costimulatory molecules which bind to cognate costimulatory ligands on antigen presenting cells in order to enhance the T cell response, for example by increasing proliferation activation, differentiation and the like. Therefore, in one embodiment, the CAR additionally comprises a costimulatory domain. In a further embodiment, the costimulatory domain comprises the intracellular domain of a costimulatory molecule, selected from CD28, CD27, 4-1BB (CD137), OX40 (CD134), ICOS (CD278), CD30, CD40, PD-1 (CD279), CD2, CD7, NKG2C (CD94), B7-H3 (CD276) or any combination thereof. In a yet further embodiment, the costimulatory domain comprises the intracellular domain of a costimulatory molecule, selected from CD28, CD27, 4-1BB, OX40, ICOS or any combination thereof, in particular the intracellular domain of 4-1BB.

In one embodiment, the costimulatory domain comprises a 4-1BB signalling domain which has an amino acid sequence with at least 70%, preferably at least 80%, more preferably at least 85%, 90%, 95%, 97% or 99% sequence identity with SEQ ID NO: 21. In a further embodiment, the costimulatory domain comprises a 4-1BB signalling domain of SEQ ID NO: 21. This sequence is also found in Uniprot Q07011, residues 214-255. The advantage of using this costimulatory domain is that it contains a lysine residue which acts as a ubiquitination site (Lys219), therefore the ubiquitin targeting protein used with a CAR construct containing the 4-1BB costimulatory does not need to contain a ubiquitination site itself in order for ubiquitination to be induced.

It will be understood that the intracellular components on the CAR (i.e. the signalling domain, costimulatory domain and ubiquitin targeting protein) may be arranged in any order within the CAR construct, so long as they are located intracellularly. Therefore, in one embodiment the CAR construct comprises the domains in the following order: extracellular ligand binding domain—transmembrane domain—intracellular signalling domain—ubiquitin targeting protein; extracellular ligand binding domain—transmembrane domain—ubiquitin targeting protein—intracellular signalling domain; extracellular ligand binding domain—transmembrane domain—intracellular signalling domain—ubiquitin targeting protein—costimulatory domain; extracellular ligand binding domain—transmembrane domain—costimulatory domain—intracellular signalling domain—ubiquitin targeting protein; or extracellular ligand binding domain—transmembrane domain—costimulatory domain—ubiquitin targeting protein—intracellular signalling domain. In a further embodiment, the CAR construct comprises the domains in the following order: extracellular ligand binding domain—transmembrane domain—costimulatory domain—ubiquitin targeting protein—intracellular signalling domain.

In one embodiment the ubiquitin targeting protein is on the C-terminus of the CAR.

The nucleic acid sequence encoding the CAR may also comprise separator/linker sequences between one or more of the domains of the CAR construct. The linkers according to the invention may comprise alone, or in addition to other linkers, one or more sets of G, S or GS residues. In one embodiment, the linker comprises (GS)$_n$ and/or (GGGGS)$_p$ wherein n=1-10 and p=1-3. In one embodiment, the linker comprises GSGSGS (SEQ ID NO: 23), GSGSGSGSGS (SEQ ID NO: 24) or GGGGS (SEQ ID NO: 25).

According to a further aspect of the invention, there is provided a method of controlling the activity of a chimeric antigen receptor cell therapy comprising:

(a) transducing or transfecting an immunomodulatory cell with a polynucleotide encoding the chimeric antigen receptor as described herein;

(b) expressing said polynucleotide in the immunomodulatory cell;

(c) controlling the activation of the chimeric antigen receptor by the addition of a compound;

wherein the compound mediates binding of a) the ubiquitin targeting protein and b) a ubiquitin ligase in a manner that brings the chimeric antigen receptor into proximity of the ubiquitin ligase, wherein the chimeric antigen receptor, in the presence of the compound, is capable of being ubiquitinated.

Without being bound by theory, addition of the compound is thought to lead to degradation of the CAR, thereby reducing (i.e. switching off) the CAR level and activity. By degrading at least a portion of the CAR, the ability of the CAR to activate the immune effector cell, for example a CAR T-cell, is diminished. As contemplated herein, sufficient degradation of the CAR occurs wherein the CAR's signalling functionality is disrupted. Alternatively, the attachment of a polyubiquitin chain could cause steric hindrance which leads to reduced activity through steric inhibition.

Signal Peptides

The components of the fusion protein described herein may comprise a signal peptide so that when a component is expressed in a cell, the nascent protein is directed to the endoplasmic reticulum and subsequently to the cell surface where it may be expressed.

The core of the signal peptide may contain a long stretch of hydrophobic amino acids that has a tendency to form a single alpha helix. The signal peptide may begin with a short positively charged stretch of amino acids which helps to enforce proper topology of the polypeptide during translocation. At the end of the signal peptide there is typically a stretch of amino acids that is recognized and cleaved by signal peptidase. Signal peptidase may cleave either during or after completion of translocation to generate free signal peptide and a mature protein. The free signal peptides are then digested by specific proteases. The signal peptide may be at the amino terminus of the molecule.

In one embodiment, the signal peptide is derived from CD8 (see UniProt P01732). In a further embodiment, the signal peptide comprises SEQ ID NO: 22 or a variant thereof having 5, 4, 3, 2 or 1 amino acid mutations (insertions, deletions, substitutions or additions) provided that the signal peptide still functions to cause cell surface expression of the component (i.e. a functional variant).

Polynucleotides and Expression Vectors

According to a further aspect of the invention, there is provided an isolated polynucleotide encoding the ubiquitin targeting protein described herein. According to a further aspect of the invention, there is provided a polynucleotide encoding the fusion protein described herein. According to a yet further aspect of the invention, there is provided a polynucleotide encoding the chimeric antigen receptor described herein.

The polynucleotide sequences described herein may be codon optimised. The degeneracy found in the genetic code allows each amino acid to be encoded by between one and six synonymous codons allowing many alternative nucleic acid sequences to encode the same protein (Gustafsson et al. (2004) *Trends Biotechnol.* 22(7): 346-53). Codon optimisation is a technique used to modify genetic sequences with the intent of increasing the rate of expression of a gene in a heterologous expression system; typically, the nucleotide sequence encoding a protein of interest is codon optimized such that the codon usage more closely resembles the codon bias of the host cell, while still coding for the same amino acid sequence.

Nucleic acids described herein may comprise DNA or RNA. They may be single-stranded or double-stranded. They may also be polynucleotides which include within them synthetic or modified nucleotides. A number of different types of modification are well known in the art, such as methylphosphonate and phosphorothioate backbones, or addition of acridine or polylysine chains. Such modifications can be used in order to enhance in vivo activity or life span of the polynucleotides of the present invention.

The polynucleotide may be present in an expression cassette or expression vector (e.g. a plasmid for introduction into a bacterial host cell, or a viral vector such as a lentivirus for transfection of a mammalian host cell). Therefore, according to a further aspect of the invention, there is provided an expression vector comprising any of the polynucleotides described herein.

The term "vector" refers to a vehicle which is able to artificially carry foreign genetic material into another cell, where it can be replicated and/or expressed. In one embodiment, the vector is a plasmid, a viral vector, a transposon based vector or a synthetic mRNA.

In one embodiment, the expression vector is a retroviral vector. In a further embodiment, the retroviral vector is derived from, or selected from, a lentivirus, alpha-retrovirus, gamma-retrovirus or foamy-retrovirus, such as a lentivirus or gamma-retrovirus, in particular a lentivirus. In a further embodiment, the retroviral vector particle is a lentivirus selected from the group consisting of HIV-1, HIV-2, SIV, FIV, EIAV and Visna. Lentiviruses are able to infect non-dividing (i.e. quiescent) cells which makes them attractive vectors for gene therapy. In a yet further embodiment, the retroviral vector particle is HIV-1 or is derived from HIV-1. The genomic structure of some retroviruses may be found in the art. For example, details on HIV-1 may be found from the NCBI Genbank (Genome Accession No. AF033819). HIV-1 is one of the best understood retroviruses and is therefore often used as a viral vector.

Host Cells

According to a further aspect of the invention, there is provided a cell comprising the fusion protein described herein. According to another aspect of the invention, there is provided a cell comprising a polynucleotide or expression vector as described herein.

In one embodiment, the cell is an immunomodulatory cell. The term "immunomodulatory cell" refers to a cell of hematopoietic origin functionally involved in the modulation (e.g. the initiation and/or execution) of the innate and/or adaptive immune response. Said immunomodulatory cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Said immunomodulatory cell can also be a dendritic cell, a killer dendritic cell, a mast cell, a NK-cell, a B-cell or a T-cell. The T-cell may be selected from the group consisting of inflammatory T-lymphocytes, cytotoxic T-lymphocytes, regulatory T-lymphocytes or helper T-lymphocytes, or a combination thereof. Therefore, in one embodiment, the immunomodulatory cell is derived from an inflammatory T-lymphocyte, cytotoxic T-lymphocyte, regulatory T-lymphocyte or helper T-lymphocyte. In another embodiment, said cell can be derived from the group consisting of $CD4^+$ T-lymphocytes and $CD8^+$ T-lymphocytes.

In one embodiment, the immunomodulatory cell may be a human immunomodulatory cell.

In one embodiment, the immunomodulatory cell is allogeneic or autologous. It will be understood that "autologous" refers to cells obtained from the patient themselves, whereas "allogeneic" refers to cells obtained from a donor. Autologous cells have the advantage that they are compatible with the patient and therefore avoid any immunological compatibility problems leading to graft-versus-host disease (GvHD). In order to prevent the allogeneic cells from being rejected by the patient, they would either need to be derived from a compatible donor or modified to ensure no antigens are present on the cell surface which would initiate an unwanted immune response.

Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor or a diseased donor, such as a patient diagnosed with cancer or an infection. In another embodiment, said cell is part of a mixed population of cells which present different phenotypic characteristics.

The immunomodulatory cells may be activated and/or expanded prior to being transduced with polynucleotides or expression vectors encoding the fusion protein described herein. For example, the cells may be treated with an anti-CD3 monoclonal antibody to cause activation.

It will be understood that the immunomodulatory cells may express the fusion protein described herein transiently or stably/permanently (depending on the transfection method used and whether the polynucleotide encoding the fusion protein has integrated into the immunomodulatory cell genome or not).

After introduction of the fusion protein, the immunomodulatory cells may be purified.

Uses

The invention described herein provides for the use of a minimal ubiquitin targeting protein as part of a safety switch. Therefore, according to an aspect of the invention there is provided the use of the ubiquitin targeting protein described herein as a safety switch.

In one embodiment, the safety switch is used in a gene therapy (or method thereof). In a further embodiment, the gene therapy is a cellular gene therapy.

As described herein, the term "safety switch" refers to a biochemical mechanism that can be activated on demand in order to control a biological process which can cause harm. Therefore, in one embodiment, the safety switch is used to control the signalling of a chimeric antigen receptor (CAR) or heterologous T-cell receptor (TCR).

In one embodiment, the TCR is genetically modified. In a further embodiment, the T cell receptors affinity is changed to an affinity and/or specificity normally not present in said receptors natural surroundings. In a yet further embodiment, the T cell receptor's affinity is changed to an affinity for a self-antigen, a tumour antigen and/or a pathogen derived antigen.

According to a further aspect of the invention, there is provided the cell described herein for use in therapy. In one embodiment, therapy comprises administration of the cell to a human subject in need of such therapy.

According to a further aspect of the invention, there is provided the use of the fusion protein described herein, in a method of gene therapy.

In one embodiment, the therapy is adoptive cellular therapy. "Adoptive cellular therapy" (or "adoptive immunotherapy") refers to the adoptive transfer of human T lymphocytes that are engineered by gene transfer to express CARs or TCRs specific for surface molecules expressed on target cells. This can be used to treat a range of diseases depending upon the target chosen, e.g. tumour specific antigens to treat cancer. Adoptive cellular therapy involves removing a portion of the patient's white blood cells using a process called leukapheresis. The T cells may then be expanded and mixed with expression vectors described herein in order to permanently transfer the fusion protein to the T cells. The T cells are expanded again and at the end of the expansion, the T cells are washed, concentrated, and then frozen to allow time for testing, shipping and storage until the patient is ready to receive the infusion of engineered T cells.

Pharmaceutical Compositions

According to a further aspect of the invention, there is provided a pharmaceutical composition comprising a plurality of cells as defined herein. In one embodiment the cells comprise a polynucleotide sequence encoding the polypeptide sequence and a ubiquitin targeting protein consisting of less than 135 amino acids in length which comprises the hairpin motif of a cereblon binding site. In one embodiment the cells comprise an expression vector encoding the polypeptide sequence and a ubiquitin targeting protein consisting of less than 135 amino acids in length which comprises the hairpin motif of a cereblon binding site. In one embodiment the cells comprising a polynucleotide sequence or expression vector encoding the polypeptide sequence and a ubiquitin targeting protein consisting of less than 135 amino acids in length which comprises the hairpin motif of a cereblon binding site are immunomodulatory cells. In one embodiment the cells comprising a polynucleotide sequence or expression vector encoding the polypeptide sequence and a ubiquitin targeting protein consisting of less than 135 amino acids in length which comprises the hairpin motif of a cereblon binding site are T-cells.

Examples of additional pharmaceutical composition ingredients include, without limitation, any adjuvants, carriers, excipients, glidants, sweetening agents, diluents, preservatives, dyes/colourants, flavour enhancers, surfactants, wetting agents, dispersing agents, suspending agents, stabilizers, isotonic agents, solvents, surfactants, emulsifiers, buffers (such as phosphate buffered saline (PBS)), carbohydrates (such as glucose, mannose, sucrose or dextrans), amino acids, antioxidants or chelating agents (such as EDTA or glutathione).

In one embodiment, the pharmaceutical composition additionally comprises a pharmaceutically acceptable excipient, carrier, or diluent. The carrier, excipient or diluent must be "acceptable" in the sense of being compatible with the other ingredients of the composition and not deleterious to the recipient thereof. According to the present invention any excipient, vehicle, diluents or additive used would have to be compatible with the fusion protein described herein. Standard texts known in the art, such as "Remington's Pharmaceutical Science", 17th Edition, 1985, incorporated herein by reference, may be consulted to prepare suitable preparations.

Pharmaceutical compositions may be administered by injection or continuous infusion (examples include, but are not limited to, intravenous, intratumoural, intraperitoneal, intradermal, subcutaneous, intramuscular and intraportal). In one embodiment, the composition is suitable for intravenous administration. When administering a therapeutic composition of the present invention (e.g., a pharmaceutical composition containing a genetically modified cell as described herein), it will generally be formulated in a unit dosage injectable form (solution, suspension, emulsion). Pharmaceutical compositions may be suitable for topical administration (which includes, but is not limited to, epicutaneous, inhaled, intranasal or ocular administration) or enteral administration (which includes, but is not limited to, oral or rectal administration).

Methods for the preparation of such pharmaceutical compositions are well known to those skilled in the art. Other excipients may be added to the composition as appropriate for the mode of administration and the particular protein used.

Effective doses and treatment regimens for administering the composition of the present invention may be dependent on factors such as the age, weight and health status of the patient and disease to be treated. Such factors are within the purview of the attending physician.

According to a further aspect of the invention, there is provided a pharmaceutical composition as defined herein, for use in the treatment or prevention of a disease.

In one embodiment, the disease is selected from: a cancer, a pathogenic immune response and an infection.

According to a further aspect of the invention, there is provided the use of a pharmaceutical composition as described herein, in the manufacture of a medicament for the treatment and/or prevention of a disease.

Kits

According to a further aspect of the invention, there is provided a kit which comprises the fusion protein, chimeric antigen receptor, polynucleotide, expression vector, cell and/or pharmaceutical composition as described herein.

Methods

According to a further aspect of the invention, there is provided a method of engineering an immunomodulatory cell (i.e. to express the fusion protein described herein), comprising:

(a) providing an immunomodulatory cell;

(b) transducing or transfecting the polynucleotide or the expression vector as defined herein, into said immunomodulatory cell; and (c) expressing said polynucleotide or said expression vector in the immunomodulatory cell.

In one embodiment, the immunomodulatory cell is obtained from a sample isolated from a patient (i.e. autologous). In an alternative embodiment, the immunomodulatory cell is obtained from a donor (i.e. allogeneic).

As a non-limiting example, the fusion protein can be introduced as a transgene encoded by an expression vector as described herein. The expression vector can also contain a selection marker which provides for identification and/or selection of cells which received said vector.

Polypeptides may be synthesized in situ in the cell as a result of the introduction of polynucleotides encoding said fusion protein into the cell. Alternatively, said polypeptides could be produced outside the cell and then introduced thereto. Methods for introducing a polynucleotide construct into cells are known in the art and including, as non-limiting examples, stable transformation methods wherein the polynucleotide construct is integrated into the genome of the cell or transient transformation methods wherein the polynucleotide construct is not integrated into the genome of the cell and virus mediated methods. Said polynucleotides may be introduced into a cell by, for example, recombinant viral vectors (e.g. retroviruses, adenoviruses), liposomes and the like. For example, transient transformation methods include for example microinjection, electroporation or particle bombardment. The polynucleotides may be included in vectors, more particularly plasmids or viruses, in view of being expressed in cells.

The terms "transfection", "transformation" and "transduction" as used herein, may be used to describe the insertion of the expression vector into the target cell. Insertion of a vector is usually called transformation for bacterial cells and transfection for eukaryotic cells, although insertion of a viral vector may also be called transduction. The skilled person will also be aware of the different non-viral transfection methods commonly used, which include, but are not limited to, the use of physical methods (e.g. electroporation, cell squeezing, sonoporation, optical transfection, protoplast fusion, impalefection, magnetofection, gene gun or particle bombardment), chemical reagents (e.g. calcium phosphate, highly branched organic compounds or cationic polymers) or cationic lipids (e.g. lipofection). Many transfection methods require the contact of solutions of plasmid DNA to the cells, which are then grown and selected for a marker gene expression.

Once the fusion protein has been introduced into the immunomodulatory cell, said cell may be referred to as a "transduced cell". Therefore, according to a further aspect of the invention, there is provided a cell obtained by the method described herein. Also within the scope of the present invention is a cell line obtained from a transduced cell according to the method described herein.

According to a further aspect of the invention, there is provided a method of inhibiting a CAR system in a subject which comprises the immunomodulatory cells defined herein, which comprises administering to the subject a compound which mediates binding between the ubiquitin targeting protein and a ubiquitin ligase. Such a compound would bring the CAR into proximity of the ubiquitin ligase so that the CAR is capable of being ubiquitinated. The ubiquitinated CAR can then degraded by a proteasome.

The level of CAR signalling by the system described herein, may be adjusted by altering the amount of compound present, or the amount of time the compound is present. Therefore, in one embodiment, the level of CAR cell activation may be increased by decreasing the dose of compound administered to the subject or decreasing the frequency of its administration. In an alternative embodiment, the level of CAR cell activation may be reduced by increasing the dose of the compound, or the frequency of administration to the subject.

Without being bound by theory, higher levels of CAR signalling are likely to be associated with reduced disease progression but potentially increased toxic activities, whilst lower levels of CAR signalling are likely to be associated with increased disease progression but potentially reduced toxic activities.

According to a further aspect of the invention, there is provided a method of treating and/or preventing a disease, which comprises administering to a subject the cell or the pharmaceutical composition as defined herein.

In one embodiment, the disease is cancer. In a further embodiment, the cancer is selected from: blood, bone marrow, lymph, lymphatic system, bladder, breast, colon, cervix, esophagus, kidney, large intestine, lung, oral cavity, ovary, pancreas, prostate, rectum, skin or stomach. In a yet further embodiment, the cancer is a blood cancer, for example selected from the group consisting of: B cell leukaemia, multiple myeloma (MM), acute lymphoblastic leukaemia (ALL), chronic lymphocytic leukaemia (CLL) and non-Hodgkin's lymphoma.

When the method described herein is used to treat cancer, in one embodiment, the method reduces the number of tumour cells, reduces the tumour size and/or eradicates the tumour in the subject.

In one embodiment, the disease is a pathogenic immune response, such as an autoimmune disease, allergy or graft-versus-host rejection. Autoimmune diseases arise from an abnormal immune response of the body against substances and tissues normally present in the body. This can result in the damage or destruction of tissues, or altered organ growth or function. Examples of autoimmune diseases include, but are not limited to: diabetes mellitus Type 1, arthritis (including juvenile, psoriatic, reactive, and rheumatoid arthritis), psoriasis, multiple sclerosis, vasculitis, alopecia areata, pernicious anaemia, glomerulonephritis, autoimmune hepatitis, autoimmune pancreatitis, ulcerative colitis, systemic lupus erythematosus, Graves' disease, Guillain-Barré syndrome, Sjogren's syndrome, Celiac disease, Crohn's disease and Wegener's syndrome.

In one embodiment, the disease is an infection. An infection can be caused by a pathogen, such as a bacteria, virus, parasite, protozoa or fungi. In a further embodiment, the infection is a viral or bacterial infection.

In one embodiment, the subject is a mammal. In a further embodiment, the mammal is selected from the group consisting of: a human, a mouse, a primate, a cow, a pig, a horse, a sheep, a cat, and a dog. In a yet further embodiment, the subject is a human.

The method of treatment and/or prevention, may comprise the following steps:

(a) providing a cell(s);
(b) transducing or transfecting the polynucleotide or the expression vector as defined herein, into said cell(s);
(c) expressing said polynucleotide or said expression vector in the cell(s); and
(d) administering the cell(s) to a patient.

In one embodiment, the method additionally comprises:
(e) administering a compound which mediates binding between the ubiquitin targeting protein and a ubiquitin ligase. This can be used to control the level and/or activity of the polypeptide sequence expressed by said polynucleotide or said expression vector. The compound may be administered to the patient before or simultaneously with the polynucleotide or the expression vector (i.e. prior to or during step (d) in the method of treatment steps outlined above). In the context of a CAR as described herein, administration of the compound before/simultaneously with the polypeptide/expression vector allows the CAR to be administered in an "inactive" or a "lowly active" (i.e. OFF) state. The amount of agent can then be decreased in order to activate the CAR. Administering the CAR in its inactive state allows for an even distribution of the immunomodulatory cells to be achieved, therefore preventing local accumulation of activated cells.

Alternatively, the compound may be administered to the patient after administration of the polynucleotide or the expression vector (i.e. after step (d) in the method of treatment steps outlined above) so that the CAR is administered in its "active" (i.e. ON) state.

The cells or pharmaceutical compositions described herein may be administered to a patient who already has the disease in order to lessen, reduce or improve at least one symptom associated with the disease and/or to slow down, reduce or block the progression of the disease (i.e. therapeutically). The cells or pharmaceutical compositions described herein may be administered to a patient who has not yet contracted the disease and/or who is not showing any symptoms of the disease to prevent the cause of the disease (i.e. prophylactically). The patient may have a predisposition for, or be thought to be at risk of developing the disease.

The compound may be administered in the form of a pharmaceutical composition. In this embodiment, the composition may additionally comprise pharmaceutically acceptable carriers, diluents or excipients as outlined herein.

The present invention provides a suitable OFF switch to be used with CAR-T cell therapies. The method may involve monitoring toxic activity in the patient. Thus, if the level of toxic activity becomes too high, the method can involve administering a compound enables ubiquitin ligase to bind to the ubiquitin targeting protein and thus ubiquitinate the polypeptide sequence/CAR, in order to reduce adverse toxic side effects. Toxic activities include, for example, immunological toxicity, biliary toxicity and respiratory distress syndrome.

Similarly, the method may involve monitoring the progression of disease and then administering a compound which mediates binding between the ubiquitin targeting protein and a ubiquitin ligase, and thus ubiquitinate the polypeptide sequence/CAR, when an acceptable level of disease progression is reached (e.g. amelioration). The specific level of disease progression determined to be "acceptable" will vary according to the specific circumstances and should be assessed on such a basis.

Monitoring the progression of the disease means to assess the symptoms associated with the disease over time to determine if they are reducing/improving or increasing/worsening.

According to a further aspect of the invention, there is provided a compound for inhibiting the CAR as defined herein.

The invention may be described in more detail with reference to the following, non-limiting examples:

Example 1: Design of Chimeric Antigen Receptors that Incorporate Cereblon Binding Motifs as a Strategy to Build a Molecular Off-Switch Constructs have been designed to build a chimeric antigen receptor off-switch using the cereblon binding motifs present in human cereblon targets such as Ikaros3, Casein kinase 1 alpha and GSTP1. Such constructs aim to 1) be degraded by the addition of small molecules such as lenalidomide b) signal as chimeric antigen receptors by the activation of the NFAT pathway in the absence of compound and c) be turned off by the addition of compounds.

Experiments have been designed to measure the degradation of GFP proteins containing Ikaros3 ZnF cereblon binding regions and the observed structural conservation on the cereblon binding sites of three protein substrates Ikaros3 ZNF2, CK1 alpha and GSTP1:

TABLE 3

Cereblon binding sites

| Substrate | UniProt ID | Structural reference (PDB entries) |
|---|---|---|
| Ikaros3 ZNF2 | Q9UKT9 | PDB entries 2MA7 and 2I13 will be used as structural representatives of Ikaros3 ZnF: 2MA7 with sequence identity of 95% when aligned to Ikaros 3 residues 131-175 (SEQ ID NO: 8) and 2I13 with sequence identity of 53% when aligned to Ikaros 3 residues 131-175 (SEQ ID NO: 8). 2I13 will be used as a model of Ikaros3 as the structure is represented by a single experimental model. |
| GSTP1 | P15170 | 5HXB |
| CK1 alpha | P48729 | 5FQD |

Structural conservation of the cereblon binding sites in the three substrates: Ikaros3, casein kinase I and GSTP1, was observed. However, this was in the absence of sequence conservation (see SEQ ID NOs: 2-4). When the three hairpin motifs from the substrates are superposed using main chain atoms the overall rmsd is around 1.7 Å:

TABLE 4

Pairwise RMSD Matrix

| Chains | GSTP1 | CK1 alpha | Ikaros3 (from 2I13) |
|---|---|---|---|
| GSTP1 | | 2.04 | 1.81 |
| CK1 alpha | 2.04 | | 1.38 |
| Ikaros3 (from 2I13) | 1.81 | 1.38 | |

The closest structural overlap is seen around a central Glycine residue and the rmsd starts to increase as the residues are located farther away from the central glycine, in particular on the C-terminal direction:

TABLE 5

Individual residue RMSD

| GSTP1 vs CK1 | | GSTP1 vs Ikaros3 | | CK1 vs Ikaros3 | |
|---|---|---|---|---|---|
| Pair | rmsd | Pair | rmsd | Pair | rmsd |
| ILE 35 - VAL 570: | 0.758 | LYS 51 - VAL 570: | 0.595 | LYS 51 - ILE 35: | 0.348 |
| ASN 36 - ASP 571: | 0.629 | CYS 52 - ASP 571: | 0.65 | CYS 52 - ASN 36: | 0.386 |
| ILE 37 - LYS 572: | 0.166 | PRO 53 - LYS 572: | 0.608 | PRO 53 - ILE 37: | 0.556 |
| THR 38 - LYS 573: | 0.22 | GLU 54 - LYS 573: | 0.328 | GLU 54 - THR 38: | 0.443 |
| ASN 39 - SER 574: | 0.435 | CYS 55 - SER 574: | 0.429 | CYS 55 - ASN 39: | 0.37 |
| GLY 40- GLY 575: | 0.208 | GLY 56 - GLY 575: | 0.63 | GLY 56 - GLY 40: | 0.426 |
| GLU 41 - GLU 576: | 0.245 | LYS 57 - GLU 576: | 0.562 | LYS 57 - GLU 41: | 0.39 |
| GLU 42 - LYS 577: | 0.477 | SER 58 - LYS 577: | 0.431 | SER 58 - GLU 42: | 0.051 |
| VAL 43 - SER 578: | 0.733 | PHE 59 - SER 578: | 0.974 | PHE 59-VAL 43: | 0.947 |
| ALA 44 - LYS 579: | 4.683 | SER 60 - LYS 579: | 4.139 | SER 60-ALA 44: | 2.335 |
| ALA 44 - LYS 579: | 4.683 | ASP 61 - THR 580: | 3.15 | ASP 61-VAL 45: | 2.624 |
| LYS 46 - ARG 581: | 5.507 | LYS 62 - ARG 581: | 6.03 | LYS 62-LYS 46: | 4.847 |

An alternative representation of the structural similarity is the Ramachandran angles as they describe the conformation of the peptide main-chain. When Ramachandran angles are measured in these cereblon binding motifs we have (central glycine is highlighted in bold):

TABLE 6

Ramachandran angles of cereblon binding hairpin motifs

| CK1 | | | GSTP1 | | | Ikaros3 (2MA7) | | |
|---|---|---|---|---|---|---|---|---|
| Residue | Psi | Phi | Residue | Psi | Phi | Residue | Psi | Phi |
| ILE 35 | 129.7 | −125.5 | VAL 570 | 132.4 | −149.2 | LYS 51 | 151.5 | −102.8 |
| ASN 36 | 106.9 | −70.6 | ASP 571 | 141 | −82.1 | CYS 52 | 127.8 | −83.5 |
| ILE 37 | −14.2 | −60.3 | LYS 572 | −42.5 | −79.4 | PRO 53 | −7.5 | −66 |
| THR 38 | −18.3 | −89.2 | LYS 573 | −47.1 | −52.6 | GLU 54 | −52.5 | −111.7 |
| ASN 39 | −3 | −152 | SER 574 | −65.9 | −90.8 | CYS 55 | −16.9 | −105.2 |
| GLY 40 | −4.3 | 91.8 | GLY 575 | −4.8 | 123.6 | GLY 56 | −4.9 | 91.2 |
| GLU 41 | 131.7 | −56.5 | GLU 576 | 104.1 | −75.1 | LYS 57 | 127.9 | −60.6 |
| GLU 42 | 133.3 | −96.6 | LYS 577 | 169 | −52.5 | SER 58 | 148.5 | −97.5 |
| VAL 43 | 169.4 | −136.4 | SER 578 | 168.1 | −108.3 | PHE 59 | 155.5 | −131.2 |
| ALA 44 | 139.7 | −106.3 | LYS 579 | −59.1 | −91.6 | SER 60 | −32.1 | −73.3 |
| VAL 45 | 112 | −127.1 | THR 580 | 169.3 | −86.4 | ASP 61 | 161.1 | −132.6 |
| LYS 46 | 125.4 | −87.9 | ARG 581 | 156.7 | −64.6 | LYS 62 | −35.3 | −69 |

Direct comparison of the differences can be facilitated by calculation of the modulus of the differences in the angles, so if the difference is 0 the conformation is identical and the higher positive values the higher is the overall difference in conformation. The pairwise comparison of the Ramachandran angles differences (delta) represented as the modulus of the angle difference (angle 1-angle 2) is shown in Table 7:

TABLE 7

Comparison between Ramachandran angles

| Residue | CK1 vs GSTP1 | | CK1 vs Ikaros | | GSTP1 vs Ikaros | |
|---|---|---|---|---|---|---|
| | delta Psi | delta Phi | delta Psi | delta Phi | delta Psi | delta Phi |
| −5 | 2.7 | 23.7 | 21.8 | 22.7 | 19.1 | 46.4 |
| −4 | 34.1 | 11.5 | 20.9 | 12.9 | 13.2 | 1.4 |
| −3 | 28.3 | 19.1 | 6.7 | 5.7 | 35 | 13.4 |
| −2 | 28.8 | 36.6 | 34.2 | 22.5 | 5.4 | 59.1 |
| −1 | 62.9 | 61.2 | 13.9 | 46.8 | 49 | 14.4 |
| 1 (Gly) | 0.5 | 31.8 | 0.6 | 0.6 | 0.1 | 32.4 |
| 2 | 27.6 | 18.6 | 3.8 | 4.1 | 23.8 | 14.5 |
| 3 | 35.7 | 44.1 | 15.2 | 0.9 | 20.5 | 45 |
| 4 | 1.3 | 28.1 | 13.9 | 5.2 | 12.6 | 22.9 |
| 5 | 198.8 | 14.7 | 171.8 | 33 | 27 | 18.3 |
| 6 | 57.3 | 40.7 | 49.1 | 5.5 | 8.2 | 46.2 |
| 7 | 31.3 | 23.3 | 160.7 | 18.9 | 192 | 4.4 |

Residue 1 is the central Glycine residue. In this comparison, it is clear the conformational similarity of CK1 and Ikaros3 around residues 1 to 4 with Psi angles differences <20° and Phi angles differences <5°. Comparison of both CK1 and Ikaros3 with GSTP1 in this region shows the same conformational trend but with higher variations of the angles with Psi variations <35° and Phi variations <45°. In all cases, the structural differences become apparent around position 5 and this is in agreement with the rmsd differences.

Based on data available and structural analysis it is proposed that the 2nd zinc finger of Ikaros3 should provide a "minimal" degron in the form of a small protein domain (around 30 amino acids) that can be added to a protein of interest for degradation and in the presence of an immunomodulatory imide drug (IMiD) degradation will be induced. This degron/ubiquitin targeting protein can therefore be incorporated into CAR architecture using methods known in the art in order to create a CAR construct with an "off" switch".

Example 2. Proximity Induced Degradation of Green Fluorescent Protein (GFP) Protein Fused to Ikaros 1 Derived Degron Sequences in HeLa Cells This example illustrates the selective degradation of GFP in the presence of lenalidomide. GFP constructs are composed of GFP coding sequence in frame with a (Glycine-Serine)×N linker of lengths N=1, 3, 5 followed by a degron sequence derived from human Ikaros 1. Experiments were conducted with constructs transfected in HeLa cells and degradation was followed by flow cytometry.

Materials and Methods

Figure 2:
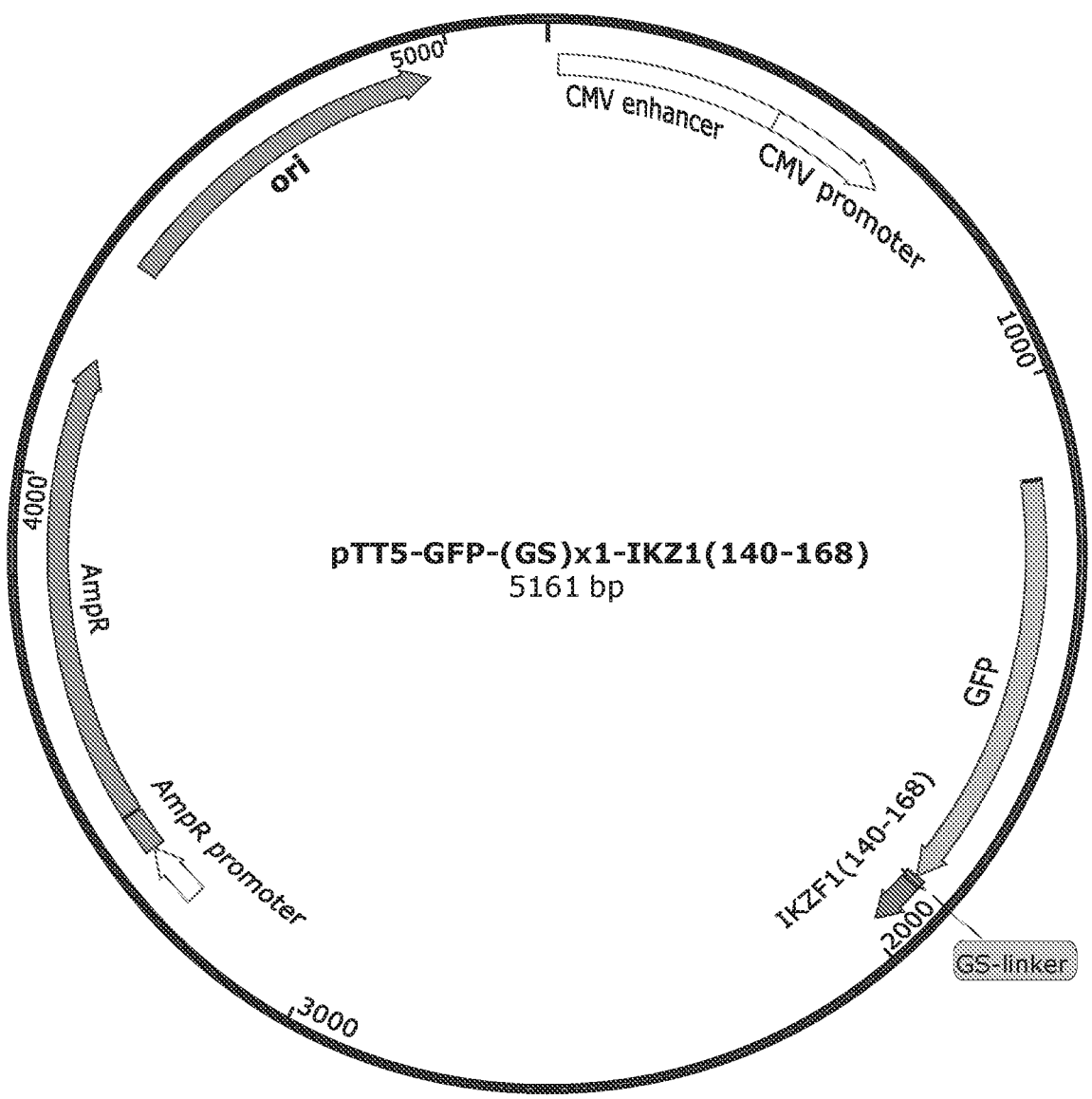
FIG. 2. Plasmid map encoding GFP fused to degron signal derived from human Ikaros 1 protein (Uniprot Q13422).

Generation of Constructs:

GFP constructs were cloned into pTT5 vector (FIG. 2) fused to a (Glycine-Serine)×N linker of length N=1, 3, 5 and human Ikaros 1 (IKFZ1, Uniprot Q13422) sequence containing residues 141 to 168 (SEQ ID NO:27). Full sequence details of the constructs are given below.

CONSTURCT 1
(SEQ ID NO 30)
MSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFF
KDDGNYKTRAVKFEGDTLVNRIELKGIDFKEDGNILGHKLEYNYNSHNVY
IMADKQKNGIKVNFKIRHNIEDGSVQLADHYQQNTPIGDGPVLLPDNHYL
STQSALSKDPNEKRDHMVLLEFVTAAGITLGMDELYKGSGERPFQCNQCG
ASFTQKGNLLRHIKLHS

Legend:
GFP

Linker 4 (SEQ ID NO 26)

Ikaros 1 residues 141-168 (Uniprot Q13422)
(SEQ ID NO 27)

CONSTRUCT 1 DNA sequence
(SEQ ID NO 31)
ATGAGCAAGGGCGAGGAGCTGTTCACCGGGGTGGTGCCCATCCTGGTCGA
GCTGGACGGCGACGTAAACGGCCACAAGTTCAGCGTGTCCGGCGAGGGCG
AGGGCGATGCCACCTACGGCAAGCTGACCCTGAAGTTCATCTGCACCACC
GGCAAGCTGCCCGTGCCCTGGCCCACCCTCGTGACCACCCTGACCTACGG
CGTGCAGTGCTTCAGCCGCTACCCCGACCACATGAAGCAGCACGACTTCT
TCAAGTCCGCCATGCCCGAAGGCTACGTCCAGGAGCGCACCATCTTCTTC
AAGGACGACGGCAACTACAAGACCCGCGCCGAGGTGAAGTTCGAGGGCGA
CACCCTGGTGAACCGCATCGAGCTGAAGGGCATCGACTTCAAGGAGGACG
GCAACATCCTGGGGCACAAGCTGGAGTACAACTACAACAGCCACAACGTC
TATATCATGGCCGACAAGCAGAAGAACGGCATCAAGGTGAACTTCAAGAT
CCGCCACAACATCGAGGACGGCAGCGTGCAGCTCGCCGACCACTACCAGC
AGAACACCCCCATCGGCGACGGCCCCGTGCTGCTGCCCGACAACCACTAC
CTGAGCACCCAGTCCGCCCTGAGCAAAGACCCCAACGAGAAGCGCGATCA
CATGGTCCTGCTGGAGTTCGTGACCGCCGCCGGGATCACTCTCGGCATGG
ACGAGCTGTACAAGGGTTCAGGAGAACGGCCCTTCCAGTGCAATCAGTGC
GGGGCCTCATTCACCCAGAAGGGCAACCTGCTCCGGCACATCAAGCTGCA
TTCC CONSTRUCT 2
(SEQ ID NO 32)
MSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFF
KDDGNYKTRAEVKFEGDTLVNRIELKGIDFKEDGNILGHKLEYNYNSHNV
YIMADKQKNGIKVNFKIRHNIEDGSVQLADHYQQNTPIGDGPVLLPDNHY
LSTQSALSKDPNEKRDHMVLLEFVTAAGITLGMDELYKGSGSGSGERPFQ
CNQCGASFTQKGNLLRHIKLHS Legend:
GFP
Linker 1 (SEQ ID NO 23)

Ikaros 1 residues 141-168 (Uniprot Q13422)
(SEQ ID NO 27)

CONSTRUCT 2 DNA sequence
(SEQ ID NO 33)
ATGAGCAAGGGCGAGGAGCTGTTCACCGGGGTGGTGCCCATCCTGGTCGA

GCTGGACGGCGACGTAAACGGCCACAAGTTCAGCGTGTCCGGCGAGGGCG

AGGGCGATGCCACCTACGGCAAGCTGACCCTGAAGTTCATCTGCACCACC

GGCAAGCTGCCCGTGCCCTGGCCCACCCTCGTGACCACCCTGACCTACGG

CGTGCAGTGCTTCAGCCGCTACCCCGACCACATGAAGCAGCACGACTTCT

TCAAGTCCGCCATGCCCGAAGGCTACGTCCAGGAGCGCACCATCTTCTTC

AAGGACGACGGCAACTACAAGACCCGCGCCGAGGTGAAGTTCGAGGGCGA

CACCCTGGTGAACCGCATCGAGCTGAAGGGCATCGACTTCAAGGAGGACG

GCAACATCCTGGGGCACAAGCTGGAGTACAACTACAACAGCCACAACGTC

TATATCATGGCCGACAAGCAGAAGAACGGCATCAAGGTGAACTTCAAGAT

CCGCCACAACATCGAGGACGGCAGCGTGCAGCTCGCCGACCACTACCAGC

AGAACACCCCCATCGGCGACGGCCCCGTGCTGCTGCCCGACAACCACTAC

CTGAGCACCCAGTCCGCCCTGAGCAAAGACCCCAACGAGAAGCGCGATCA

CATGGTCCTGCTGGAGTTCGTGACCGCCGCCGGGATCACTCTCGGCATGG

ACGAGCTGTACAAGGGTTCAGGTTCAGGTTCAGGAGAACGGCCCTTCCAG

TGCAATCAGTGCGGGGCCTCATTCACCCAGAAGGGCAACCTGCTCCGGCA

CATCAAGCTGCATTCC

CONSTRUCT 3
(SEQ ID NO 34)
MSKGEELFTGVVPILVELDGDVNGHKFSVSGEGEGDATYGKLTLKFICTT

GKLPVPWPTLVTTLTYGVQCFSRYPDHMKQHDFFKSAMPEGYVQERTIFF

KDDGNYKTRAEVKFEGDTLVNRIELKGIDFKEDGNILGHKLEYNYNSHNV

YIMADKQKNGIKVNFKIRHNIEDGSVQLADHYQQNTPIGDGPVLLPDNHY

LSTQSALSKDPNEKRDHMVLLEFVTAAGITLGMDELYKGSGSGSGSGSGE

RPFQCNQCGASFTQKGNLLRHIKLHS

Legend:
GFP
Linker 2 (SEQ ID NO 24)

Ikaros 1 residues 141-168 (Uniprot Q13422)
(SEQ ID NO 27)

CONSTRUCT 3 DNA sequence
(SEQ ID NO 35)
ATGAGCAAGGGCGAGGAGCTGTTCACCGGGGTGGTGCCCATCCTGGTCGA

GCTGGACGGCGACGTAAACGGCCACAAGTTCAGCGTGTCCGGCGAGGGCG

AGGGCGATGCCACCTACGGCAAGCTGACCCTGAAGTTCATCTGCACCACC

GGCAAGCTGCCCGTGCCCTGGCCCACCCTCGTGACCACCCTGACCTACGG

CGTGCAGTGCTTCAGCCGCTACCCCGACCACATGAAGCAGCACGACTTCT

TCAAGTCCGCCATGCCCGAAGGCTACGTCCAGGAGCGCACCATCTTCTTC

AAGGACGACGGCAACTACAAGACCCGCGCCGAGGTGAAGTTCGAGGGCGA

CACCCTGGTGAACCGCATCGAGCTGAAGGGCATCGACTTCAAGGAGGACG

GCAACATCCTGGGGCACAAGCTGGAGTACAACTACAACAGCCACAACGTC

TATATCATGGCCGACAAGCAGAAGAACGGCATCAAGGTGAACTTCAAGAT

CCGCCACAACATCGAGGACGGCAGCGTGCAGCTCGCCGACCACTACCAGC

AGAACACCCCCATCGGCGACGGCCCCGTGCTGCTGCCCGACAACCACTAC

CTGAGCACCCAGTCCGCCCTGAGCAAAGACCCCAACGAGAAGCGCGATCA

CATGGTCCTGCTGGAGTTCGTGACCGCCGCCGGGATCACTCTCGGCATGG

ACGAGCTGTACAAGGGTTCAGGTTCAGGTTCAGGTTCAGGAGAA

CGGCCCTTCCAGTGCAATCAGTGCGGGGCCTCATTCACCCAGAAGGGCAA

CCTGCTCCGGCACATCAAGCTGCATTCC

Transfection of HeLa Cells with CONSTRUCTS 1, 2 and 3 and Lenalidomide Treatment:

HeLa Ohio cells grown in EMEM (EBSS)+2 mM Glutamine+1% Non-Essential Amino Acids (NEAA)+10% Foetal Bovine Serum (FBS) supplemented with 10% heat inactivated foetal bovine serum (Gibco) and 50 U/mL penicillin+50 µg/mL streptomycin (Gibco) were transfected with 0.5 µg of construct plasmid using Lipofectamine 2000 reagent (Thermofisher). After transfection, cells were incubated at 37° C. in a $CO_2$ incubator for 24 hours. lenalidomide was reconstituted to 10 mM in 100% DMSO and diluted to 1 mM, 0.5 mM, 0.1 mM and 0.05 mM in 100% DMSO. lenalidomide was added to the cell medium to a final concentration of 10 µM, 1 µM, 0.5 µM, 0.1 µM, and 0.01 µM and the corresponding DMSO amount for the no compound control. The final DMSO concentration in all conditions was 0.1%. After lenalidomide treatment, cells were incubated at 37° C., 5% $CO_2$ for 24 hours. GFP expression was measured by flow cytometry with an iQue (Intellicyt) and data analysed using ForeCyt (Intellicyt).

Results

Lenalidomide induced degradation of GFP encoded in CONSTRUCTS 1, 2 and 3 was assessed by measurement of the median fluorescence intensity (MFI) of GFP positive cells.

Figure 3:
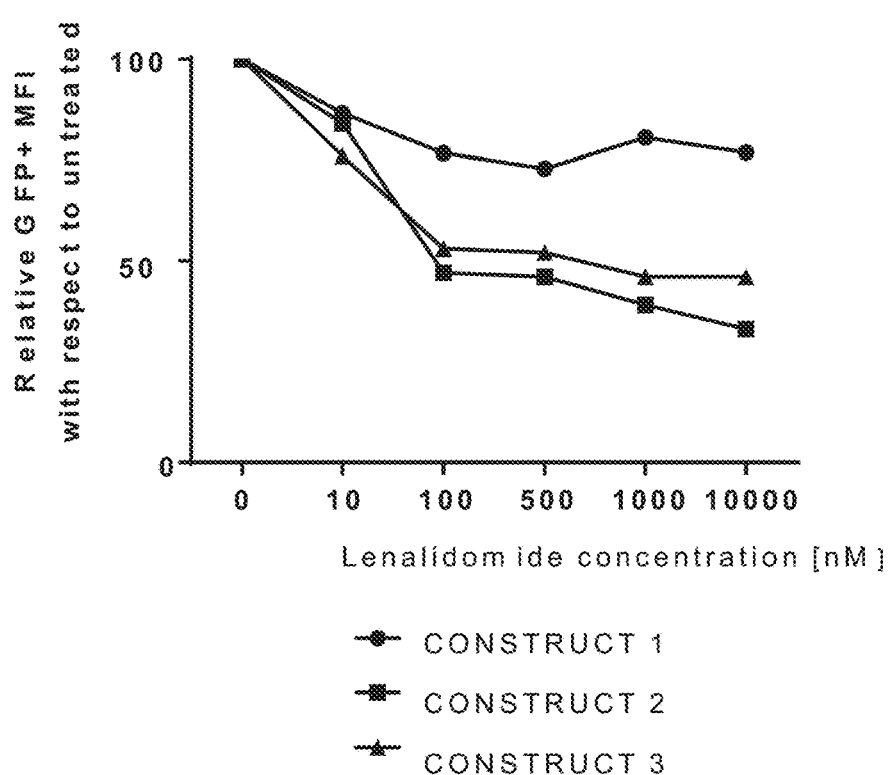
FIG. 3. Effect of lenalidomide treatment on the expression levels of Green Fluorescent Protein (GFP) fused with degrons in HEK293T cells. (A) Table with the values of median fluorescence intensity of GFP positive cells treated with increasing amount of lenalidomide. Constructs included in the figure differ only in the length of the (Glycine-Serine)×N linker between GFP and the degron sequence, with CONSTRUCT 1 N=1, CONSTRUCT 2 N=3 and CONSTRUCT 3 N=5. (B) Median fluorescence intensity (MFI) values relative to untreated (no lenalidomide) values.
Figure 4:
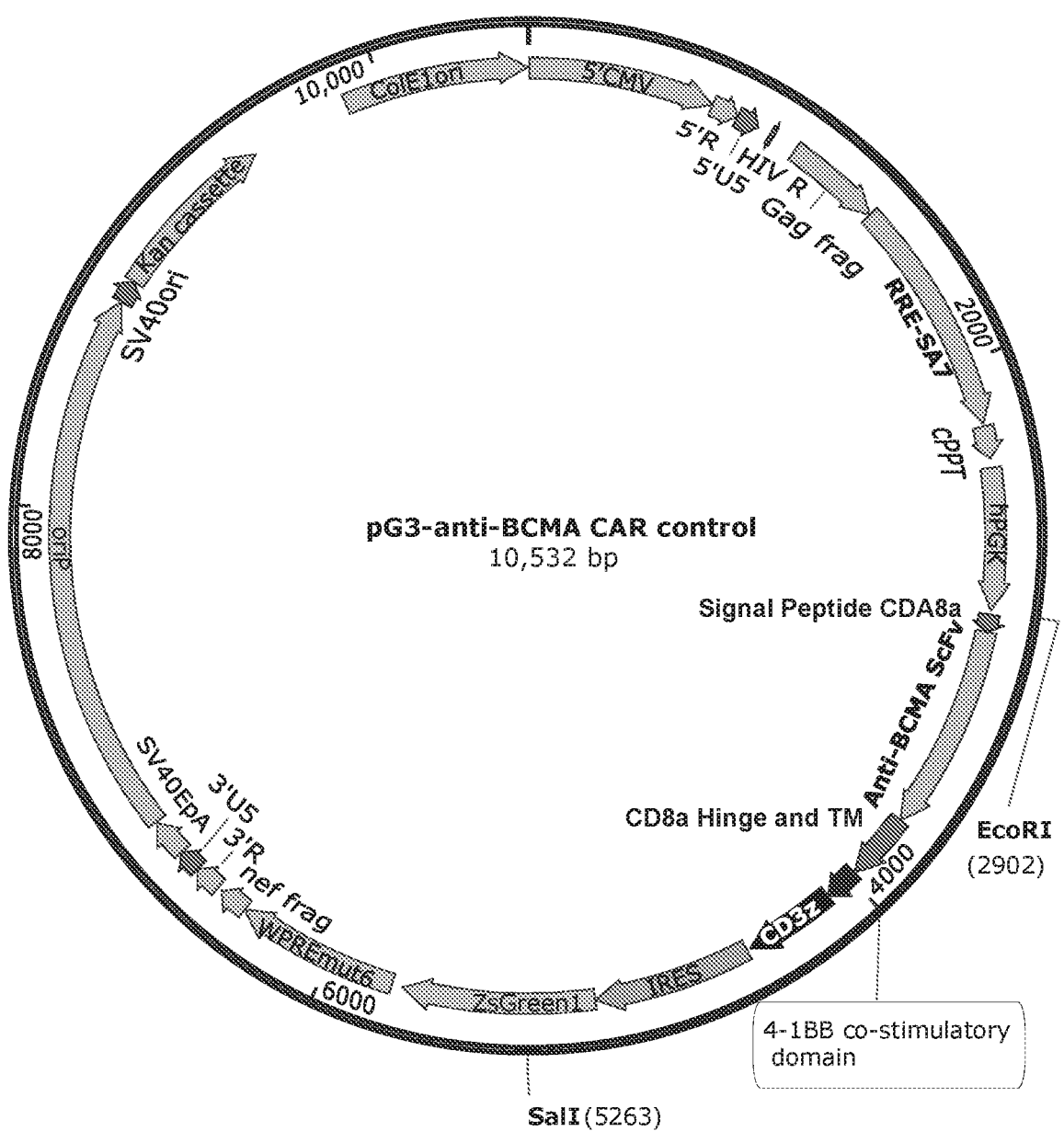
FIG. 4. Plasmid map encoding chimeric antigen receptor (CAR) construct used as a control for lenalidomide induced CAR degradation. ZsGreen used as a reporter for transfection/transduction.

The effect of lenalidomide on the expression level of GFP is displayed on FIG. 3.

Example 3: Proximity Induced Degradation of Chimeric Antigen Receptor (CAR) Constructs Transfected in Jurkat Cells This example illustrates the selective degradation of CAR constructs in the presence of lenalidomide. Experiments were conducted by transfection of the CAR constructs in Jurkat cells.

Materials and Methods

Generation of Constructs:

Two constructs were generated to evaluate the effect of lenalidomide on the regulation of the expression levels of a receptor (CAR). CONSTRUCT 4 is a conventional CAR with an antigen recognition scFv that binds to and is activated by the B-cell maturation antigen BCMA (Uniprot Q02223). The scFv is followed by human CD8a hinge and transmembrane domain, human 4-1BB co-stimulatory and the human CD3 intracellular domains (FIG. 1). CONSTRUCT 5 contains the same elements of CONSTRUCT 4 plus the C-terminal end addition of two sections of the human Ikaros 3 protein (Uniprot Q9UKT9). The first section comprises residues 131-175 (SEQ ID NO:27) and is followed by a section containing residues 231-249 (SEQ ID NO: 28). Full sequence details of the constructs are given below.

CONSTRUCT 4
(SEQ ID NO 36)
MALPVTALLLPLALLLHAARPQVQLVQSGAEVKKPGSSVKVSCKGSYTF
TNYWMHWVRQAPGQGLEWIGATYRGHSDTYYNQKFKGRATLTADTSTSTA
YMELSSLRSEDTAVYYCTRGAIYDGYDVLDNWGQGTLVTVSSGGGGSGGG
GSGGGGSGGGGSDIQMTQSPSSLSASVGDRVTITCSASQDISNYLNWYQQ
KPGKAPKLLIYYTSNLHSGVPSRFSGSGSGTDFTLTISSLQPEDFATYYC
QQYRKLPWTFGQGTKLEIKRFVPVFLPAKPTTTPAPRPPTPAPTIASQPL
SLRPEACRPAAGGAVHTRGLDFACDIYIWAPLAGTCGVLLLSLVITLYCN
HRNKRGRKKLLYIFKQPFMRPVQTTQEEDGCSCRFPEEEEGGCELRVKFS
RSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALH
MQALPPR

Legend:
CD8α (Uniprot P01732) signal peptide
(SEQ ID NO 22)
Anti-BCMA single chain Fv (SEQ ID NO 29)

CD8α (Uniprot P01732) hinge and transmembrane
region (SEQ ID NO 19)

4-1BB costimulatory domain (SEQ ID NO 21)

CD3ζ (Uniprot P20963) domain (SEQ ID NO 20)

CONSTRUCT 4 DNA Sequence
(SEQ ID NO 37)
ATGGCCCTGCCCGTGACCGCCCTCCTGCTGCCCCTGGCCCTGCTGCTGCA
CGCCGCCAGGCCCCAGGTCCAGCTGGTGCAGAGCGGGGCCGAGGTGAAGA
AGCCCGGCAGCTCCGTGAAAGTGAGCTGCAAGGGCAGCGGCTACACCTTC
ACCAACTACTGGATGCACTGGGTGAGGCAGGCCCCCGGACAGGGACTGGA
GTGGATCGGCGCCACCTACAGGGGCCACAGCGACACCTACTACAACCAGA
AGTTCAAGGGCAGGGCCACCCTGACCGCCGACACTAGCACCAGCACCGCC
TACATGGAACTGAGCTCACTGCGGAGCGAGGACACCGCCGTGTACTACTG
CACCAGGGGCGCCATCTACGACGGCTACGACGTGCTGGACAACTGGGGCC
AGGGCACCCTGGTGACAGTGAGCTCTGGCGGCGGCGGGAGCGGCGGCGGC
GGAAGCGGCGGCGGAGGAAGCGGCGGCGGCGGAAGCGATATCCAGATGAC
CCAGAGCCCCAGCAGCCTGAGCGCCAGCGTGGGCGACAGGGTGACCATCA
CCTGCAGCGCAAGCCAGGACATCAGCAACTACCTGAACTGGTACCAGCAG
AAGCCCGGCAAGGCCCCTAAGCTGCTGATCTACTACACCTCTAACCTGCA
CAGCGGCGTGCCCAGCAGGTTCTCTGGCAGCGGCTCCGGCACCGACTTCA
CTCTGACCATCAGCAGCCTCCAGCCCGAGGACTTCGCCACCTACTACTGC
CAGCAGTACAGGAAGCTCCCCTGGACCTTCGGCCAGGGCACCAAGCTGGA
GATCAAGCGCTTCGTGCCCGTGTTCCTCCCCGCAAAACCCACCACCACTC
CCGCCCCCAGACCCCCCACTCCCGCCCCAACAATTGCCAGCCAGCCCCTG
AGCCTGAGGCCCGAGGCTTGTAGGCCCGCCGCTGGCGGCGCCGTCCACAC
CAGGGGCCTGGACTTCGCCTGCGACATCTATATCTGGGCCCCCCTGGCCG GAACCTGCGGCGTGCTGCTGCTGAGCCTGGTGATCACCCTGTACTGCAAC
CACAGGAACAAGAGGGGCAGGAAGAAGCTCCTGTACATCTTCAAGCAGCC
CTTCATGAGGCCCGTGCAGACCACCCAGGAGGAGGACGGCTGCAGCTGCA
GGTTCCCAGAGGAAGAGGAGGGCGGGTGCGAACTGAGAGTGAAATTTAGC
AGGAGCGCCGACGCCCCCGCCTATCAGCAAGGCCAGAACCAGCTGTACAA
CGAGCTCAACCTGGGCAGGAGGGAGGAGTACGACGTGCTGGACAAGCGGA
GGGGCAGAGATCCCGAGATGGGCGGCAAGCCCAGGAGGAAGAATCCCCAG
GAGGGCCTGTACAACGAGCTGCAGAAGGACAAGATGGCCGAGGCCTACAG
CGAGATCGGCATGAAGGGGGAGAGGAGGAGGGGCAAGGGCCACGACGGCC
TGTACCAGGGCCTGAGCACCGCCACCAAGGACACCTACGACGCCCTGCAC
ATGCAGGCCCTGCCCCCCAGG CONSTUCT 5
(SEQ ID NO 38)
MALPVTALLLPLALLLHAARPQVQLVQSGAEVKKPGSSVKVSCKGSYTF
TNYWMHWVRQAPGQGLEWIGATYRGHSDTYYNQKFKGRATLTADTSTSTA
YMELSSLRSEDTAVYYCTRGAIYDGYDVLDNWGQGTLVTVSSGGGGSGGG
GSGGGGSGGGGSDIQMTQSPSSLSASVGDRVTITCSASQDISNYLNWYQQ
KPGKAPKLLIYYTSNLHSGVPSRFSGSGSGTDFTLTISSLQPEDFATYYC
QQYRKLPWTFGQGTKLEIKRFVPVFLPAKPTTTPAPRPPTPAPTIASQPL
SLRPEACRPAAGGAVHTRGLDFACDIYIWAPLAGTCGVLLLSLVITLYCN
HRNKRGRKKLLYIFKQPFMRPVQTTQEEDGCSCRFPEEEEGGCELGGGGS
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPRGGGGSNVLMVHKRSHTGERPFQCNQCGASFTQKGNLLR
HIKLHTGEKPFKDPGDTASAEARHIKAEMG

Legend:
CD8α (Uniprot P01732) signal peptide (SEQ ID NO 22)
Anti-BCMA single chain Fv (SEQ ID NO 29)

CD8α (Uniprot P01732) hinge and transmembrane
region (SEQ ID NO 19)

4-1BB costimulatory domain (SEQ ID NO 21)

CD3ζ (Uniprot P20963) domain (SEQ ID NO 20)

Linker 3 (SEQ ID NO 25)

Ikaros 3 residues 131-175 (Uniprot Q9UKT9)
(SEQ ID NO 8)
Ikaros 3 residues 231-249 (Uniprot Q9UKT9)
(SEQ ID NO 28)
CONSTRUCT 5 DNA sequence
(SEQ ID NO 39)
ATGGCTCTTCCTGTAACCGCACTTCTGCTTCCTCTTGCTCTGCTGCTTCA
TGCTGCTAGACCTCAGGTGCAGTTAGTGCAATCTGGAGCTGAGGTGAAGA
AACCTGGCTCTTCCGTGAAAGTGAGCTGTAAGGGAAGCGGCTACACCTTT
ACCAACTACTGGATGCATTGGGTGAGACAGGCCCCTGGACAGGGATTAGA
GTGGATTGGAGCCACATATAGAGGACACAGCGATACCTACTACAACCAGA -continued

```
AGTTCAAGGGCAGGGCCACCCTTACAGCCGATACAAGCACATCTACCGCC

TACATGGAACTGTCTTCTCTGAGAAGCGAGGATACCGCCGTGTACTACTG

CACAAGAGGAGCCATCTACGACGGCTATGATGTTCTGGACAATTGGGGAC

AGGGCACACTGGTGACAGTGTCTTCTGGTGGTGGCGGGTCCGGTGGAGGC

GGATCTGGCGGTGGGGGCTCCGGAGGAGGAGGTTCAGATATTCAAATGAC

ACAGAGCCCAAGCAGCCTGTCTGCTTCTGTGGGCGATAGAGTGACCATCA

CCTGTTCTGCTTCTCAGGATATCAGCAACTACCTGAACTGGTACCAGCAG

AAGCCCGGCAAAGCCCCTAAACTGCTGATCTACTACACCAGCAATCTGCA

CTCTGGAGTTCCTAGCAGATTCAGCGGAAGCGGCTCTGGCACCGATTTTA

CACTGACCATCTCTTCTCTGCAGCCTGAGGATTTTGCCACCTACTACTGC

CAGCAGTACCGGAAATTGCCTTGGACCTTTGGACAGGGAACCAAGCTGGA

GATCAAGAGGTTTGTGCCCGTGTTTCTGCCTGCTAAGCCTACAACAACAC

CTGCCCCTAGACCACCTACACCTGCTCCTACAATTGCCTCTCAGCCTCTT

TCTCTGAGACCTGAAGCTTGCAGACCTGCTGCTGGAGGAGCTGTGCATAC

AAGAGGACTGGATTTTGCCTGCGATATCTACATTTGGGCTCCACTGGCCG

GCACATGTGGAGTTCTTCTGCTGTCTCTGGTGATCACCCTGTACTGTAAT

CACAGGAACAAGCGGGGCCGGAAAAAGCTGCTGTACATCTTCAAGCAGCC

CTTCATGAGACCAGTTCAGACAACACAGGAGGAGGACGGCTGTAGCTGCA

GATTTCCTGAGGAAGAGGAAGGAGGATGTGAATTAGGTGGTGGCGGGAGC

AGGGTGAAGTTCTCACGCAGCGCAGATGCTCCTGCCTATCAGCAAGGCCA

GAATCAGCTGTACAACGAGCTGAATCTGGGCAGAAGAGAGGAGTACGATG

TGCTGGACAAGAGAAGGGGCAGAGATCCTGAAATGGGAGGAAAGCCCAGA

AGGAAGAACCCTCAAGAAGGCCTGTACAATGAGCTGCAGAAGGACAAGAT

GGCCGAGGCCTATAGCGAGATTGGCATGAAAGGAGAGAGGAGAAGAGGAA

AGGGCCATGATGGCCTGTATCAGGGCCTGTCTACAGCCACCAAGGATACA

TATGATGCCCTGCATATGCAGGCTTTACCCCCTAGAGGAGGAGGCGGATC

TAACGTGCTGATGGTGCATAAAAGAAGCCACACAGGAGAGAGACCATTCC

AGTGCAACCAGTGTGGAGCCAGCTTCACCCAGAAGGGAAATCTGCTGAGA

CACATCAAACTGCATACAGGCGAGAAGCCCTTCAAGGACCCTGGCGATAC

AGCCTCTGCTGAAGCTAGACACATTAAAGCCGAAATGGGC
```

Expression of Constructs in Jurkat Cells:

NFAT-luc2 Jurkat cells (Promega) to a density of $2 \times 10^5$ cells/ml were cultured in RPMI medium 1640 (1×) without L-glutamine with phenol red (Gibco), 10% (v/v) Fetal Bovine Serum (FBS) Heat-Inactivated (Gibco), 1% (v/v) Minimum essential medium non-essential amino acids (MEM NEAA) (ThermoFisher), 1% (v/v) Sodium Pyruvate (Sigma), 1% (v/v) L-Glutamine (Gibco). 20 μg of plasmid DNA was mixed with $8 \times 10^6$ NFAT-luc2 Jurkat cells and cells were transfected using the 4D-Nucleofector (Lonza) with cell Line SE Nucleofector kit (Lonza) by following manufacturer instructions with program CL-120. Cells were incubated at 37° C. with 5% $CO_2$ for 48 h. Lenalidomide at a stock concentration of 10 mM in 100% DMSO was diluted in Jurkat media to achieve a stock concentration of 250 μM. Using the 250 μM stock, NFAT-luc2 Jurkat cells were incubated at a final compound concentration of 10 μM or 0 μM (DMSO in media) for 24 hour at 37° C. with 5% $CO_2$. Final DMSO concentration was 0.1% in all wells. Cells were then stained with AlexaFluor 647 conjugated BCMA-Fc to label the anti-BCMA CAR. Measurements were made using a Cytoflex S (Beckman Coulter) and data analysed using FlowJo.

Results

Figure 5:
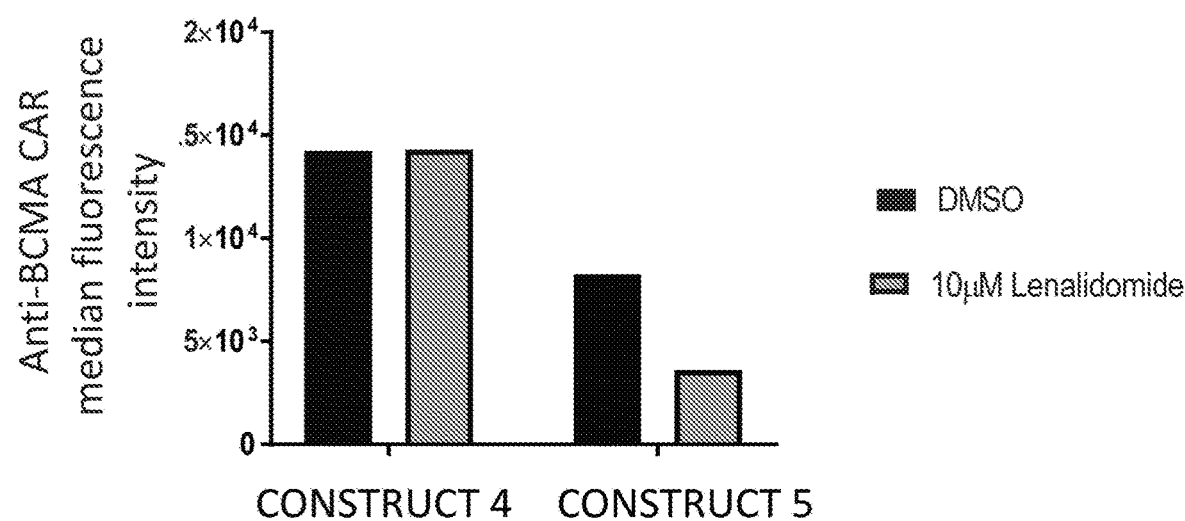
FIG. 5. Effect of lenalidomide treatment on the expression levels of anti-BCMA CARs fused with degrons in Jurkat cells. (A) Median fluorescence intensity of anti-BCMA-CAR constructs in transfected (ZsGreen positive) Jurkat cells after treatment with DMSO or 10 μM lenalidomide. CONSTRUCT 4 represents a CAR without a degron signal while CONSTRUCT 5 contains that same elements of CONSTRUCT 4 plus sequences derived from human Ikaros 3 (Uniprot Q9UKT9) protein. (B) Flow cytometry histograms of the Jurkat cells in (A), showing the effect of DMSO and 10 μM lenalidomide on anti-BCMA CAR expression.
Figure 5:
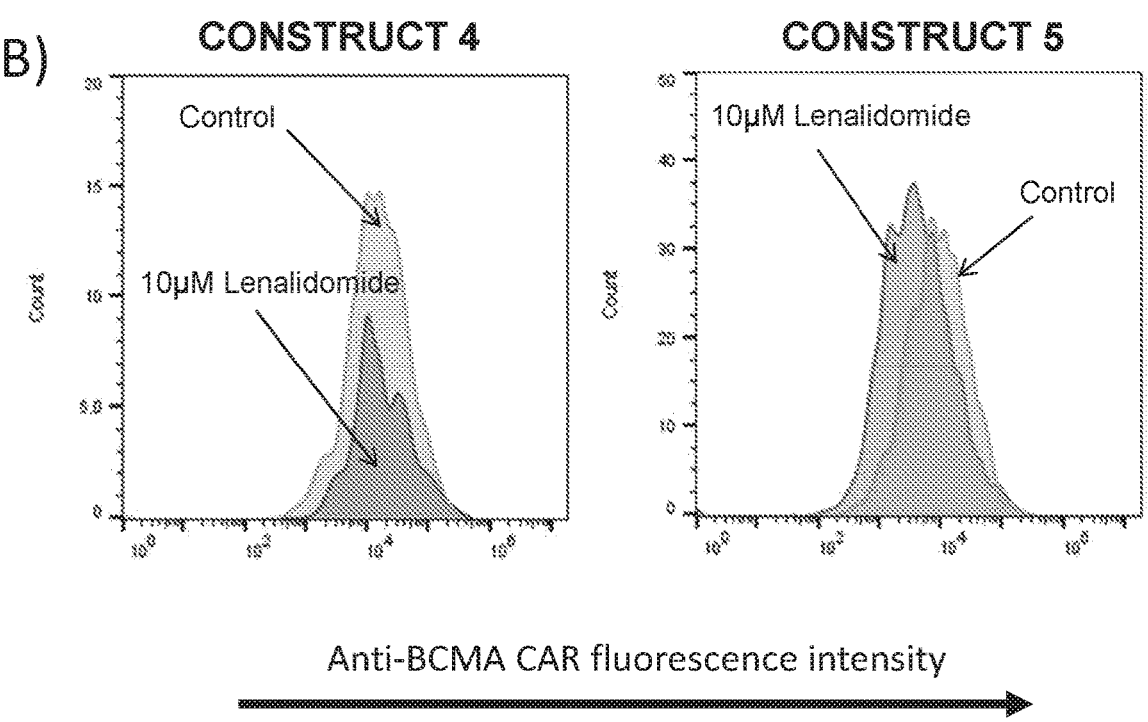

FIG. 5 displays the effect of lenalidomide treatment on the expression level of CAR molecules on the surface of Jurkat cells. CONSTRUCT 4, which does not contain any degron sequence is unaffected by the compound while CONSTRUCT 5 expression is reduced by the addition of 10 μM lenalidomide.

Example 4. Proximity Induced Degradation of Chimeric Antigen Receptor (CAR) Constructs in Primary T-Cells. Effect of Lenalidomide on Cytokine Release This example demonstrates that CAR containing degron sequences are functional in primary T-cells and are degraded by the addition of lenalidomide.

Materials and Methods

For lentiviral vector production, $3.0 \times 10^7$ LentiX 293T (HEK 293T) cells were seeded in 20 mL DMEM (Gibco) and were incubated overnight at 37° C. with 5% $CO_2$. LentiX cells were transfected by mixing, for example, 21 μg of transfer vector containing the construct, 3.75 μg ViraSafe pRSV-Rev, 5.25 μg ViraSafe pCMV-VSVG, 7.5 μg ViraSafe pCgp V-(gag-pol), 75 μg jetPRIME (Polyplus) and 1500 μg jetPRIME Buffer (Polyplus). After 2 days, supernatants were clarified and virus was concentrated and purified by ultracentrifugation on a 20% sucrose cushion using Ultrapure sucrose (ThermoFisher) in 50 ml Oak Ridge PPCO ultracentrifugation tubes (ThermoFisher). Lentiviral vectors were produced for CONSTRUCT 4 and CONSTRUCT 5 using the method described above.

Peripheral blood mononuclear cells (PBMCs) from the fresh blood of three healthy human donors were isolated by density gradient centrifugation in Accuspin tubes (Sigma) containing 15 mL of Histopaque-1077 (Sigma) and following manufacturer's instructions. Cells were resuspended at $1 \times 10^6$ cells/mL in TEXMacs media (Miltenyi Biotec) containing 100 units/mL of IL-2 (Sigma) and TransAct beads (Miltenyi Biotec) and incubated for 48 h at 37° C. with 5% $CO_2$.

T-cells from the three donors were then transduced with the lentiviral vectors encoding for CONSTRUCT 4 and CONSTRUCT 5. Transduction reactions were prepared to achieve an MOI of 5. T-cells were cultured in TEXMacs media with 100 units/mL of IL-2, fresh media was added every 3 days. ARH-77-10B5 cells, which express a high-level of the BCMA antigen, were cultured in Jurkat media (described in Example 3) plus 1 mg/mL G418 (Gibco) at 37° C. with 5% $CO_2$.

7 days after transduction, lenalidomide at a stock concentration of 10 mM in 100% DMSO was diluted in TEXMacs media to achieve a stock concentration of 250 μM, and $5 \times 10^4$ T-cells were incubated at a final compound concentration of 10 μM or 0 μM (DMSO in media) for 16 h at 37° C. with 5% $CO_2$. T-cells were then co-cultured ($5 \times 10^5$ cells per well, 1:1 effector: target ratio) with either ARH-77-10B5 cells (BCMA positive cells) or media for 24 h in TEXMacs media containing either 10 μM or 0 μM (DMSO in media) at 37° C. with 5% $CO_2$. Final DMSO concentration was 0.1% in all wells. Cells were pelleted (1200 rpm, 5 min) and supernatants were collected. Supernatants were analysed for cytokine levels using MSD V-plex Proinflammatory Panel 1 Human Kit (MSD) and MSD Sector Imager (MSD).

Results

Figure 6:
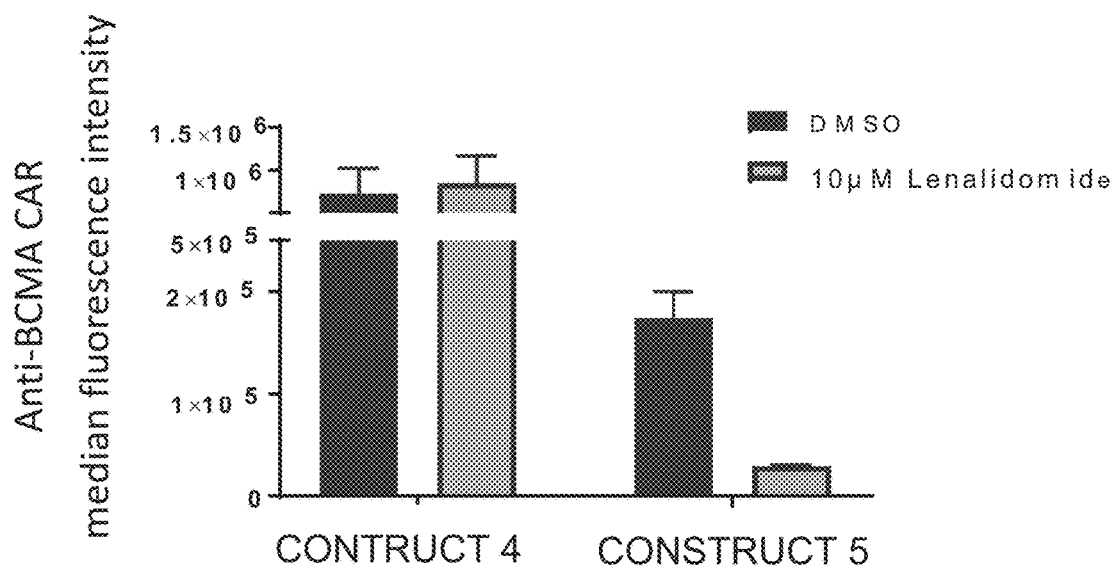
FIG. 6. Effect of lenalidomide treatment on the expression levels of anti-BCMA CARs fused with degrons in primary T-cells. (A) Median fluorescence intensity of anti-BCMA CAR in transduced (ZsGreen positive) T-cells cells after treatment with DMSO or 10 μM lenalidomide. CONSTRUCT 4 represents a CAR without a degron signal while CONSTRUCT 5 contains that same elements of CONSTRUCT 4 plus sequences derived from human Ikaros 3 (Uniprot Q9UKT9) protein. Data are representative of three biological repeats. (B) Flow cytometry histograms of the T-cells in (A), showing the effect of DMSO and 10 μM lenalidomide on anti-BCMA CAR expression.
Figure 6:
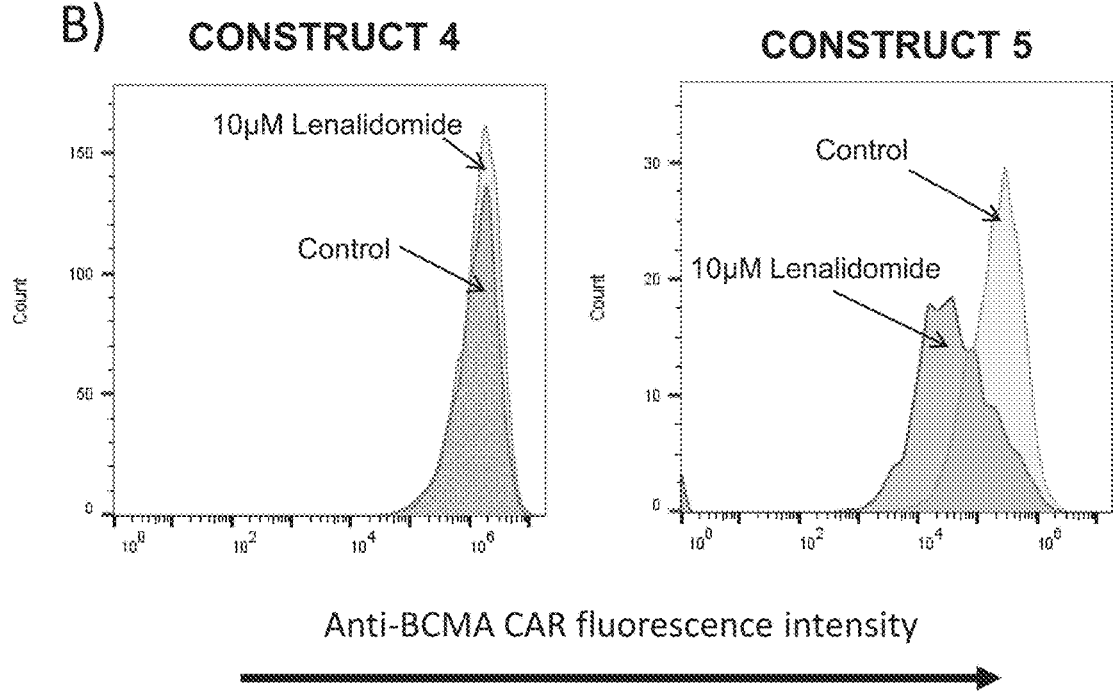
Figure 7:
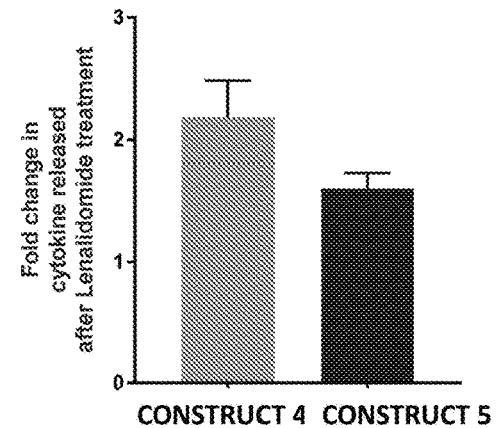
FIG. 7. Effect of lenalidomide treatment on the cytokine release from primary T-cells expressing anti-BCMA CARs fused with degrons. Primary T-cells were transduced with CONSTRUCT 4 or 5, and co-cultured with BCMA-expressing ARH-77-10B5 cells in the presence of DMSO or 10 μM lenalidomide. CONSTRUCT 4 represents a CAR without a degron signal while CONSTRUCT 5 contains that same elements of CONSTRUCT 4 plus sequences derived from human Ikaros 3 (Uniprot Q9UKT9) protein. Data are representative of three biological repeats.
Figure 7:
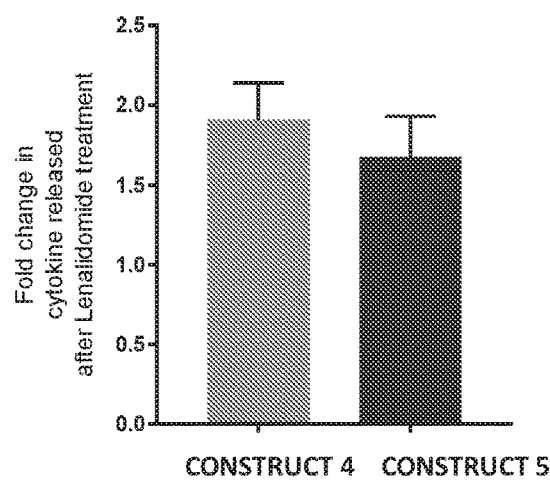
Figure 7:
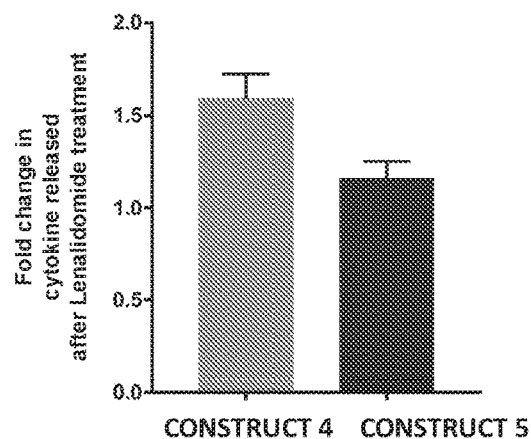

Effect of lenalidomide treatment on the expression levels of CONSTRUCTS 4 and 5 in transduced primary T-cells is shown in FIG. 6. After antigen presentation, T-cell supernatants were analysed for their TNFα, IL2 and IFN-γ levels. Supernatants corresponding to CONSTRUCT 4, a CAR construct without degron domain, showed increased levels of cytokines concentrations when compared with no lenalidomide treatment in line with published data (Otahal P et al. 2016 Oncoimmunology Vol. 5, No. 4), FIG. 7. This effect was also observed for cells transduced with CONSTRUCT 5 (CAR plus degron elements) but at a reduced extent when compared with the control CAR (CONSTRUCT 4), FIG. 7.

It will be understood that the embodiments described herein may be applied to all aspects of the invention. Furthermore, all publications, including but not limited to patents and patent applications, cited in this specification are herein incorporated by reference as though fully set forth.

SEQUENCES

| Structure | Sequence | SEQ ID NO. |
|---|---|---|
| Structural binding motif consensus sequences | $X_1X_2X_3X_4X_5GX_7X_8X_9X_{10}$ | 1 |
| Ikaros 3 (ZFN2) binding loop | QCGASFT | 2 |
| GSPT1 binding loop | VDKKSGEKSK | 3 |
| CK1 alpha binding loop | INITNGEEVA | 4 |
| ZFP91 binding loop | LQCEICGFTCR | 5 |
| Ikaros3 (141-173) | TGERPFQCNQCGASFTQKGNLLRHIKLHSTGEKP | 6 |
| Ikaros3 (141-173) plus Ub tag | TGERPFQCNQCGASFTQKGNLLRHIKLHTGEKPSTDPGDTASAEARHIKAEMG | 7 |
| Ikaros (131-175) (Uniprot Q9UKT9) | NVLMVHKRSHTGERPFQCNQCGASFTQKGNLLRHIKLHTGEKPFK | 8 |
| Ikaros3 (131-175) plus Ub tag (Ikaros 3 residues 231-249 (Uniprot Q9UKT9)) | NVLMVHKRSHTGERPFQCNQCGASFTQKGNLLRHIKLHTGEKPFKDPGDTASAEARHIKAEMG | 9 |
| Ikaros3 (117-249) | KMNCDVCGLSCISFNVLMVHKRSHTGERPFQCNQCGASFTQKGNLLRHIKLHTGEKPFKCHLCNYACQRRDALTGHLRTHSVEKPYKCEFCGRSYKQRSSLEEHKERCRTFLQSTDPGDTASAEARHIKAEMG | 10 |
| GSTP1 (388-499) | HSGRTFDAQIVIIEHKSIICPGYNAVLHIHTCIEEVEITALICLVDKKSGEKSKTRPRFVKQDQVCIARLRTAGTICLETFKDFPQMGRFTLRDEGKTIAIGKVLKLVPEKD | 11 |
| GSTP1 (388-499) F471S/M474S | HSGRTFDAQIVIIEHKSIICPGYNAVLHIHTCIEEVEITALICLVDKKSGEKSKTRPRFVKQDQVCIARLRTAGTICLETFKDSPQSGRFTLRDEGKTIAIGKVLKLVPEKD | 12 |
| CK1 alpha (8-94) | KAEFIVGGKYKLVRKIGSGSFGDIYLAINITNGEEVAVKLESQKARHPQLLYESKLYKILQGGVGIPHIRWYGQEKDYNVLVMDLLG | 13 |
| CK1 alpha (8-94) L63H/L67Q/I73Q | KAEFIVGGKYKLVKIGSGSFGDIYLAINITNGEEVAVKLESQKARHPQLLYESKHYKIQQGGVGQPHIRWYGQEKDYNVLVMDLLG | 14 |
| Expanded structural binding motif consensus sequence | $X_1X_2X_3X_4X_5GX_7X_8X_9X_{10}X_{11}X_{12}$ | 15 |
| Ubiquitination tag | STDPGDTASAEARHIKAEMG | 16 |
| CD8α transmembrane sequence | TRGLDFACDIYIWAPLAGTCGVLLLSLVITLYCNHRN | 17 |
| CD8α hinge sequence (Uniprot P01732). | FVPVFLPAKPTTTPAPRPPTPAPTIASQPLSLRPEACRPAAGGAVH | 18 |

-continued

| Structure | Sequence | SEQ ID NO. |
|---|---|---|
| CD8α hinge and transmembrane sequence (Uniprot P01732). | FVPVFLPAKTTTPAPRPPTPAPTIASQPLSLRPEACRPAAGGAVHTRGLDFACDIYIWAPLAGTCGVLLLSLVITLYCNHRN | 19 |
| CD3ζ domain (Uniprot P20963) | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 20 |
| 4-1BB costimulatory domain | KRGRKKLLYIFKQPFMRPVQTTQEEDGCSCRFPEEEEGGCEL | 21 |
| CD8α signal sequence (Uniprot P01732) | MALPVTALLLPLALLLHAARP | 22 |
| Linker 1 | GSGSGS | 23 |
| Linker 2 | GSGSGSGSGS | 24 |
| Linker 3 | GGGGS | 25 |
| Linker 4 | GS | 26 |
| Ikaros 1 residues 141-168 (Uniprot Q13422) | GERPFQCNQCGASFTQKGNLLRHIKLHS | 27 |
| Ikaros 3 residues 231-249 (Uniprot Q9UKT9) | DPGDTASAEARHIKAEMG | 28 |
| Anti-BCMA single chain Fv Amino Acid Sequence (Uniprot Q02223) | QVQLVQSGAEVKKPGSSVKVSCKGSGYTFTNYWMHWVRQAPGQGLEWIGATYRGHSDTYYNQKFKGRATLTADTSTSTAYMELSSLRSEDTAVYYCTRGAIYDGYDVLDNWGQGTLVTVSSGGGGSGGGGSGGGGSGGGGSDIQMTQSPSSLSASVGDRVTITCSASQDISNYLNWYQQKPGKAPKLLIYYTSNLHSGVPSRFSGSGSGTDFTLTISSLQPEDFATYYCQQYRKLPWTFGQGTKLEIKR | 29 |
| Construct 1 Amino Acid Sequence | MSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALSKDPNEKRDHMVLLEFVTAAGITLGMDELYKGSGERPFQCNQCGASFTQKGNLLRHIKLHS | 30 |
| Contruct 1 DNA Sequence | ATGAGCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGCAAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATGAAGCAGCACGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTGGTGAACCGCATCGAGCTGAAGGGCATCGACTTCAAGGAGGACGGCAACATCCTGGGGCACAAGCTGGAGTACAACTACAACAGCCACAACGTCTATATCATGGCCGACAAGCAGAAGAACGGCATCAAGGTGAACTTCAAGATCCGCCACAACATCGAGGACGGCAGCGTGCAGCTCGCCGACCACTACCAGCAGAACACCCCCATCGGCGACGGCCCCGTGCTGCTGCCCGACAACCACTACCTGAGCACCCAGTCCGCCCTGAGCAAAGACCCCAACGAGAAGCGCGATCACATGGTCCTGCTGGAGTTCGTGACCGCCGCCGGGATCACTCTCGGCATGGACGAGCTGTACAAGGGTTCAGGAGAACGGCCCTTCCAGTGCAATCAGTGCGGGGCCTCATTCACCCAGAAGGGCAACCTGCTCCGGCACATCAAGCTGCATTCC | 31 |

| Structure | Sequence | SEQ ID NO. |
|---|---|---|
| Construct 2 Amino Acid Sequence | MSKGEELFTGVVPILVELDGDVNGHKFSVSGEGE GDATYGKLTLKFICTTGKLPVPWPTLVTTLTYGV QCFSRYPDHMKQHDFFKSAMPEGYVQERTIFFKD DGNYKTRAEVKFEGDTLVNRIELKGIDFKEDGNI LGHKLEYNYNSHNVYIMADKQKNGIKVNFKIRHN IEDGSVQLADHYQQNTPIGDGPVLLPDNHYLSTQ SALSKDPNEKRDHMVLLEFVTAAGITLGMDELYK GSGSGSGSGERPFQCNQCGASFTQKGNLLRHIKLHS | 32 |
| Construct 2 DNA Sequence | ATGAGCAAGGGCGAGGAGCTGTTCACCGGGGTGG TGCCCATCCTGGTCGAGCTGGACGGCGACGTAAA CGGCCACAAGTTCAGCGTGTCCGGCGAGGGCGAG GGCGATGCCACCTACGGCAAGCTGACCCTGAAGT TCATCTGCACCACCGGCAAGCTGCCCGTGCCCTG GCCCACCCTCGTGACCACCCTGACCTACGGCGTG CAGTGCTTCAGCCGCTACCCCGACCACATGAAGC AGCACGACTTCTTCAAGTCCGCCATGCCCGAAGG CTACGTCCAGGAGCGCACCATCTTCTTCAAGGAC GACGGCAACTACAAGACCCGCGCCGAGGTGAAGT TCGAGGGCGACACCCTGGTGAACCGCATCGAGCT GAAGGGCATCGACTTCAAGGAGGACGGCAACATC CTGGGGCACAAGCTGGAGTACAACTACAACAGCC ACAACGTCTATATCATGGCCGACAAGCAGAAGAA CGGCATCAAGGTGAACTTCAAGATCCGCCACAAC ATCGAGGACGGCAGCGTGCAGCTCGCCGACCACT ACCAGCAGAACACCCCCATCGGCGACGGCCCCGT GCTGCTGCCCGACAACCACTACCTGAGCACCCAG TCCGCCCTGAGCAAAGACCCCAACGAGAAGCGCG ATCACATGGTCCTGCTGGAGTTCGTGACCGCCGC CGGGATCACTCTCGGCATGGACGAGCTGTACAAG GGTTCAGGTTCAGGTTCAGGAGAACGGCCCTTCC AGTGCAATCAGTGCGGGGCCTCATTCACCCAGAA GGGCAACCTGCTCCGGCACATCAAGCTGCATTCC | 33 |
| Construct 3 Amino Acid Sequence | MSKGEELFTGVVPILVELDGDVNGHKFSVSGEGE GDATYGKLTLKFICTTGKLPVPWPTLVTTLTYGV QCFSRYPDHMKQHDFFKSAMPEGYVQERTIFFKD DGNYKTRAEVKFEGDTLVNRIELKGIDFKEDGNI LGHKLEYNYNSHNVYIMADKQKNGIKVNFKIRHN IEDGSVQLADHYQQNTPIGDGPVLLPDNHYLSTQ SALSKDPNEKRDHMVLLEFVTAAGITLGMDELYK GSGSGSGSGSGERPFQCNQCGASFTQKGNLLRHI KLHS | 34 |
| Construct 3 DNA Sequence | ATGAGCAAGGGCGAGGAGCTGTTCACCGGGGTGG TGCCCATCCTGGTCGAGCTGGACGGCGACGTAAA CGGCCACAAGTTCAGCGTGTCCGGCGAGGGCGAG GGCGATGCCACCTACGGCAAGCTGACCCTGAAGT TCATCTGCACCACCGGCAAGCTGCCCGTGCCCTG GCCCACCCTCGTGACCACCCTGACCTACGGCGTG CAGTGCTTCAGCCGCTACCCCGACCACATGAAGC AGCACGACTTCTTCAAGTCCGCCATGCCCGAAGG CTACGTCCAGGAGCGCACCATCTTCTTCAAGGAC GACGGCAACTACAAGACCCGCGCCGAGGTGAAGT TCGAGGGCGACACCCTGGTGAACCGCATCGAGCT GAAGGGCATCGACTTCAAGGAGGACGGCAACATC CTGGGGCACAAGCTGGAGTACAACTACAACAGCC ACAACGTCTATATCATGGCCGACAAGCAGAAGAA CGGCATCAAGGTGAACTTCAAGATCCGCCACAAC ATCGAGGACGGCAGCGTGCAGCTCGCCGACCACT ACCAGCAGAACACCCCCATCGGCGACGGCCCCGT GCTGCTGCCCGACAACCACTACCTGAGCACCCAG TCCGCCCTGAGCAAAGACCCCAACGAGAAGCGCG ATCACATGGTCCTGCTGGAGTTCGTGACCGCCGC CGGGATCACTCTCGGCATGGACGAGCTGTACAAG GGTTCAGGTTCAGGTTCAGGTTCAGGTTCAGGAG AACGGCCCTTCCAGTGCAATCAGTGCGGGGCCTC ATTCACCCAGAAGGGCAACCTGCTCCGGCACATC AAGCTGCATTCC | 35 |
| Construct 4 Amino Acid Sequence | MALPVTALLLPLALLLHAARPQVQLVQSGAEVKK PGSSVKVSCKGSGYTFTNYWMHVRQAPGQGLEW IGATYRGHSDYYNQKFKGRATLTADTSTSTAYM ELSSLRSEDTAVYYCTRGAIYDGYDVLDNWGQGT LVTVSSGGGGSGGGGSGGGGSGGGGSDIQMTQSP | 36 |

| Structure | Sequence | SEQ ID NO. |
|---|---|---|
| | SSLSASVGDRVTITCSASQDISNYLNWYQQKPGK APKLLIYYTSNLHSGVPSRFSGSGSGTDFTLTIS SLQPEDFATYYCQQYRKLPWTFGQGTKLEIKRFV PVFLPAKPTTTPAPRPPTPAPTIASQPLSLRPEA CRPAAGGAVHTRGLDFACDIYIWAPLAGTCGVLL LSLVITLYCNHRNKRGRKKLLYIFKQPFMRPVQT TQEEDGCSCRFPEEEEGGCELRVKFSRSADAPAY QQGQNQLYNELNLGRREEYDVLDKRRGRDPEMGG KPRRKNPQEGLYNELQKDKMAEAYSEIGMKGERR RGKGHDGLYQGLSTATKDTYDALHMQALPPR | |
| Construct 4 DNA Sequence | ATGGCCCTGCCCGTGACCGCCCTCCTGCTGCCCC TGGCCCTGCTGCTGCACGCCGCCAGGCCCCAGGT CCAGCTGGTGCAGAGCGGGGCCGAGGTGAAGAAG CCCGGCAGCTCCGTGAAAGTGAGCTGCAAGGGCA GCGGCTACACCTTCACCAACTACTGGATGCACTG GGTGAGGCAGGCCCCCGGACAGGGACTGGAGTGG ATCGGCGCCACCTACAGGGGCCACAGCGACACCT ACTACAACCAGAAGTTCAAGGGCAGGGCCACCCT GACCGCCGACACTAGCACCAGCACCGCCTACATG GAACTGAGCTCACTGCGGAGCGAGGACACCGCCG TGTACTACTGCACCAGGGGCGCCATCTACGACGG CTACGACGTGCTGGACAACTGGGGCCAGGGCACC CTGGTGACAGTGAGCTCTGGCGGCGGCGGGAGCG GCGGCGGCGGAAGCGGCGGCGGAGGAAGCGGCGG CGGCGGAAGCGATATCCAGATGACCCAGAGCCCC AGCAGCCTGAGCGCCAGCGTGGGCGACAGGGTGA CCATCACCTGCAGCGCAAGCCAGGACATCAGCAA CTACCTGAACTGGTACCAGCAGAAGCCCGGCAAG GCCCCTAAGCTGCTGATCTACTACACCTCTAACC TGCACAGCGGCGTGCCCAGCAGGTTCTCTGGCAG CGGCTCCGGCACCGACTTCACTCTGACCATCAGC AGCCTCCAGCCCGAGGACTTCGCCACCTACTACT GCCAGCAGTACAGGAAGCTCCCCTGGACCTTCGG CCAGGGCACCAAGCTGGAGATCAAGCGCTTCGTG CCCGTGTTCCTCCCCGCAAAACCCACCACCACTC CCGCCCCCAGACCCCCACTCCCGCCCCAACAAT TGCCAGCCAGCCCCTGAGCCTGAGGCCCGAGGCT TGTAGGCCCGCCGCTGGCGGCGCCGTCCACACCA GGGGCCTGGACTTCGCCTGCGACATCTATATCTG GGCCCCCCTGGCCGGAACCTGCGGCGTGCTGCTG CTGAGCCTGGTGATCACCCTGTACTGCAACCACA GGAACAAGAGGGGCAGGAAGAAGCTCCTGTACAT CTTCAAGCAGCCCTTCATGAGGCCCGTGCAGACC ACCCAGGAGGAGGACGGCTGCAGCTGCAGGTTCC CAGAGGAAGAGGAGGGCGGGTGCGAACTGAGAGT GAAATTTAGCAGGAGCGCCGACGCCCCCGCCTAT CAGCAAGGCCAGAACCAGCTGTACAACGAGCTCA ACCTGGGCAGGAGGGAGGAGTACGACGTGCTGGA CAAGCGGAGGGGCAGAGATCCCGAGATGGGCGGC AAGCCCAGGAGGAAGAATCCCCAGGAGGGCCTGT ACAACGAGCTGCAGAAGGACAAGATGGCCGAGGC CTACAGCGAGATCGGCATGAAGGGGGAGAGGAGG AGGGGCAAGGGCCACGACGGCCTGTACCAGGGCC TGAGCACCGCCACCAAGGACACCTACGACGCCCT GCACATGCAGGCCCTGCCCCCCAGG | 37 |
| Construct 5 Amino Acid Sequence | MALPVTALLLPLALLLHAARPQVQLVQSGAEVKK PGSSVKVSCKGSGYTFTNYWMHWVRQAPGQGLEW IGATYRGHSDTYYNQKFKGRATLTADTSTSTAYM ELSSLRSEDTAVYYCTRGAIYDGYDVLDNWGQGT LVTVSSGGGGSGGGGSGGGGSGGGGSDIQMTQSP SSLSASVGDRVTITCSASQDISNYLNWYQQKPGK APKLLIYYTSNLHSGVPSRFSGSGSGTDFTLTIS SLQPEDFATYYCQQYRKLPWTFGQGTKLEIKRFV PVFLPAKPTTTPAPRPPTPAPTIASQPLSLRPEA CRPAAGGAVHTRGLDFACDIYIWAPLAGTCGVLL LSLVITLYCNHRNKRGRKKLLYIFKQPFMRPVQT TQEEDGCSCRFPEEEEGGCELGGGGSRVKFSRSA DAPAYQQGQNQLYNELNLGRREEYDVLDKRRGRD PEMGGKPRRKNPQEGLYNELQKDKMAEAYSEIGM KGERRRGKGHDGLYQGLSTATKDTYDALHMQALP PRGGGGSNVLMVHKRSHTGERPFQCNQCGASFTQ KGNLLRHIKLHTGEKPFKDPGDTASAEARHIKAE MG | 38 |

| Structure | Sequence | SEQ ID NO. |
|---|---|---|
| Construct 5 DNA Sequence | ATGGCTCTTCCTGTAACCGCACTTCTGCTTCCTC TTGCTCTGCTGCTTCATGCTGCTAGACCTCAGGT GCAGTTAGTGCAATCTGGAGCTGAGGTGAAGAAA CCTGGCTCTTCCGTGAAAGTGAGCTGTAAGGGAA GCGGCTACACCTTTACCAACTACTGGATGCATTG GGTGAGACAGGCCCCTGGACAGGGATTAGAGTGG ATTGGAGCCACATATAGAGGACACAGCGATACCT ACTACAACCAGAAGTTCAAGGGCAGGGCCACCCT TACAGCCGATACAAGCACATCTACCGCCTACATG GAACTGTCTTCTCTGAGAAGCGAGGATACCGCCG TGTACTACTGCACAAGAGGAGCCATCTACGACGG CTATGATGTTCTGGACAATTGGGGACAGGGCACA CTGGTGACAGTGTCTTCTGGTGGTGGCGGGTCCG GTGGAGGCGGATCTGGCGGTGGGGGCTCCGGAGG AGGAGGTTCAGATATTCAAATGACACAGAGCCCA AGCAGCCTGTCTGCTTCTGTGGGCGATAGAGTGA CCATCACCTGTTCTGCTTCTCAGGATATCAGCAA CTACCTGAACTGGTACCAGCAGAAGCCCGGCAAA GCCCCTAAACTGCTGATCTACTACACCAGCAATC TGCACTCTGGAGTTCCTAGCAGATTCAGCGGAAG CGGCTCTGGCACCGATTTTACACTGACCATCTCT TCTCTGCAGCCTGAGGATTTTGCCACCTACTACT GCCAGCAGTACCGGAAATTGCCTTGGACCTTTGG ACAGGGAACCAAGCTGGAGATCAAGAGGTTTGTG CCCGTGTTTCTGCCTGCTAAGCCTACAACAACAC CTGCCCCTAGACCACCTACACCTGCTCCTACAAT TGCCTCTCAGCCTCTTTCTCTGAGACCTGAAGCT TGCAGACCTGCTGCTGGAGGAGCTGTGCATACAA GAGGACTGGATTTTGCCTGCGATATCTACATTTG GGCTCCACTGGCCGGCACATGTGGAGTTCTTCTG CTGTCTCTGGTGATCACCCTGTACTGTAATCACA GGAACAAGCGGGGCCGGAAAAAGCTGCTGTACAT CTTCAAGCAGCCCTTCATGAGACCAGTTCAGACA ACACAGGAGGAGGACGGCTGTAGCTGCAGATTTC CTGAGGAAGAGGAAGGAGGATGTGAATTAGGTGG TGGCGGGAGCAGGGTGAAGTTCTCACGCAGCGCA GATGCTCCTGCCTATCAGCAAGGCCAGAATCAGC TGTACAACGAGCTGAATCTGGGCAGAAGAGAGGA GTACGATGTGCTGGACAAGAGAAGGGGCAGAGAT CCTGAAATGGGAGGAAAGCCCAGAAGGAAGAACC CTCAAGAAGGCCTGTACAATGAGCTGCAGAAGGA CAAGATGGCCGAGGCCTATAGCGAGATTGGCATG AAGGAGAGAGGAGAAGAGGAAAGGGCCATGATG GCCTGTATCAGGGCCTGTCTACAGCCACCAAGGA TACATATGATGCCCTGCATATGCAGGCTTTACCC CCTAGAGGAGGAGGCGGATCTAACGTGCTGATGG TGCATAAAAGAAGCCACACAGGAGAGAGACCATT CCAGTGCAACCAGTGTGGAGCCAGCTTCACCCAG AAGGGAAATCTGCTGAGACACATCAAACTGCATA CAGGCGAGAAGCCCTTCAAGGACCCTGGCGATAC AGCCTCTGCTGAAGCTAGACACATTAAAGCCGAA ATGGGC | 39 |

---

The invention claimed is:

1. A chimeric antigen receptor (CAR) comprising: an extracellular ligand binding domain; a transmembrane domain; an intracellular signalling domain; and, a ubiquitin targeting protein consisting of less than 135 amino acids in length which comprises the hairpin motif of a cereblon binding site, which is capable of being bound by ubiquitin ligase in the presence of a compound which mediates binding of the ubiquitin targeting protein and cereblon.

2. An isolated polynucleotide encoding the chimeric antigen receptor (CAR) of claim 1.

3. An expression vector comprising a polynucleotide of claim 2.

4. A cell comprising a polynucleotide of claim 2.

5. A cell of claim 4, which is an immunomodulatory cell.

6. A veil according to claim 5, which is a T-cell.

7. A pharmaceutical composition comprising a plurality of cells of claim 4.

8. The pharmaceutical composition of claim 7, which additionally comprises a pharmaceutically acceptable excipient, carrier, or diluent.

9. A method of engineering an immunomodulatory cell, comprising: (a) providing an immunomodulatory cell; (b) transducing or transfecting the polynucleotide of claim 2 into said immunomodulatory cell; and (c) expressing said polynucleotide in the immunomodulatory cell.

10. A method of affecting the amount of a polypeptide in a system comprising:
 a) contacting a fusion protein comprising said polypeptide and a ubiquitin targeting protein consisting of less than 135 amino acids in length which comprises the hairpin motif of a cereblon binding site, wherein said polypeptide is a transmembrane protein, and
 b) contacting a compound which mediates binding of the ubiquitin targeting protein and cereblon;
 wherein the binding of the ubiquitin targeting protein to cereblon affects the amount of polypeptide in a system.

11. A method of affecting the amount of a polypeptide in a system comprising:
 a) contacting a fusion protein comprising said polypeptide and a ubiquitin targeting protein consisting of less than 135 amino acids in length which comprises the hairpin motif of a cereblon binding site, wherein said polypeptide is a chimeric antigen receptor (CAR), and
 b) contacting a compound which mediates binding of the ubiquitin targeting protein and cereblon;
 wherein the binding of the ubiquitin targeting protein to cereblon affects the amount of polypeptide in a system.

* * * * *

SEQUENCE LISTING

<160> NUMBER OF SEQ ID NOS: 39

<210> SEQ ID NO 1
<211> LENGTH: 10
<212> TYPE: PRT
<213> ORGANISM: Artificial sequence
<220> FEATURE:
<223> OTHER INFORMATION: Structural binding motif consensus sequence
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid

```
<400> SEQUENCE: 1

Xaa Xaa Xaa Xaa Xaa Gly Xaa Xaa Xaa Xaa
1               5                   10

<210> SEQ ID NO 2
<211> LENGTH: 7
<212> TYPE: PRT
<213> ORGANISM: Homo sapiens

<400> SEQUENCE: 2

Gln Cys Gly Ala Ser Phe Thr
1               5

<210> SEQ ID NO 3
<211> LENGTH: 10
<212> TYPE: PRT
<213> ORGANISM: Homo sapiens

<400> SEQUENCE: 3

Val Asp Lys Lys Ser Gly Glu Lys Ser Lys
1               5                   10

<210> SEQ ID NO 4
<211> LENGTH: 10
<212> TYPE: PRT
<213> ORGANISM: Homo sapiens

<400> SEQUENCE: 4

Ile Asn Ile Thr Asn Gly Glu Glu Val Ala
1               5                   10

<210> SEQ ID NO 5
<211> LENGTH: 11
<212> TYPE: PRT
<213> ORGANISM: Homo sapiens

<400> SEQUENCE: 5

Leu Gln Cys Glu Ile Cys Gly Phe Thr Cys Arg
1               5                   10

<210> SEQ ID NO 6
<211> LENGTH: 34
<212> TYPE: PRT
<213> ORGANISM: Homo sapiens

<400> SEQUENCE: 6

Thr Gly Glu Arg Pro Phe Gln Cys Asn Gln Cys Gly Ala Ser Phe Thr
1               5                   10                  15

Gln Lys Gly Asn Leu Leu Arg His Ile Lys Leu His Ser Thr Gly Glu
            20                  25                  30

Lys Pro

<210> SEQ ID NO 7
<211> LENGTH: 53
<212> TYPE: PRT
<213> ORGANISM: Homo sapiens

<400> SEQUENCE: 7

Thr Gly Glu Arg Pro Phe Gln Cys Asn Gln Cys Gly Ala Ser Phe Thr
1               5                   10                  15

Gln Lys Gly Asn Leu Leu Arg His Ile Lys Leu His Thr Gly Glu Lys
            20                  25                  30
```

```
Pro Ser Thr Asp Pro Gly Asp Thr Ala Ser Ala Glu Ala Arg His Ile
            35                  40                  45

Lys Ala Glu Met Gly
    50

<210> SEQ ID NO 8
<211> LENGTH: 45
<212> TYPE: PRT
<213> ORGANISM: Homo sapiens

<400> SEQUENCE: 8

Asn Val Leu Met Val His Lys Arg Ser His Thr Gly Glu Arg Pro Phe
1               5                   10                  15

Gln Cys Asn Gln Cys Gly Ala Ser Phe Thr Gln Lys Gly Asn Leu Leu
            20                  25                  30

Arg His Ile Lys Leu His Thr Gly Glu Lys Pro Phe Lys
            35                  40                  45

<210> SEQ ID NO 9
<211> LENGTH: 63
<212> TYPE: PRT
<213> ORGANISM: Homo sapiens

<400> SEQUENCE: 9

Asn Val Leu Met Val His Lys Arg Ser His Thr Gly Glu Arg Pro Phe
1               5                   10                  15

Gln Cys Asn Gln Cys Gly Ala Ser Phe Thr Gln Lys Gly Asn Leu Leu
            20                  25                  30

Arg His Ile Lys Leu His Thr Gly Glu Lys Pro Phe Lys Asp Pro Gly
            35                  40                  45

Asp Thr Ala Ser Ala Glu Ala Arg His Ile Lys Ala Glu Met Gly
    50                  55                  60

<210> SEQ ID NO 10
<211> LENGTH: 133
<212> TYPE: PRT
<213> ORGANISM: Homo sapiens

<400> SEQUENCE: 10

Lys Met Asn Cys Asp Val Cys Gly Leu Ser Cys Ile Ser Phe Asn Val
1               5                   10                  15

Leu Met Val His Lys Arg Ser His Thr Gly Glu Arg Pro Phe Gln Cys
            20                  25                  30

Asn Gln Cys Gly Ala Ser Phe Thr Gln Lys Gly Asn Leu Leu Arg His
            35                  40                  45

Ile Lys Leu His Thr Gly Glu Lys Pro Phe Lys Cys His Leu Cys Asn
    50                  55                  60

Tyr Ala Cys Gln Arg Arg Asp Ala Leu Thr Gly His Leu Arg Thr His
65                  70                  75                  80

Ser Val Glu Lys Pro Tyr Lys Cys Glu Phe Cys Gly Arg Ser Tyr Lys
                85                  90                  95

Gln Arg Ser Ser Leu Glu Glu His Lys Glu Arg Cys Arg Thr Phe Leu
            100                 105                 110

Gln Ser Thr Asp Pro Gly Asp Thr Ala Ser Ala Glu Ala Arg His Ile
            115                 120                 125

Lys Ala Glu Met Gly
    130
```

```
<210> SEQ ID NO 11
<211> LENGTH: 112
<212> TYPE: PRT
<213> ORGANISM: Homo sapiens

<400> SEQUENCE: 11

His Ser Gly Arg Thr Phe Asp Ala Gln Ile Val Ile Ile Glu His Lys
1               5                   10                  15

Ser Ile Ile Cys Pro Gly Tyr Asn Ala Val Leu His Ile His Thr Cys
            20                  25                  30

Ile Glu Glu Val Glu Ile Thr Ala Leu Ile Cys Leu Val Asp Lys Lys
        35                  40                  45

Ser Gly Glu Lys Ser Lys Thr Arg Pro Arg Phe Val Lys Gln Asp Gln
    50                  55                  60

Val Cys Ile Ala Arg Leu Arg Thr Ala Gly Thr Ile Cys Leu Glu Thr
65                  70                  75                  80

Phe Lys Asp Phe Pro Gln Met Gly Arg Phe Thr Leu Arg Asp Glu Gly
                85                  90                  95

Lys Thr Ile Ala Ile Gly Lys Val Leu Lys Leu Val Pro Glu Lys Asp
            100                 105                 110

<210> SEQ ID NO 12
<211> LENGTH: 112
<212> TYPE: PRT
<213> ORGANISM: Homo sapiens

<400> SEQUENCE: 12

His Ser Gly Arg Thr Phe Asp Ala Gln Ile Val Ile Ile Glu His Lys
1               5                   10                  15

Ser Ile Ile Cys Pro Gly Tyr Asn Ala Val Leu His Ile His Thr Cys
            20                  25                  30

Ile Glu Glu Val Glu Ile Thr Ala Leu Ile Cys Leu Val Asp Lys Lys
        35                  40                  45

Ser Gly Glu Lys Ser Lys Thr Arg Pro Arg Phe Val Lys Gln Asp Gln
    50                  55                  60

Val Cys Ile Ala Arg Leu Arg Thr Ala Gly Thr Ile Cys Leu Glu Thr
65                  70                  75                  80

Phe Lys Asp Ser Pro Gln Ser Gly Arg Phe Thr Leu Arg Asp Glu Gly
                85                  90                  95

Lys Thr Ile Ala Ile Gly Lys Val Leu Lys Leu Val Pro Glu Lys Asp
            100                 105                 110

<210> SEQ ID NO 13
<211> LENGTH: 87
<212> TYPE: PRT
<213> ORGANISM: Homo sapiens

<400> SEQUENCE: 13

Lys Ala Glu Phe Ile Val Gly Gly Lys Tyr Lys Leu Val Arg Lys Ile
1               5                   10                  15

Gly Ser Gly Ser Phe Gly Asp Ile Tyr Leu Ala Ile Asn Ile Thr Asn
            20                  25                  30

Gly Glu Glu Val Ala Val Lys Leu Glu Ser Gln Lys Ala Arg His Pro
        35                  40                  45

Gln Leu Leu Tyr Glu Ser Lys Leu Tyr Lys Ile Leu Gln Gly Gly Val
    50                  55                  60

Gly Ile Pro His Ile Arg Trp Tyr Gly Gln Glu Lys Asp Tyr Asn Val
65                  70                  75                  80
```

```
Leu Val Met Asp Leu Leu Gly
            85

<210> SEQ ID NO 14
<211> LENGTH: 87
<212> TYPE: PRT
<213> ORGANISM: Homo sapiens

<400> SEQUENCE: 14

Lys Ala Glu Phe Ile Val Gly Gly Lys Tyr Lys Leu Val Arg Lys Ile
1               5                   10                  15

Gly Ser Gly Ser Phe Gly Asp Ile Tyr Leu Ala Ile Asn Ile Thr Asn
            20                  25                  30

Gly Glu Glu Val Ala Val Lys Leu Glu Ser Gln Lys Ala Arg His Pro
        35                  40                  45

Gln Leu Leu Tyr Glu Ser Lys His Tyr Lys Ile Gln Gln Gly Gly Val
    50                  55                  60

Gly Gln Pro His Ile Arg Trp Tyr Gly Gln Glu Lys Asp Tyr Asn Val
65                  70                  75                  80

Leu Val Met Asp Leu Leu Gly
            85

<210> SEQ ID NO 15
<211> LENGTH: 12
<212> TYPE: PRT
<213> ORGANISM: Artificial Sequence
<220> FEATURE:
<223> OTHER INFORMATION: Expanded structural binding motif consensus
      sequence
<220> FEATURE:
<221> NAME/KEY: MISC_FEATURE
<222> LOCATION: (1)..(1)
<223> OTHER INFORMATION: Xaa="Val" or "Ile" or absent
<220> FEATURE:
<221> NAME/KEY: MISC_FEATURE
<222> LOCATION: (2)..(2)
<223> OTHER INFORMATION: Xaa="Asp" or "Asn" or absent
<220> FEATURE:
<221> NAME/KEY: MISC_FEATURE
<222> LOCATION: (3)..(3)
<223> OTHER INFORMATION: Xaa="Lys" or "Ile" or absent
<220> FEATURE:
<221> NAME/KEY: MISC_FEATURE
<222> LOCATION: (4)..(4)
<223> OTHER INFORMATION: Xaa="Gln" or "Lys" or "Thr"
<220> FEATURE:
<221> NAME/KEY: MISC_FEATURE
<222> LOCATION: (5)..(5)
<223> OTHER INFORMATION: Xaa="Cys" or "Ser" or "Asn"
<220> FEATURE:
<221> NAME/KEY: MISC_FEATURE
<222> LOCATION: (7)..(7)
<223> OTHER INFORMATION: Xaa="Ala" or "Glu"
<220> FEATURE:
<221> NAME/KEY: MISC_FEATURE
<222> LOCATION: (8)..(8)
<223> OTHER INFORMATION: Xaa="Ser" or "Lys" or "Glu" or absent
<220> FEATURE:
<221> NAME/KEY: MISC_FEATURE
<222> LOCATION: (9)..(9)
<223> OTHER INFORMATION: Xaa="Phe" or "Ser" or "Val" or absent
<220> FEATURE:
<221> NAME/KEY: MISC_FEATURE
<222> LOCATION: (10)..(10)
<223> OTHER INFORMATION: Xaa="Thr" or "Lys" or "Ala" or absent
<220> FEATURE:
<221> NAME/KEY: MISC_FEATURE
<222> LOCATION: (11)..(11)
<223> OTHER INFORMATION: Xaa="Gln" or "Thr" or "Val" or absent
<220> FEATURE:
```

```
<221> NAME/KEY: MISC_FEATURE
<222> LOCATION: (12)..(12)
<223> OTHER INFORMATION: Xaa="Lys" or "Arg"

<400> SEQUENCE: 15

Xaa Xaa Xaa Xaa Xaa Gly Xaa Xaa Xaa Xaa Xaa Xaa
1               5                   10

<210> SEQ ID NO 16
<211> LENGTH: 20
<212> TYPE: PRT
<213> ORGANISM: Homo sapiens

<400> SEQUENCE: 16

Ser Thr Asp Pro Gly Asp Thr Ala Ser Ala Glu Ala Arg His Ile Lys
1               5                   10                  15

Ala Glu Met Gly
            20

<210> SEQ ID NO 17
<211> LENGTH: 37
<212> TYPE: PRT
<213> ORGANISM: Homo sapiens

<400> SEQUENCE: 17

Thr Arg Gly Leu Asp Phe Ala Cys Asp Ile Tyr Ile Trp Ala Pro Leu
1               5                   10                  15

Ala Gly Thr Cys Gly Val Leu Leu Leu Ser Leu Val Ile Thr Leu Tyr
            20                  25                  30

Cys Asn His Arg Asn
            35

<210> SEQ ID NO 18
<211> LENGTH: 46
<212> TYPE: PRT
<213> ORGANISM: Homo sapiens

<400> SEQUENCE: 18

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His
            35                  40                  45

<210> SEQ ID NO 19
<211> LENGTH: 83
<212> TYPE: PRT
<213> ORGANISM: Homo sapiens

<400> SEQUENCE: 19

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
            35                  40                  45

Gly Leu Asp Phe Ala Cys Asp Ile Tyr Ile Trp Ala Pro Leu Ala Gly
            50                  55                  60

Thr Cys Gly Val Leu Leu Leu Ser Leu Val Ile Thr Leu Tyr Cys Asn
65                  70                  75                  80
```

His Arg Asn

<210> SEQ ID NO 20
<211> LENGTH: 112
<212> TYPE: PRT
<213> ORGANISM: Homo sapiens

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 21
<211> LENGTH: 42
<212> TYPE: PRT
<213> ORGANISM: Homo sapiens

<400> SEQUENCE: 21

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 22
<211> LENGTH: 21
<212> TYPE: PRT
<213> ORGANISM: Homo sapiens

<400> SEQUENCE: 22

Met Ala Leu Pro Val Thr Ala Leu Leu Leu Pro Leu Ala Leu Leu Leu
1               5                   10                  15

His Ala Ala Arg Pro
            20

<210> SEQ ID NO 23
<211> LENGTH: 6
<212> TYPE: PRT
<213> ORGANISM: Artificial sequence
<220> FEATURE:
<223> OTHER INFORMATION: Linker 1

<400> SEQUENCE: 23

Gly Ser Gly Ser Gly Ser
1               5

<210> SEQ ID NO 24
<211> LENGTH: 10

```
<212> TYPE: PRT
<213> ORGANISM: Artificial sequence
<220> FEATURE:
<223> OTHER INFORMATION: Linker 2

<400> SEQUENCE: 24

Gly Ser Gly Ser Gly Ser Gly Ser Gly Ser
1               5                   10

<210> SEQ ID NO 25
<211> LENGTH: 5
<212> TYPE: PRT
<213> ORGANISM: Artificial sequence
<220> FEATURE:
<223> OTHER INFORMATION: Linker 3

<400> SEQUENCE: 25

Gly Gly Gly Gly Ser
1               5

<210> SEQ ID NO 26
<211> LENGTH: 4
<212> TYPE: PRT
<213> ORGANISM: Artificial sequence
<220> FEATURE:
<223> OTHER INFORMATION: Linker 4
<220> FEATURE:
<221> NAME/KEY: MISC_FEATURE
<222> LOCATION: (1)..(1)
<223> OTHER INFORMATION: Xaa is absent
<220> FEATURE:
<221> NAME/KEY: MISC_FEATURE
<222> LOCATION: (4)..(4)
<223> OTHER INFORMATION: Xaa is absent

<400> SEQUENCE: 26

Xaa Gly Ser Xaa
1

<210> SEQ ID NO 27
<211> LENGTH: 28
<212> TYPE: PRT
<213> ORGANISM: Homo sapiens

<400> SEQUENCE: 27

Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser
            20                  25

<210> SEQ ID NO 28
<211> LENGTH: 18
<212> TYPE: PRT
<213> ORGANISM: Homo sapiens

<400> SEQUENCE: 28

Asp Pro Gly Asp Thr Ala Ser Ala Glu Ala Arg His Ile Lys Ala Glu
1               5                   10                  15

Met Gly

<210> SEQ ID NO 29
<211> LENGTH: 249
<212> TYPE: PRT
<213> ORGANISM: Homo sapiens

<400> SEQUENCE: 29
```

```
Gln Val Gln Leu Val Gln Ser Gly Ala Glu Val Lys Lys Pro Gly Ser
1               5                   10                  15

Ser Val Lys Val Ser Cys Lys Gly Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Ala Thr Tyr Arg Gly His Ser Asp Thr Tyr Tyr Asn Gln Lys Phe
    50                  55                  60

Lys Gly Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Ala Ile Tyr Asp Gly Tyr Asp Val Leu Asp Asn Trp Gly
            100                 105                 110

Gln Gly Thr Leu Val Thr Val Ser Gly Gly Gly Ser Gly Gly
        115                 120                 125

Gly Gly Ser Gly Gly Gly Ser Gly Gly Gly Ser Asp Ile Gln
        130                 135                 140

Met Thr Gln Ser Pro Ser Ser Leu Ser Ala Ser Val Gly Asp Arg Val
145                 150                 155                 160

Thr Ile Thr Cys Ser Ala Ser Gln Asp Ile Ser Asn Tyr Leu Asn Trp
            165                 170                 175

Tyr Gln Gln Lys Pro Gly Lys Ala Pro Lys Leu Leu Ile Tyr Tyr Thr
        180                 185                 190

Ser Asn Leu His Ser Gly Val Pro Ser Arg Phe Ser Gly Ser Gly Ser
    195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Tyr Arg Lys Leu Pro Trp Thr Phe Gly
225                 230                 235                 240

Gln Gly Thr Lys Leu Glu Ile Lys Arg
                245
```

<210> SEQ ID NO 30
<211> LENGTH: 268
<212> TYPE: PRT
<213> ORGANISM: Artificial sequence
<220> FEATURE:
<223> OTHER INFORMATION: Construct 1 Amino Acid Sequence

<400> SEQUENCE: 30

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110
```

```
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys Gly Ser
225                 230                 235                 240

Gly Glu Arg Pro Phe Gln Cys Asn Gln Cys Gly Ala Ser Phe Thr Gln
                245                 250                 255

Lys Gly Asn Leu Leu Arg His Ile Lys Leu His Ser
            260                 265
```

<210> SEQ ID NO 31
<211> LENGTH: 804
<212> TYPE: DNA
<213> ORGANISM: Artificial sequence
<220> FEATURE:
<223> OTHER INFORMATION: Construct 1 DNA Sequence

<400> SEQUENCE: 31

```
atgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg cccaccctc    180
gtgaccaccc tgacctacgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacaacag ccacaacgtc tatatcatgg ccgacaagca agaacggc     480
atcaaggtga acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg   660
ctggagttcg tgaccgccgc cgggatcact ctcggcatgg acgagctgta caagggttca   720
ggagaacggc ccttccagtg caatcagtgc ggggcctcat tcacccagaa gggcaacctg   780
ctccggcaca tcaagctgca ttcc                                          804
```

<210> SEQ ID NO 32
<211> LENGTH: 272
<212> TYPE: PRT
<213> ORGANISM: Artificial sequence
<220> FEATURE:
<223> OTHER INFORMATION: Construct 2 Amino Acid Sequence

<400> SEQUENCE: 32

Met Ser Lys Gly Glu Glu Leu Phe Thr Gly Val Val Pro Ile Leu Val

```
              1               5                  10                 15
              Glu Leu Asp Gly Asp Val Asn Gly His Lys Phe Ser Val Ser Gly Glu
                              20                 25                 30
              Gly Glu Gly Asp Ala Thr Tyr Gly Lys Leu Thr Leu Lys Phe Ile Cys
                              35                 40                 45
              Thr Thr Gly Lys Leu Pro Val Pro Trp Pro Thr Leu Val Thr Thr Leu
                  50                     55                 60
              Thr Tyr Gly Val Gln Cys Phe Ser Arg Tyr Pro Asp His Met Lys Gln
              65                     70                 75                 80
              His Asp Phe Phe Lys Ser Ala Met Pro Glu Gly Tyr Val Gln Glu Arg
                                  85                 90                 95
              Thr Ile Phe Phe Lys Asp Asp Gly Asn Tyr Lys Thr Arg Ala Glu Val
                              100                105                110
              Lys Phe Glu Gly Asp Thr Leu Val Asn Arg Ile Glu Leu Lys Gly Ile
                              115                120                125
              Asp Phe Lys Glu Asp Gly Asn Ile Leu Gly His Lys Leu Glu Tyr Asn
                              130                135                140
              Tyr Asn Ser His Asn Val Tyr Ile Met Ala Asp Lys Gln Lys Asn Gly
              145                    150                155                160
              Ile Lys Val Asn Phe Lys Ile Arg His Asn Ile Glu Asp Gly Ser Val
                                  165                170                175
              Gln Leu Ala Asp His Tyr Gln Gln Asn Thr Pro Ile Gly Asp Gly Pro
                              180                185                190
              Val Leu Leu Pro Asp Asn His Tyr Leu Ser Thr Gln Ser Ala Leu Ser
                              195                200                205
              Lys Asp Pro Asn Glu Lys Arg Asp His Met Val Leu Leu Glu Phe Val
                              210                215                220
              Thr Ala Ala Gly Ile Thr Leu Gly Met Asp Glu Leu Tyr Lys Gly Ser
              225                    230                235                240
              Gly Ser Gly Ser Gly Glu Arg Pro Phe Gln Cys Asn Gln Cys Gly Ala
                                  245                250                255
              Ser Phe Thr Gln Lys Gly Asn Leu Leu Arg His Ile Lys Leu His Ser
                              260                265                270

<210> SEQ ID NO 33
<211> LENGTH: 816
<212> TYPE: DNA
<213> ORGANISM: Artificial sequence
<220> FEATURE:
<223> OTHER INFORMATION: Construct 2 DNA Sequence

<400> SEQUENCE: 33
atgagcaagg gcgaggagct gttcaccggg gtggtgccca tcctggtcga gctggacggc        60
gacgtaaacg gccacaagtt cagcgtgtcc ggcgagggcg agggcgatgc cacctacggc       120
aagctgaccc tgaagttcat ctgcaccacc ggcaagctgc ccgtgccctg gcccaccctc       180
gtgaccaccc tgacctacgg cgtgcagtgc ttcagccgct accccgacca catgaagcag       240
cacgacttct tcaagtccgc catgcccgaa ggctacgtcc aggagcgcac catcttcttc       300
aaggacgacg gcaactacaa gacccgcgcc gaggtgaagt tcgagggcga cacccTggtg       360
aaccgcatcg agctgaaggg catcgacttc aaggaggacg gcaacatcct ggggcacaag       420
ctggagtaca actacaacag ccacaacgtc tatatcatgg ccgacaagca gaagaacggc       480
atcaaggtga acttcaagat ccgccacaac atcgaggacg gcagcgtgca gctcgccgac       540
cactaccagc agaacacccc catcggcgac ggccccgtgc tgctgcccga caaccactac       600
```

```
ctgagcaccc agtccgccct gagcaaagac cccaacgaga agcgcgatca catggtcctg    660
ctggagttcg tgaccgccgc cgggatcact ctcggcatgg acgagctgta caagggttca    720
ggttcaggtt caggagaacg gcccttccag tgcaatcagt gcggggcctc attcacccag    780
aagggcaacc tgctccggca catcaagctg cattcc                             816
```

```
<210> SEQ ID NO 34
<211> LENGTH: 276
<212> TYPE: PRT
<213> ORGANISM: Artificial sequence
<220> FEATURE:
<223> OTHER INFORMATION: Construct 3 Amino Acid Sequence

<400> SEQUENCE: 34
```

| | | | | | | | | | | | | | | |
|---|---|---|---|---|---|---|---|---|---|---|---|---|---|---|
| Met | Ser | Lys | Gly | Glu | Glu | Leu | Phe | Thr | Gly | Val | Val | Pro | Ile | Leu | Val |
| 1 | | | | 5 | | | | | 10 | | | | | 15 | |
| Glu | Leu | Asp | Gly | Asp | Val | Asn | Gly | His | Lys | Phe | Ser | Val | Ser | Gly | Glu |
| | | | 20 | | | | | 25 | | | | | 30 | | |
| Gly | Glu | Gly | Asp | Ala | Thr | Tyr | Gly | Lys | Leu | Thr | Leu | Lys | Phe | Ile | Cys |
| | | 35 | | | | | 40 | | | | | 45 | | | |
| Thr | Thr | Gly | Lys | Leu | Pro | Val | Pro | Trp | Pro | Thr | Leu | Val | Thr | Thr | Leu |
| 50 | | | | | 55 | | | | | 60 | | | | | |
| Thr | Tyr | Gly | Val | Gln | Cys | Phe | Ser | Arg | Tyr | Pro | Asp | His | Met | Lys | Gln |
| 65 | | | | | 70 | | | | | 75 | | | | | 80 |
| His | Asp | Phe | Phe | Lys | Ser | Ala | Met | Pro | Glu | Gly | Tyr | Val | Gln | Glu | Arg |
| | | | | 85 | | | | | 90 | | | | | 95 | |
| Thr | Ile | Phe | Phe | Lys | Asp | Asp | Gly | Asn | Tyr | Lys | Thr | Arg | Ala | Glu | Val |
| | | | 100 | | | | | 105 | | | | | 110 | | |
| Lys | Phe | Glu | Gly | Asp | Thr | Leu | Val | Asn | Arg | Ile | Glu | Leu | Lys | Gly | Ile |
| | | 115 | | | | | 120 | | | | | 125 | | | |
| Asp | Phe | Lys | Glu | Asp | Gly | Asn | Ile | Leu | Gly | His | Lys | Leu | Glu | Tyr | Asn |
| 130 | | | | | 135 | | | | | 140 | | | | | |
| Tyr | Asn | Ser | His | Asn | Val | Tyr | Ile | Met | Ala | Asp | Lys | Gln | Lys | Asn | Gly |
| 145 | | | | | 150 | | | | | 155 | | | | | 160 |
| Ile | Lys | Val | Asn | Phe | Lys | Ile | Arg | His | Asn | Ile | Glu | Asp | Gly | Ser | Val |
| | | | | 165 | | | | | 170 | | | | | 175 | |
| Gln | Leu | Ala | Asp | His | Tyr | Gln | Gln | Asn | Thr | Pro | Ile | Gly | Asp | Gly | Pro |
| | | | 180 | | | | | 185 | | | | | 190 | | |
| Val | Leu | Leu | Pro | Asp | Asn | His | Tyr | Leu | Ser | Thr | Gln | Ser | Ala | Leu | Ser |
| | | 195 | | | | | 200 | | | | | 205 | | | |
| Lys | Asp | Pro | Asn | Glu | Lys | Arg | Asp | His | Met | Val | Leu | Leu | Glu | Phe | Val |
| 210 | | | | | 215 | | | | | 220 | | | | | |
| Thr | Ala | Ala | Gly | Ile | Thr | Leu | Gly | Met | Asp | Glu | Leu | Tyr | Lys | Gly | Ser |
| 225 | | | | | 230 | | | | | 235 | | | | | 240 |
| Gly | Ser | Gly | Ser | Gly | Ser | Gly | Ser | Gly | Glu | Arg | Pro | Phe | Gln | Cys | Asn |
| | | | | 245 | | | | | 250 | | | | | 255 | |
| Gln | Cys | Gly | Ala | Ser | Phe | Thr | Gln | Lys | Gly | Asn | Leu | Leu | Arg | His | Ile |
| | | | 260 | | | | | 265 | | | | | 270 | | |
| Lys | Leu | His | Ser | | | | | | | | | | | | |
| | | | 275 | | | | | | | | | | | | |

```
<210> SEQ ID NO 35
<211> LENGTH: 828
<212> TYPE: DNA
<213> ORGANISM: Artificial sequence
<220> FEATURE:
```

<223> OTHER INFORMATION: Construct 3 DNA Sequence

<400> SEQUENCE: 35

```
atgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctacgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga cacccctgtg   360
aaccgcatcg agctgaaggg catcgacttc aaggaggacg gcaacatcct ggggcacaag   420
ctggagtaca actacaacag ccacaacgtc tatatcatgg ccgacaagca gaagaacggc   480
atcaaggtga acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg   660
ctggagttcg tgaccgccgc cgggatcact ctcggcatgg acgagctgta caagggttca   720
ggttcaggtt caggttcagg ttcaggagaa cggcccttcc agtgcaatca gtgcggggcc   780
tcattcaccc agaagggcaa cctgctccgg cacatcaagc tgcattcc               828
```

<210> SEQ ID NO 36
<211> LENGTH: 507
<212> TYPE: PRT
<213> ORGANISM: Artificial sequence
<220> FEATURE:
<223> OTHER INFORMATION: Construct 4 Amino Acid Sequence

<400> SEQUENCE: 36

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ser Ser Val Lys Val Ser Cys Lys Gly Ser Gly Tyr
        35                  40                  45

Thr Phe Thr Asn Tyr Trp Met His Trp Val Arg Gln Ala Pro Gly Gln
    50                  55                  60

Gly Leu Glu Trp Ile Gly Ala Thr Tyr Arg Gly His Ser Asp Thr Tyr
65                  70                  75                  80

Tyr Asn Gln Lys Phe Lys Gly Arg Ala Thr Leu Thr Ala Asp Thr Ser
                85                  90                  95

Thr Ser Thr Ala Tyr Met Glu Leu Ser Ser Leu Arg Ser Glu Asp Thr
            100                 105                 110

Ala Val Tyr Tyr Cys Thr Arg Gly Ala Ile Tyr Asp Gly Tyr Asp Val
        115                 120                 125

Leu Asp Asn Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Ser Ala Ser Gln Asp Ile Ser
            180                 185                 190

Asn Tyr Leu Asn Trp Tyr Gln Gln Lys Pro Gly Lys Ala Pro Lys Leu
```

|     |     |     |     |     | 195 |     |     |     | 200 |     |     |     |     | 205 |     |     |     |
| --- | --- | --- | --- | --- | --- | --- | --- | --- | --- | --- | --- | --- | --- | --- | --- | --- | --- |
| Leu | Ile | Tyr | Tyr | Thr | Ser | Asn | Leu | His | Ser | Gly | Val | Pro | Ser | Arg | Phe |

Leu Ile Tyr Tyr Thr Ser Asn Leu His Ser Gly Val Pro Ser Arg Phe
    210                      215                    220

Ser Gly Ser Gly Ser Gly Thr Asp Phe Thr Leu Thr Ile Ser Ser Leu
225                    230                    235                    240

Gln Pro Glu Asp Phe Ala Thr Tyr Tyr Cys Gln Gln Tyr Arg Lys Leu
              245                    250                    255

Pro Trp Thr Phe Gly Gln Gly Thr Lys Leu Glu Ile Lys Arg Phe Val
          260                    265                    270

Pro Val Phe Leu Pro Ala Lys Pro Thr Thr Thr Pro Ala Pro Arg Pro
        275                    280                    285

Pro Thr Pro Ala Pro Thr Ile Ala Ser Gln Pro Leu Ser Leu Arg Pro
290                    295                    300

Glu Ala Cys Arg Pro Ala Ala Gly Gly Ala Val His Thr Arg Gly Leu
305                    310                    315                    320

Asp Phe Ala Cys Asp Ile Tyr Ile Trp Ala Pro Leu Ala Gly Thr Cys
              325                    330                    335

Gly Val Leu Leu Leu Ser Leu Val Ile Thr Leu Tyr Cys Asn His Arg
          340                    345                    350

Asn Lys Arg Gly Arg Lys Lys Leu Leu Tyr Ile Phe Lys Gln Pro Phe
        355                    360                    365

Met Arg Pro Val Gln Thr Thr Gln Glu Glu Asp Gly Cys Ser Cys Arg
370                    375                    380

Phe Pro Glu Glu Glu Glu Gly Gly Cys Glu Leu Arg Val Lys Phe Ser
385                    390                    395                    400

Arg Ser Ala Asp Ala Pro Ala Tyr Gln Gln Gly Gln Asn Gln Leu Tyr
              405                    410                    415

Asn Glu Leu Asn Leu Gly Arg Arg Glu Glu Tyr Asp Val Leu Asp Lys
          420                    425                    430

Arg Arg Gly Arg Asp Pro Glu Met Gly Gly Lys Pro Arg Arg Lys Asn
        435                    440                    445

Pro Gln Glu Gly Leu Tyr Asn Glu Leu Gln Lys Asp Lys Met Ala Glu
    450                    455                    460

Ala Tyr Ser Glu Ile Gly Met Lys Gly Glu Arg Arg Arg Gly Lys Gly
465                    470                    475                    480

His Asp Gly Leu Tyr Gln Gly Leu Ser Thr Ala Thr Lys Asp Thr Tyr
              485                    490                    495

Asp Ala Leu His Met Gln Ala Leu Pro Pro Arg
        500                    505

<210> SEQ ID NO 37
<211> LENGTH: 1521
<212> TYPE: DNA
<213> ORGANISM: Artificial sequence
<220> FEATURE:
<223> OTHER INFORMATION: Construct 4 DNA Sequence

<400> SEQUENCE: 37
atggccctgc ccgtgaccgc cctcctgctg ccctggccc tgctgctgca cgccgccagg    60
ccccaggtcc agctggtgca gagcggggcc gaggtgaaga gcccggcag ctccgtgaaa   120 gtgagctgca agggcagcgg ctacaccttc accaactact ggatgcactg ggtgaggcag   180
gcccccggac agggactgga gtggatcggc gccacctaca gggccacag cgacacctac   240 tacaaccaga gttcaagggg cagggccacc ctgaccgccg acactagcac cagcaccgcc   300

```
tacatggaac tgagctcact gcggagcgag gacaccgccg tgtactactg caccagggc     360
gccatctacg acggctacga cgtgctggac aactggggcc agggcaccct ggtgacagtg     420
agctctggcg gcggcgggag cggcggcggc ggaagcggcg gcggaggaag cggcggcggc     480
ggaagcgata tccagatgac ccagagcccc agcagcctga cgccagcgt gggcgacagg     540
gtgaccatca cctgcagcgc aagccaggac atcagcaact acctgaactg gtaccagcag     600
aagcccggca aggcccctaa gctgctgatc tactacacct ctaacctgca cagcggcgtg     660
cccagcaggt tctctggcag cggctccggc accgacttca ctctgaccat cagcagcctc     720
cagcccgagg acttcgccac ctactactgc cagcagtaca ggaagctccc ctggaccttc     780
ggccagggca ccaagctgga gatcaagcgc ttcgtgcccg tgttcctccc cgcaaaaccc     840
accaccactc ccgccccag acccccact cccgcccaa caattgccag ccagcccctg     900
agcctgaggc ccgaggcttg taggcccgcc gctggcggcg ccgtccacac caggggcctg     960
gacttcgcct gcgacatcta tatctggggc ccctggccg gaacctgcgg cgtgctgctg    1020
ctgagcctgg tgatcaccct gtactgcaac cacaggaaca agaggggcag gaagaagctc    1080
ctgtacatct tcaagcagcc cttcatgagg cccgtgcaga ccacccagga ggaggacggc    1140
tgcagctgca ggttcccaga ggaagaggag ggcgggtgcg aactgagagt gaaatttagc    1200
aggagcgccg acgccccgc ctatcagcaa ggccagaacc agctgtacaa cgagctcaac    1260
ctgggcagga ggaggagta cgacgtgctg acaagcgga gggcagaga tcccgagatg    1320
ggcggcaagc caggaggaa gaatccccag gagggcctgt acaacgagct gcagaaggac    1380
aagatggccg aggcctacag cgagatcggc atgaaggggg agaggaggag gggcaagggc    1440
cacgacggcc tgtaccaggg cctgagcacc gccaccaagg acacctacga cgccctgcac    1500
atgcaggccc tgcccccag g                                                  1521

<210> SEQ ID NO 38
<211> LENGTH: 580
<212> TYPE: PRT
<213> ORGANISM: Artificial sequence
<220> FEATURE:
<223> OTHER INFORMATION: Construct 5 Amino Acid Sequence

<400> SEQUENCE: 38

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Gly Ser Gly Tyr
        35                  40                  45

Thr Phe Thr Asn Tyr Trp Met His Trp Val Arg Gln Ala Pro Gly Gln
    50                  55                  60

Gly Leu Glu Trp Ile Gly Ala Thr Tyr Arg Gly His Ser Asp Thr Tyr
65                  70                  75                  80

Tyr Asn Gln Lys Phe Lys Gly Arg Ala Thr Leu Thr Ala Asp Thr Ser
                85                  90                  95

Thr Ser Thr Ala Tyr Met Glu Leu Ser Ser Leu Arg Ser Glu Asp Thr
            100                 105                 110

Ala Val Tyr Tyr Cys Thr Arg Gly Ala Ile Tyr Asp Gly Tyr Asp Val
        115                 120                 125

Leu Asp Asn Trp Gly Gln Gly Thr Leu Val Thr Val Ser Ser Gly Gly
    130                 135                 140
```

```
Gly Gly Ser Gly Gly Gly Ser Gly Gly Gly Ser Gly Gly Gly
145                 150                 155                 160
Gly Ser Asp Ile Gln Met Thr Gln Ser Pro Ser Ser Leu Ser Ala Ser
            165                 170                 175
Val Gly Asp Arg Val Thr Ile Thr Cys Ser Ala Ser Gln Asp Ile Ser
                180                 185                 190
Asn Tyr Leu Asn Trp Tyr Gln Gln Lys Pro Gly Lys Ala Pro Lys Leu
            195                 200                 205
Leu Ile Tyr Tyr Thr Ser Asn Leu His Ser Gly Val Pro Ser Arg Phe
    210                 215                 220
Ser Gly Ser Gly Ser Gly Thr Asp Phe Thr Leu Thr Ile Ser Ser Leu
225                 230                 235                 240
Gln Pro Glu Asp Phe Ala Thr Tyr Tyr Cys Gln Gln Tyr Arg Lys Leu
                245                 250                 255
Pro Trp Thr Phe Gly Gln Gly Thr Lys Leu Glu Ile Lys Arg Phe Val
            260                 265                 270
Pro Val Phe Leu Pro Ala Lys Pro Thr Thr Thr Pro Ala Pro Arg Pro
        275                 280                 285
Pro Thr Pro Ala Pro Thr Ile Ala Ser Gln Pro Leu Ser Leu Arg Pro
    290                 295                 300
Glu Ala Cys Arg Pro Ala Ala Gly Gly Ala Val His Thr Arg Gly Leu
305                 310                 315                 320
Asp Phe Ala Cys Asp Ile Tyr Ile Trp Ala Pro Leu Ala Gly Thr Cys
                325                 330                 335
Gly Val Leu Leu Leu Ser Leu Val Ile Thr Leu Tyr Cys Asn His Arg
            340                 345                 350
Asn Lys Arg Gly Arg Lys Lys Leu Leu Tyr Ile Phe Lys Gln Pro Phe
        355                 360                 365
Met Arg Pro Val Gln Thr Thr Gln Glu Glu Asp Gly Cys Ser Cys Arg
    370                 375                 380
Phe Pro Glu Glu Glu Glu Gly Gly Cys Glu Leu Gly Gly Gly Gly Ser
385                 390                 395                 400
Arg Val Lys Phe Ser Arg Ser Ala Asp Ala Pro Ala Tyr Gln Gln Gly
                405                 410                 415
Gln Asn Gln Leu Tyr Asn Glu Leu Asn Leu Gly Arg Arg Glu Glu Tyr
            420                 425                 430
Asp Val Leu Asp Lys Arg Arg Gly Arg Asp Pro Glu Met Gly Gly Lys
        435                 440                 445
Pro Arg Arg Lys Asn Pro Gln Glu Gly Leu Tyr Asn Glu Leu Gln Lys
    450                 455                 460
Asp Lys Met Ala Glu Ala Tyr Ser Glu Ile Gly Met Lys Gly Glu Arg
465                 470                 475                 480
Arg Arg Gly Lys Gly His Asp Gly Leu Tyr Gln Gly Leu Ser Thr Ala
                485                 490                 495
Thr Lys Asp Thr Tyr Asp Ala Leu His Met Gln Ala Leu Pro Pro Arg
            500                 505                 510
Gly Gly Gly Gly Ser Asn Val Leu Met Val His Lys Arg Ser His Thr
        515                 520                 525
Gly Glu Arg Pro Phe Gln Cys Asn Gln Cys Gly Ala Ser Phe Thr Gln
    530                 535                 540
Lys Gly Asn Leu Leu Arg His Ile Lys Leu His Thr Gly Glu Lys Pro
545                 550                 555                 560
```

Phe Lys Asp Pro Gly Asp Thr Ala Ser Ala Glu Ala Arg His Ile Lys
565                 570                 575

Ala Glu Met Gly
        580

<210> SEQ ID NO 39
<211> LENGTH: 1740
<212> TYPE: DNA
<213> ORGANISM: Artificial sequence
<220> FEATURE:
<223> OTHER INFORMATION: Construct 5 DNA Sequence

<400> SEQUENCE: 39

| | |
|---|---:|
| atggctcttc ctgtaaccgc acttctgctt cctcttgctc tgctgcttca tgctgctaga | 60 |
| cctcaggtgc agttagtgca atctggagct gaggtgaaga aacctggctc ttccgtgaaa | 120 |
| gtgagctgta agggaagcgg ctacaccttt accaactact ggatgcattg ggtgagacag | 180 |
| gcccctggac aggattagag tggattggag ccacatata gaggcacagc gataccctac | 240 |
| tacaaccaga agttcaaggg cagggccacc cttacagccg atacaagcac atctaccgcc | 300 |
| tacatggaac tgtcttctct gagaagcgag gataccgccg tgtactactg cacaagagga | 360 |
| gccatctacg acggctatga tgttctggac aattggggac agggcacact ggtgacagtg | 420 |
| tcttctggtg gtggcgggtc cggtggaggc ggatctggcg gtggggctc cggaggagga | 480 |
| ggttcagata ttcaaatgac acagagccca agcagcctgt ctgcttctgt gggcgataga | 540 |
| gtgaccatca cctgttctgc ttctcaggat atcagcaact acctgaactg gtaccagcag | 600 |
| aagcccggca agcccctaa actgctgatc tactacacca gcaatctgca ctctggagtt | 660 |
| cctagcagat tcagcggaag cggctctggc accgatttta cactgaccat ctcttctctg | 720 |
| cagcctgagg attttgccac ctactactgc agcagtacc ggaaattgcc ttggaccttt | 780 |
| ggacagggaa ccaagctgga gatcaagagg tttgtgcccg tgtttctgcc tgctaagcct | 840 |
| acaacaacac ctgcccctag accacctaca cctgctccta caattgcctc tcagcctctt | 900 |
| tctctgagac tgaagcttg cagacctgct gctggaggag ctgtgcatac aagaggactg | 960 |
| gattttgcct gcgatatcta catttgggct ccactggccg gcacatgtgg agttcttctg | 1020 |
| ctgtctctgg tgatcaccct gtactgtaat cacaggaaca agcggggccg aaaaaagctg | 1080 |
| ctgtacatct tcaagcagcc cttcatgaga ccagttcaga caacacagga ggaggacggc | 1140 |
| tgtagctgca gatttcctga ggaagaggaa ggaggatgtg aattaggtgg tggcgggagc | 1200 |
| agggtgaagt tctcacgcag cgcagatgct cctgcctatc agcaaggcca gaatcagctg | 1260 |
| tacaacgagc tgaatctggg cagaagagag gagtacgatg tgctggacaa gagaagggc | 1320 |
| agagatcctg aaatgggagg aaagcccaga aggaagaacc tcaagaagg cctgtacaat | 1380 |
| gagctgcaga aggacaagat ggccgaggcc tatagcgaga ttggcatgaa aggagagagg | 1440 |
| agaagaggaa agggccatga tggcctgtat cagggcctgt ctacagccac caaggataca | 1500 |
| tatgatgccc tgcatatgca ggctttaccc cctagaggag gagcggatc taacgtgctg | 1560 |
| atggtgcata aaagaagcca cacaggagag agaccattcc agtgcaacca gtgtggagcc | 1620 |
| agcttcaccc agaagggaaa tctgctgaga cacatcaaac tgcatacagg cgagaagccc | 1680 |
| ttcaaggacc ctggcgatac agcctctgct gaagctagac acattaaagc cgaaatgggc | 1740 |